(12) United States Patent
Chae et al.

(10) Patent No.: US 8,609,258 B2
(45) Date of Patent: Dec. 17, 2013

(54) LIGHT EMITTING DEVICES AND COMPOSITIONS

(75) Inventors: Hyun Sik Chae, San Diego, CA (US); Yutaka Ohmori, Kyoto (JP); Jesse Froelich, Vista, CA (US); Sheng Li, Vista, CA (US); Amane Mochizuki, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/460,661

(22) Filed: Apr. 30, 2012

(65) Prior Publication Data

US 2012/0305895 A1 Dec. 6, 2012

Related U.S. Application Data

(63) Continuation of application No. 12/167,127, filed on Jul. 2, 2008, now abandoned.

(60) Provisional application No. 60/948,164, filed on Jul. 5, 2007, provisional application No. 61/033,370, filed on Mar. 3, 2008.

(51) Int. Cl.
   *H01L 51/54*     (2006.01)
   *C07F 15/00*     (2006.01)
   *B05D 5/06*      (2006.01)

(52) U.S. Cl.
   USPC ........... 428/690; 428/917; 313/504; 313/506; 427/66; 546/4; 548/103; 252/301.16

(58) Field of Classification Search
   None
   See application file for complete search history.

(56) References Cited

U.S. PATENT DOCUMENTS

| | | | | |
|---|---|---|---|---|
| 5,635,249 A | * | 6/1997 | Haluska et al. | 427/387 |
| 6,018,002 A | * | 1/2000 | Pernisz | 525/326.5 |
| 6,406,804 B1 | * | 6/2002 | Higashi et al. | 428/690 |
| 6,517,958 B1 | * | 2/2003 | Sellinger et al. | 428/690 |
| 6,528,188 B1 | * | 3/2003 | Suzuki et al. | 428/690 |
| 6,657,224 B2 | * | 12/2003 | Shi et al. | 257/40 |

(Continued)

FOREIGN PATENT DOCUMENTS

| | | | |
|---|---|---|---|
| CN | 1680366 | * | 10/2005 |
| CN | 1810817 A | * | 8/2006 |

(Continued)

OTHER PUBLICATIONS

Derwent abstract for CN 1810817 A, Aug. 2006.*

(Continued)

*Primary Examiner* — Dawn L. Garrett
(74) *Attorney, Agent, or Firm* — Knobbe, Martens, Olson & Bear LLP

(57) ABSTRACT

A light emitting composition includes a light-emitting iridium-functionalized nanoparticle, such as a compound of formula (I). The compound of formula (I) further comprises at least one host attached to the core. A light emitting device includes an anode, a cathode, and a layer containing such a light-emitting composition is also disclosed. In an embodiment, the light emitting device can emit white light.

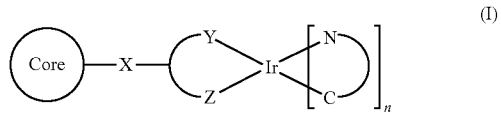

(I)

40 Claims, 11 Drawing Sheets

| cathode |
|---|
| EIL (electron injection layer) |
| ETL (electron transport) |
| HBL (hole blocking layer) |
| EML (emissive layer) |
| EBL (exciton blocking) |
| HTL (hole transport layer) |
| HIL (hole injection layer) |
| ITO (anode) | electrons holes

(56) References Cited

U.S. PATENT DOCUMENTS

| | | | |
|---|---|---|---|
| 6,870,054 | B1 | 3/2005 | Deaton et al. |
| 6,936,716 | B1 | 8/2005 | Lin |
| 6,939,624 | B2 | 9/2005 | Lamansky et al. |
| 6,989,273 | B2 | 1/2006 | Hsieh et al. |
| 7,001,536 | B2 | 2/2006 | Thompson et al. |
| 7,015,344 | B2 | 3/2006 | Deaton |
| 7,026,480 | B2 | 4/2006 | Che et al. |
| 7,078,115 | B2 | 7/2006 | Takiguchi et al. |
| 7,147,938 | B2* | 12/2006 | Helber et al. ............. 428/690 |
| 7,993,747 | B2 | 8/2011 | Mochizuki et al. |
| 2002/0034656 | A1 | 3/2002 | Thompson et al. |
| 2003/0120099 | A1* | 6/2003 | Laine et al. ............. 556/450 |
| 2003/0162299 | A1* | 8/2003 | Hsieh et al. ............. 436/84 |
| 2004/0100189 | A1 | 5/2004 | Adachi et al. |
| 2004/0230061 | A1 | 11/2004 | Seo et al. |
| 2005/0031903 | A1 | 2/2005 | Park et al. |
| 2005/0112400 | A1 | 5/2005 | Seo et al. |
| 2005/0123760 | A1* | 6/2005 | Cammack et al. ............. 428/403 |
| 2005/0238914 | A1 | 10/2005 | Lyu et al. |
| 2006/0063026 | A1 | 3/2006 | Holmes et al. |
| 2006/0177695 | A1 | 8/2006 | Ragini et al. |
| 2006/0186791 | A1* | 8/2006 | Yoshitake et al. ............. 313/503 |
| 2006/0217527 | A1 | 9/2006 | Chen et al. |
| 2006/0228578 | A1 | 10/2006 | Ren et al. |
| 2007/0184301 | A1* | 8/2007 | Oshiyama et al. ............. 428/690 |
| 2009/0066234 | A1 | 3/2009 | Chae et al. |
| 2009/0179552 | A1 | 7/2009 | Froehlich et al. |
| 2011/0193075 | A1 | 8/2011 | Mochizuki et al. |
| 2012/0273765 | A1* | 11/2012 | Froehlich et al. ............. 257/40 |
| 2012/0305895 | A1 | 12/2012 | Chae et al. |

FOREIGN PATENT DOCUMENTS

| | | |
|---|---|---|
| EP | 1 359 630 | 11/2003 |
| JP | 2004-506050 | 2/2004 |
| JP | 2005-521210 | 7/2005 |
| JP | 2006-108458 | 4/2006 |
| JP | 2007-169593 | 7/2007 |
| JP | 2007-184348 | 7/2007 |
| JP | 2007-214175 | 8/2007 |
| WO | WO 02/05971 | 1/2002 |
| WO | WO 2004/060898 | 7/2004 |
| WO | WO 2005/027583 | 3/2005 |
| WO | WO 2005/037955 | 4/2005 |
| WO | WO 2005/124889 | * 12/2005 |
| WO | WO 2007/136588 | 11/2007 |
| WO | WO 2009/006550 | 1/2009 |
| WO | WO 2009/064661 | 5/2009 |
| WO | WO 2010/045263 | 4/2010 |

OTHER PUBLICATIONS

Derwent abstract for CN 1680366 A, Oct. 2005.*
Faguang Xuebao, (2006), 27(5), pp. 700-704.*
Advanced Functional Materials, (2006), 16(11), pp. 1441-1448.*
Advanced Materials, (2006), 17(13), pp. 1769-1773.*
Dialog Results for CN 1680366 A Oct. 2005.*
Chen et al., Thin Solid Films, 514, (2006), pp. 103-109.*
Baldo et al., "High-Efficiency Phosphorescent Emission from Organic Electroluminescent Devices", Nature, Sep. 10, 1998, vol. 395, pp. 151-154.
Billmeyer, et al., "Principles of Color Technology", 2nd edition, John Wiley & Sons, Inc., New York, 1981, pp. 34-51.
Chao et al., White Light Emission from Exciplex in a Bilayer Device with two Blue Light-Emitting Polymers, Applied Physics Letters, Jul. 27, 1998, vol. 73, No. 4, pp. 426-428.
Chen et al., "Synthesis and Opto-Electrical Properties of Stellar Polyfluorene Derivatives Containing Polhedral Oligomeric Silsesquixanes as the Center Core", Journal of Polymer Research, Nov. 2, 2005, vol. 13, pp. 237-245.
Chen, K-B., et al. "Novel Dendritic Light-Emitting Materials Containing Polyhedral Oligomeric Silsesquioxanes Core", Thin solid films, 2006, vol. 514, pp. 103-109.
Cho et al., "Electroluminescent Polyhedral Oligomeric Silsesquioxane-Based Nanoparticle", Chemistry of Materials, Aug. 8, 2006, vol. 18, No. 16, 3780-3787.
CIE 1971, International Commission on Illumination, Colorimetry: Official Recommendations of the International Commission on Illumination, Publication CIE No. 15 (E-1.3.1) 1971, Bureau Central de la CIE, Paris, 1971.
Evans et al., "Coordinationg Complexes Exhibiting Room-Temperature Phosphoresence: Evaluation of their Suitability as Triplet Emitters in Organic Light Emitting Diodes", Coordination Chemistry Reviews, Mar. 6, 2006, vol. 250, pp. 203-2126.
Fenenko et al., "Electronic Characterization of New Bright-Blue-Light-Emitting Poly(9,9-dioctylfluorenyl-2,7-diyl)-End Capped With Polyhedral Oligomeric Silsesquioxanes", Japanese Journal of Applied Physics, 2006, vol. 45, No. 1B, pp. 550-554.
Fréchet et al., "Synthesis and Properties of Dendrimer and Hyperbranched Polymers", Comprehensive Polymer Science, 1996, pp. 71-132.
Gao et al., "White Light Electroluminescence From a Hole-Transporting Layer of Mixed Organic Materials", Synthetic Metals, 2000, vol. 111-112, pp. 39-42.
Gerlach et al., "Synthese von endo-und exo-1,3-Dimethyl-2,9-dioxabicyclo[3.3.1]nonan", Helvetica Chemica Acta, 1977, vol. 60, No. 2, pp. 638-642.
Gong et al., "White Light Electrophosphorescence from Polyfluorene-Based Light-Emitting Diodes: Utilization of Fluorenone Defects", The Journal of Physical Chemistry, Jun. 24, 2004, vol. 108, No. 25, pp. 8601-8605.
Granström et al., "White Light Emission from a Polymer Blend Light Emitting Diode", Applied Physics Letters, Jan. 8, 1996, vol. 68, No. 2, pp. 147-149.
Gustafsson et al. "Flexible Light-Emitting Diodes Made from Soluble Conducting Polymer," Nature, Jun. 11, 1992, vol. 357, pp. 477-479.
Hamada et al., "White Light-Emitting Material for Organic Electroluminescent Devices", Japanese Journal of Applied Physics, Oct. 15, 1996, vol. 35, pp. 1339-1341, Part 2, No. 10B.
He et al., "Highly Efficient Luminescent Organic Cluster with Quantum Dot-Like Properties," Journal of American Chemical Society, 2004, vol. 126, No. 25, pp. 7792-7793.
Holder et al., "New Trends in the Use of Transition Metal-Ligand Complexes for Applications in Electroluminescent Devices", Advanced Materials, May 2, 2005, vol. 17, No. 9, pp. 1109-1121.
Imae et al., "Unique Photoluminescence Property of a Novel Perfectly Carbazole-Substituted POSS", Journal of Materials Chemistry, 2005, vol. 15, pp. 4581-4583.
Jiang et al., "High Efficiency, Saturated Red-Phosphorescent Polymer Light-Emitting Diodes Based on Conjugated and Non-Conjugated Polymers Doped with an Ir Complex" Advanced Materials, Mar. 18, 2004, vol. 16, No. 6, pp. 537-541.
Kawamura, et al., "Energy Transfer in Polymer Electrophorescent Light Emitting Devices with Single and Multiple Doped Luminescent Layers", Journal of Applied Physics, Jul. 1, 2002, vol. 92, No. 1, pp. 87-93.
Kido et al., "Multilayer White Light-Emitting Organic Electroluminescent Device", Science, Mar. 3, 1995, vol. 267, pp. 1332-1334.
Kido et al., "White Light-Emitting Organic Electroluminescent Device Using Lanthanide Complexes", Japanese Journal of Applied Physics, Mar. 15, 1996, vol. 35, pp. 394-396, Part 2, No. 3B.
Kido et al., "White Light-Emitting Organic Electroluminescent Devices Using the Poly(N-Vinylcarbazole) Emitter Layer Doped with Three Fluorescent Chromophores", Applied Physics Letters, Feb. 1994, vol. 64, Issue 815.
Kolosov et al., "1,8-Naphthalimides in Phosphorescent Organic LEDs: The Interplay Between Dopant, Exciplex, and Host Emission", Journal of American Chemistry Society, Aug. 21, 2002, vol. 124, No. 124, pp. 9945-9954.
Lamansky et al., "Cyclometalted Jr Complexes in Polymer Organic Light-Emitting Devices", Journal of Applied Physics, Aug. 1, 2002, vol. 92, No. 3, pp. 1570-1575.
Lamansky et al., "Highly Phosphorescent Bis-Cyclometalated Iridium Complexes: Synthesis, Photophysical Characterization, and

(56) References Cited

OTHER PUBLICATIONS

Use in Organic Light Emitting Diodes", Journal of the American Chemical Society, May 9, 2001, vol. 123, No. 18, pp. 4304-4312.

Lamansky et al., "Synthesis and Characterization of Phosphorescent Cyclometalated Iridium Complexes", Inorganic Chemistry, Mar. 26, 2001, vol. 40, No. 7, pp. 1704-1711.

Lee et al., "Polymer Phosphorescent Light-Emitting Devices Doped with Tris(2-phenylpyridine) Iridium as a Triplet Emitter", Applied Physics Letters, Oct. 9, 2000, vol. 77, No. 15, pp. 2280-2282.

Lee et al., "Stabalized Blue Luminescent Polyfluorenes: Introducing Polyhedral Oligomeric Silsesquioxane", Macromolecules, 2004, vol. 37, pp. 8523-8529.

Lee et al., "Synthesis of Polyhedral Oligomeric Silsesquioxane-Functionalized Polyfluorenes: Hybrid Organic-Inorganic Π -Conjugated Polymers", Synthetic Metals, 2006, vol. 156, No. 7-8, pp. 590-596.

Lee et al., "White Light Electroluminescence from Soluble Oxadiazole-Containing Phenylene Vinylene Ether-Linkage Copolymer", Applied Physics Letters, Jul. 16, 2001, vol. 79, Issue 3, pp. 308-310.

Lowry et al., "Synthetically Tailored Excited States: Phosphorescent, Cyclometalated Iridium(III) Complexes and Their Applications", Chemistry: A European Journal, 2006, vol. 12, No. 31, pp. 7971-7977.

Nonoyama, Matsuo, "Benzo[$h$]quinolin-10-yl-N Iridium (III) Complexes", Bulletin of the Chemical Society of Japan, 1974, vol. 47, No. 3, pp. 767-768.

Odian, "Principles of Polymerization", John Wiley, New York, 2nd Ed., 1981, pp. 177-179.

Sellinger et al., "Heck Coupling of Haloaromatics with Octavinylsilsesquioxane:Solution Precessable Nanocomposites for Application in Electroluminescent Devices", The Royal Society of Chemistry, 2005, pp. 3700-3702.

Sorenson et al., "Preparative Methods of Polymer Chemistry", John Wiley, New York, 3rd ed., 2001, pp. 442-444.

Sprouse et al., "Photophysical Effects of Metal-Carbon σ Bonds in Ortho-Metalated Complexes of Ir(III) and Rh(III)", Journal of American Chemical Society, 1984, vol. 106, No. 22, pp. 6647-6653.

Su et al., "Highly Efficient Red Electrophorescent Devices Based on Iridium Isoquinoline Complexes: Remarkable External Quantum Efficiency Over a Wide Range of Current", Advanced Materials, vol. 15, No. 11, Jun. 5, 2003, pp. 884-888.

Suzuki et al., "Highly Efficient Polymer Light-Emitting Devices Using Ambipolar Phosphorescent Polymers", Applied Physics Letters, 2005, vol. 86, pp. 103507-1-103507-3.

Tasch et al., "Efficient White Light-Emitting Diodes Realized with New Processable Blends of Conjugated Polymers", Applied Physics Letters, Nov. 17, 1997, vol. 71, No. 20, pp. 2883-2885.

Xiao et al., "Nano-Hybrid Luminescent Dot: Synthesis, Characterization and Optical Properties", Journal of Materials Chemistry, 2006, vol. 16, pp. 829-836.

Yang et al., "Efficient Blue-Green and White Light-Emitting Electrochemical Cells Based on Poly[9,9-bis(3,6-dioxaheptyl)-fluorene-2,7-diyl]" Journal of Applied Physics, Apr. 1, 1997, vol. 81, No. 7, pp. 3294-3298.

Yang et al., "Use of Poly(9-vinylcarbazole) as Host Material for Iridium Complexes in High-Efficiency Organic Light-Emitting Devices", Japanese Journal of Applied Physics, Aug. 1, 2000, vol. 39, No. 8, pp. 828-829.

Yeh et al., "New Dopant and Host Materials for Blue-Light-Emitting Phosphorescent Organic Electroluminescent Devices", Advanced Materials, Feb. 10, 2005, vol. 17, No. 3, pp. 285-289.

You et al., "Inter-Ligand Energy Transfer and Related Emission Change in the Cyclometalated Heteroleptic Iridium Complex: Facile and Efficient Color Tuning over the Whole Visible Range by the Ancillary Ligand Structure," Journal of American Chemical Society, 2005, vol. 127, pp. 12438-12439.

Zhao et al., "On the Origin of Green Emission in Polyfluorene Polymers: The Roles of Thermal Oxidation Degradation and Crosslinking" Advanced Functional Materials, 2004, vol. 14, No. 8, pp. 783-790.

International Search Report and Written Opinion in PCT Application No. PCT/US2008/069091 dated Oct. 27, 2008.

International Preliminary Report on Patentability in PCT Application No. PCT/US2008/069091 dated Oct. 14, 2009.

Zhao et al., "Studies of Third-Order Optical Nonlinearities of Model Compounds Containing Benzothiazole, Benzimidazole, and Benzoxazole Units", Chemistry of Materials, 1990, vol. 2, pp. 670-678.

\* cited by examiner

LIGHT EMITTING DEVICES AND COMPOSITIONS

CROSS-REFERENCE TO RELATED APPLICATIONS

The present application is a continuation of U.S. patent application Ser. No. 12/167,127, filed Jul. 2, 2008, now abandoned, which claims priority under 35 U.S.C. §119(e) to U.S. Provisional Application No. 60/948,164 filed on Jul. 5, 2007 and U.S. Provisional Application No. 61/033,370 filed on Mar. 3, 2008, the disclosures of which are incorporated by reference herein in their entireties.

BACKGROUND

1. Field of the Invention

This invention relates to light emitting compositions and light-emitting devices that include the light-emitting compositions. Specifically, this invention relates to light emitting compositions and light-emitting devices that include iridium-functionalized nanoparticles.

2. Description of the Related Art

Organic electroluminescent devices capable of emitting white light are desirable because of their potential utility as backplane lights for displays, overhead lighting and other lightweight, low profile, low power lighting applications. White light-emitting Organic Light-Emitting Diode (OLED) devices with high color purity and brightness exceeding 2000 cd/m² have been demonstrated at least since 1994. (1, 2) However, there is considerable difficulty in preparing white emitting OLEDs because it is generally quite difficult to prepare a device with a single layer that can emit white light. Several ineffective strategies have been employed to generate white light by electroluminescence including: preparation of devices with multiple emitting layers, e.g. red, green and blue (2); use of a single emitting layer doped with multiple small molecule emitters of different colors (1, 3, 4); blends of different color emitting polymers (5, 6); excimer (7) or "electromer" (8) emission from a semiconducting polymer; excimer emission from an interface (9); and broad emission from metal chelates (10).

There are significant drawbacks to all of these approaches. Preparation of devices with multiple emitting layers is typically more difficult and time consuming than preparation of devices with fewer layers. Device failure is more likely to occur due to interfacial defects, and matching the conduction band energies of multiple layers is complicated at best. Small molecules tend to have limited solubility in polymers. Blends of small molecule emitters and polymer dispersions of emitters tend to aggregate or phase separate, which often results in decreased device performance and poor color stability. Excimers and electromers often show field dependent emission spectra and their formation changes the transport properties of the device. Classical polymer-based systems are typically difficult to purify and exhibit poor batch-to-batch reproducibility. It is also very difficult to control the structure of classical polymer-based systems except in a very general sense. Finally, broad spectral emission from small single molecules typically heavily consists of green wavelength components and has a much lower efficiency for the red and blue components. The human eye is most sensitive to green light; hence in an actual device, it is desirable to have the red and blue wavelength components brighter than the green components. Molecular orbital and quantum mechanical theories forbid this type of emission from a single small molecule material.

Recently, phosphorescent dyes have been used as a source of emission in OLEDs because of their potential for achieving high degrees of luminescence efficiency. In theory, phosphorescence can achieve 100% quantum efficiency by emitting from both the singlet and triplet state as compared to fluorescence which only emits from the singlet state and is thus limited to a theoretical efficiency of 25% (11).

The following articles are referred to above and incorporated by reference herein in their entireties:

1. Kido, J., Hongawa, K., Okuyama, K. & Nagai, K. White light-emitting organic electroluminescent devices using the poly(N-vinylcarbazole) emitter layer doped with three fluorescent chromophores. *Applied Physics Letters* 64, 815 (1994).
2. Kido, J., Kimura, M. & Nagai, K. Multilayer White light-Emitting Organic Electroluminescent Device. *Science* 267, 1332-1334 (1995).
3. Kido, J., Ikeda, W., Kimura, M. & Nagai, K. *Jpn. J. Appl. Phys.* (part 2) 35, L394 (1996).
4. Tasch, S. et al. *Applied Physics Letters* 71, 2883 (1997).
5. Yang, Y. & Pei, Q. *Journal of Applied Physics* 81, 3294 (1997).
6. Granstrom, M. & Inganas, O. *Applied Physics Letters* 68, 147 (1996).
7. Gao, Z. Q., Lee, C. S., Bello, I. & Lee, S. T. White light electroluminescence from a hole-transporting layer of mixed organic materials. *Synthetic Metals* 111-112, 39-42 (2000).
8. Lee, Y.-Z. et al. White light electroluminescence from soluble oxadiazole-containing phenylene vinylene ether-linkage copolymer. *Applied Physics Letters* 79, 308-310 (2001).
9. Chao, C.-I. & Chen, S.-A. White light emission from exciplex in a bilayer device with two blue light-emitting polymers. *Applied Physics Letters* 73, 426-428 (1998).
10. Hamada, Y. et al. White light-emitting material for organic electroluminescent devices. *Jpn. J. Appl. Phys.* (part 2) 35, L1339-L1341 (1996).
11. Baldo, M. A.; O'Brien, D. F.; You, Y.; Shoustikov, A.; Sibley, S.; Thompson, M. E.; Forrest, S. R. *Nature* 395, 151 (1998).

SUMMARY

The inventors have discovered methods for making light emitting compositions and devices using a nanoparticle approach. Some embodiments described herein relate to an iridium-functionalized nanoparticle that can include a nanoparticle core and an iridium-complex. In preferred embodiments, the iridium-functionalized nanoparticles described herein are light-emitting, e.g., white light-emitting. Various embodiments provide a composition that comprises an iridium-functionalized nanoparticle as described herein.

An embodiment described herein relates to a light emitting composition that can include one or more compound of formula (I):

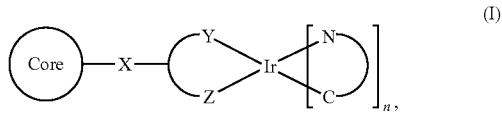

wherein the core can be a nanoparticle core, n can be 2, X is a single bond or each

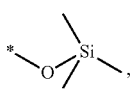

can be independently a first optionally substituted bidentate ligand;

can be a second optionally substituted bidentate ligand selected from:

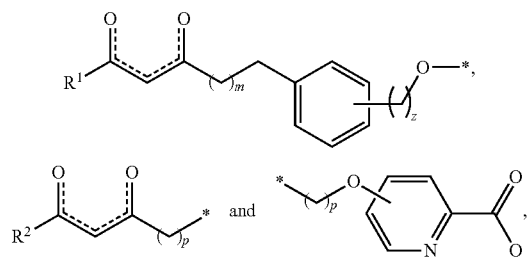

wherein m is an integer in the range of 1 to 9, p is an integer in the range of 1 to 20, z is 0, 1 or 2, $R^1$ is selected from alkyl, substituted alkyl, aryl and substituted aryl, and $R^2$ is selected from: alkyl, substituted alkyl, aryl and substituted aryl, and * indicates a point of attachment to the core or X. In some embodiments, the one or more compound of formula (I) may further comprise at least one host attached to the core, wherein the at least one host comprises a hole transport material, an electron transport material or a mixture thereof.

In some embodiments, the first optionally substituted bidentate ligand can be selected from:

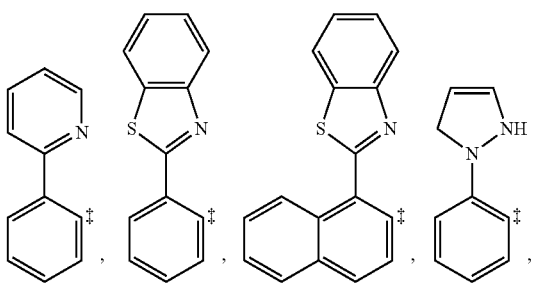

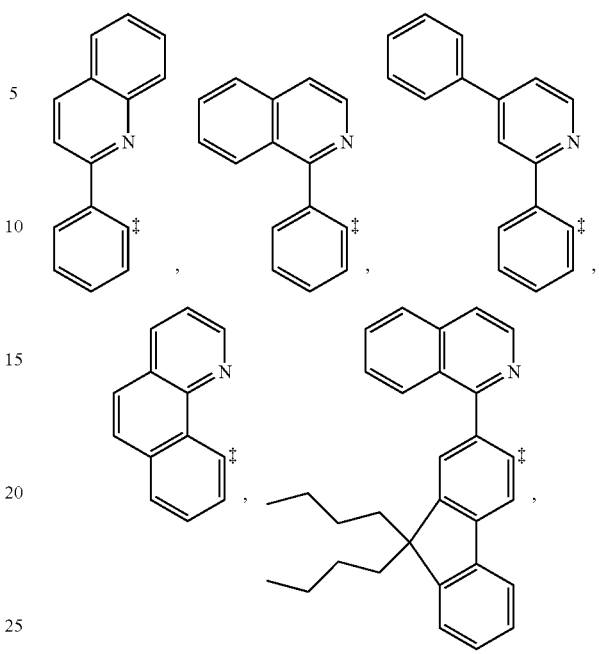

and optionally substituted derivatives thereof, wherein ‡ indicates the carbon attached to the Ir.

In some embodiments, the first optionally substituted bidentate ligand can be selected from:

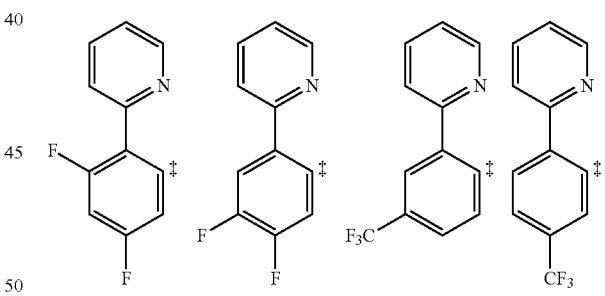

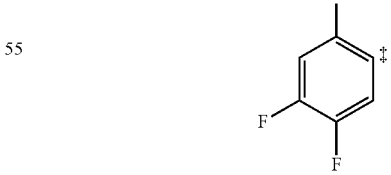

wherein ‡ indicates the carbon attached to the Ir.

In some embodiments, the first bidentate ligands can be selected from:

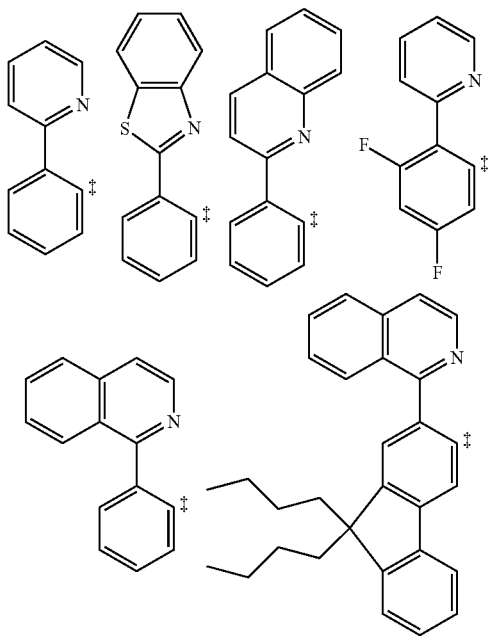

wherein ‡ indicates the carbon attached to the Ir. If desired, in some embodiments, the first bidentate ligands can be the same as one another.

Another embodiment described herein relates to a light emitting device that can include: an anode layer comprising a high work function metal; a cathode layer comprising a low work function metal; and a light-emitting layer positioned between, and electrically connected to, the anode layer and the cathode layer, wherein the light-emitting layer can include an iridium-functionalized nanoparticle or composition thereof as described herein. In an embodiment, the iridium-functionalized nanoparticle is represented by Formula (I). In an embodiment, the iridium-functionalized nanoparticle is an organic-inorganic iridium-functionalized nanoparticle. In an embodiment, the organic-inorganic iridium-functionalized nanoparticle comprises a nanoparticle core that comprises inorganic elements such as phosphorous (P), silicon (Si), and/or a metal. For example, in an embodiment a nanoparticle core comprises a moiety selected from the group consisting of a silsesquioxane, a cyclophosphazene, a triazine, a cyclodextrin, a calizarene, a phthalocyanine, and a silica particle. The light-emitting compositions described herein can include one or more iridium-functionalized nanoparticles and/or other materials in addition to the iridium-functionalized nanoparticle(s).

In some of the embodiments described herein the light-emitting composition is configured to emit light such as blue, green, orange, red and white.

In an embodiment, the process for making the light-emitting devices described herein, include forming the light-emitting layer by a wet process.

These and other embodiments are described in greater detail below.

DETAILED DESCRIPTION

Figure 1:
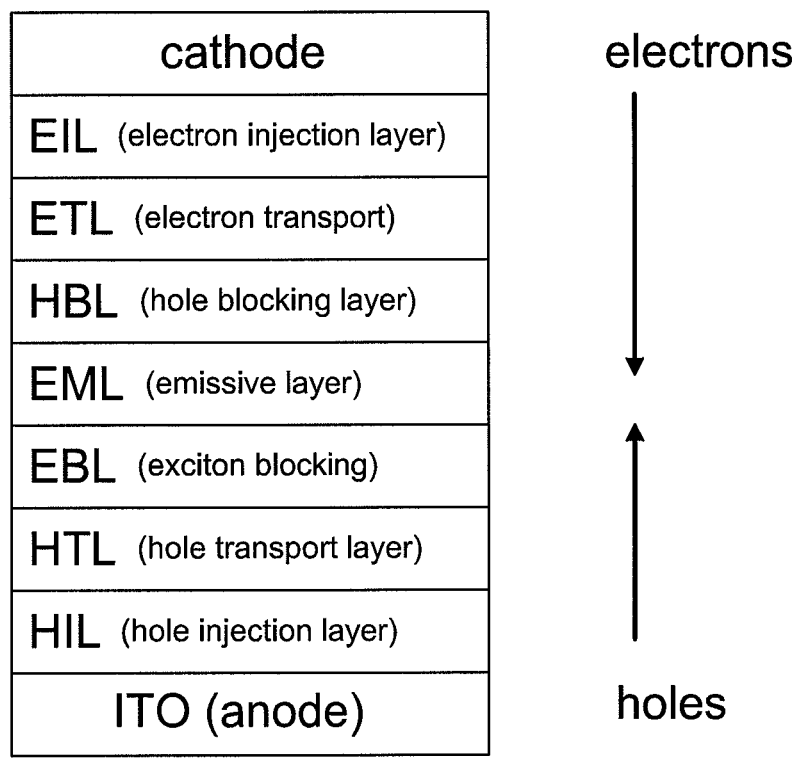
FIG. 1 shows an exemplary configuration of an organic light-emitting device.

A nanoparticle is a particle having a cross-sectional measurement (e.g., diameter if spherical) of about 100 nm or less. Dendrimers are examples of nanoparticles. Nanoparticles may be soluble or insoluble polymers (copolymers, hyperbranched polymers, etc), having the ability to aggregate, accumulate and/or self-assemble into particles of about 100 nm or less. The silsesquioxane group of the formula (II) is an example of a nanoparticle.

Dendrimers are branched molecular materials that exhibit useful properties of both small molecules and polymers. See e.g. Fréchet, J. M. J.; Hawker, C. J. Comprehensive Polymer Science, 2nd Supplement; Pergamon: Oxford, England, 1996; pp 71-132. A dendrimer is a substantially monodisperse synthetic macromolecule possessing a three-dimensional architecture that comprises a central core, highly branched but substantially regular iterative building units, and numerous peripheral ending groups. A more detailed description of these terms is found in G. Odian, Principles of Polymerization, John Wiley, New York, $2^{nd}$ Ed., 1981, pp. 177-179 and in W. R. Sorenson, F. Sweeney and T. W. Campbell, Preparative Methods of Polymer Chemistry, John Wiley, New York, 3rd ed., 2001, pp. 442-444, both of which are hereby incorporated by reference in their entireties. The numerous functional groups in the periphery of dendrimers are ideally suited for the incorporation of light-emitting lumophores, e.g., by covalent bonding. Modifications of peripheral functional groups in dendrimers to accommodate the attachment of lumophores can be carried out by general methods described in "Dendrimers III: Design Dimension Function", Vögtle, F., Vol. Ed. Top. Curr. Chem. 2001, 212. Similar methods may also used to functionalize polymer nanoparticles.

Unless otherwise indicated, when a substituent referred to as being "optionally substituted," or "substituted" it is meant that the substituent is a group that may be substituted with one or more group(s) containing about 1 to about 20 atoms individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The term "aryl" as used herein refers to single $C_{3-20}$ carbocyclic and poly-$C_{3-20}$ carbocyclic ring systems with a fully delocalized pi-system. Exemplary aryl groups are phenyl and naphthyl.

The term "alkyl" as used herein is a linear or branched chain of one to thirty-five carbon atoms. Examples of alkyl groups include but are not limited to methyl, ethyl, propyl, isopropyl, n-butyl, iso-butyl, tert-butyl, and the like.

The term "cycloalkyl" as used herein refers to fully saturated single carbocyclic and poly-carbocyclic ring systems with three to thirty five carbon atoms.

A "monodentate ligand" refers to a ligand which forms one bond (e.g., a coordinate covalent bond and/or covalent bond) to a central atom, such as a metal ion, A monodentate ligand can be a neutral molecule or an ion with a lone pair. A "bidentate" ligand refers to a ligand which forms two bonds (e.g., a coordinate covalent bond and/or covalent bond) to a central atom.

As used herein, the term "phosphorescence" refers to emission from a triplet excited state of an organic molecule. The term "fluorescence" refers to emission from a singlet excited state of an organic molecule.

An "aggregate emitter" comprises two or more light-emitting compounds that are bound in the ground state and/or in the excited state. An "excimer" is a dimer with an excited state wavefunction that extends over two identical molecules, and is formed when the light-emitting compounds comprising the aggregate emitters are bound in the excited state but not in the ground state.

The term "silsesquioxane" is the general name for a family of polycyclic compounds consisting of silicon and oxygen. Silsesquioxanes are also known as silasesquioxanes and polyhedral oligomeric silsesquioxanes (POSS).

The "work function" of a metal is a measure of the minimum energy required to extract an electron from the surface of the metal.

A "high work function metal" is a metal or alloy that easily injects holes and typically has a work function greater than or equal to 4.5.

A "low work function metal" is a metal or alloy that easily loses electrons and typically has a work function less than 4.3.

A "wet process" is used herein in its ordinary sense as understood by those skilled in the art and includes a process of laying down a layer where the materials that are included in the layer are in aqueous or organic solution. Examples of wet processes include but are not limited to spraying, spin coating, drop casting, inkjet printing and screen printing.

A material is white light-emitting if it emits white light. White light is light having the approximate CIE color coordinates ($X=\frac{1}{3}$, $Y=\frac{1}{3}$). The CIE color coordinates ($X=\frac{1}{3}$, $Y=\frac{1}{3}$) is defined as the achromatic point. The X and Y color coordinates are weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

An embodiment provides an iridium complex attached to the nanoparticle core. In some embodiments, the iridium-complex can be a phosphorescent emitter. In an embodiment, the iridium-functionalized nanoparticle is represented by Formula (I) as follows:

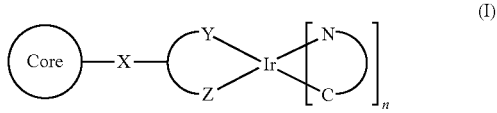

The core in Formula (I) represents the nanoparticle core, while

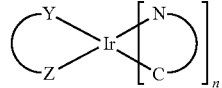

represents the iridium complex. The n in the iridium complex is 2, each

is independently a first optionally substituted bidentate ligand, and

is a second optionally substituted bidentate ligand. The X in Formula (I) may be a single bond or

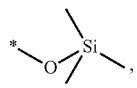

wherein * indicates the attachment to the core. In some embodiments, the iridium-functionalized nanoparticle of Formula (I) further comprises at least one host having the formula

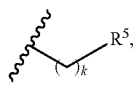

wherein k is 0 or an integer selected from 1, 2, 3, 4, 5, 6, 7, 8, 9, 10, 11, 12, 13, 14, 15, 16, 17, 18, 19 and 20. The

indicates that the bond is attached to the core. In some embodiments, the host may comprise a hole transport material or an electron transport material, and a mixture of the hole transport and electron transport hosts can be attached to the core.

In some embodiments, the iridium-functionalized nanoparticle may be represented by the following formulas:

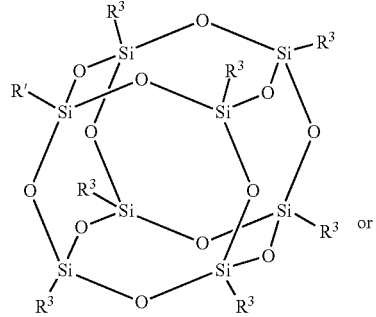

(II)

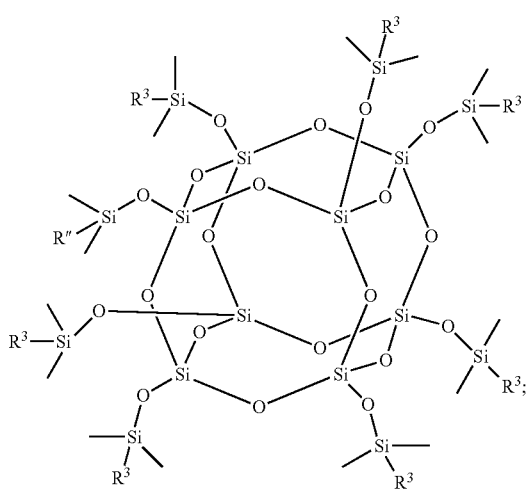

(III)

wherein both R' and R" are Ir complexes, R' is represented by

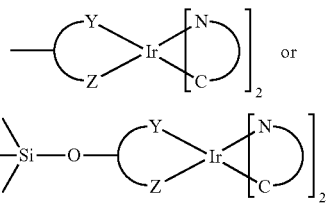

and R" is represented by

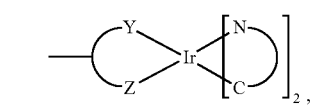

wherein each

is independently a first optionally substituted bidentate ligand, and

is a second optionally substituted bidentate ligand. The $R^3$ is
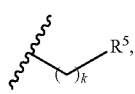
wherein k is 0 or an integer selected from 1 to 20. In some embodiments, $R^3$ may be a host, and each $R^5$ in Formula (I), (II), and (III) can be independently selected from the following:
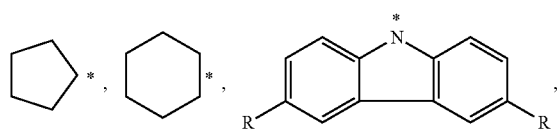
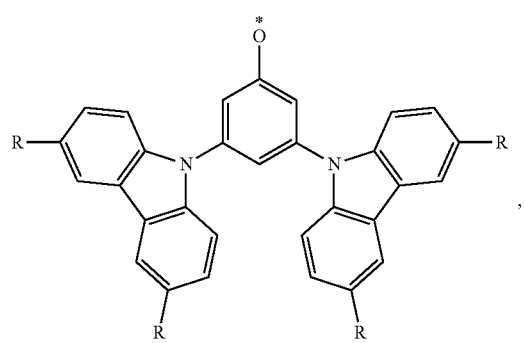
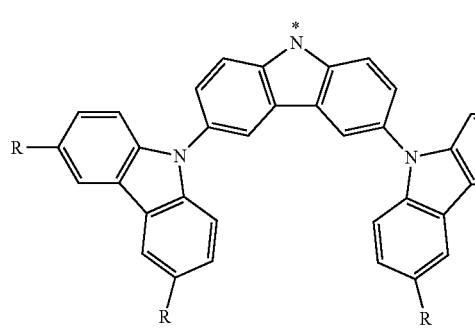
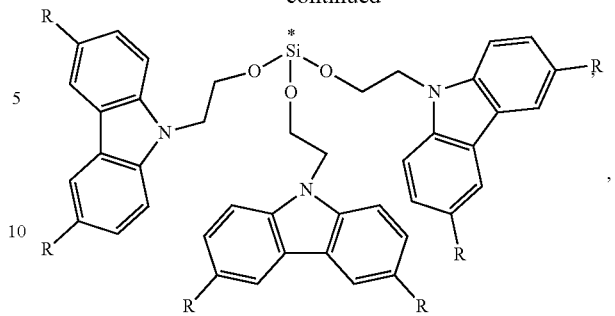
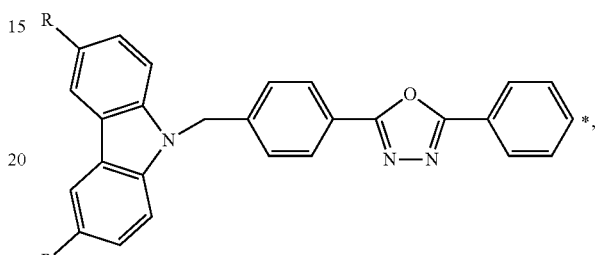
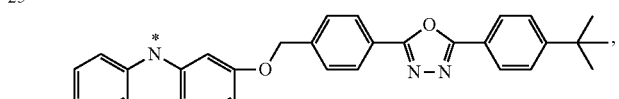
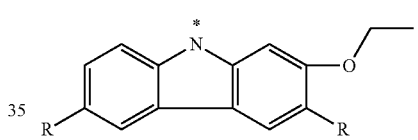
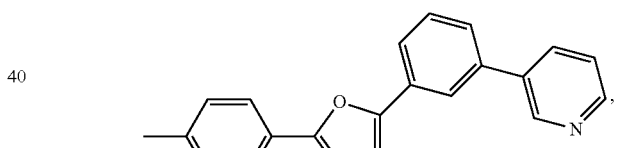
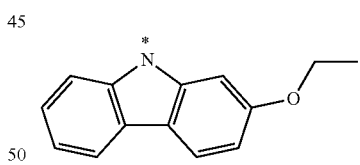
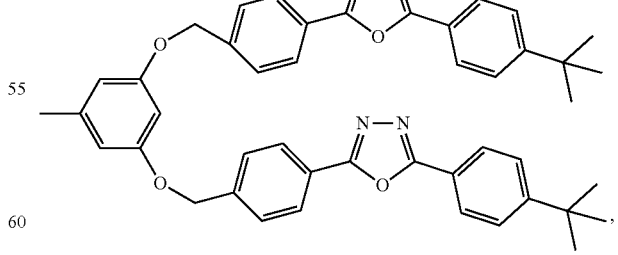
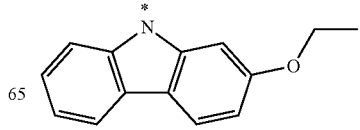

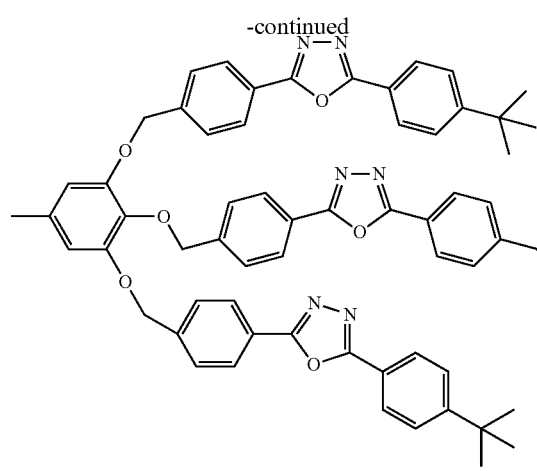

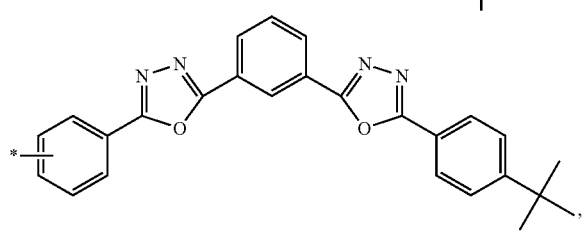

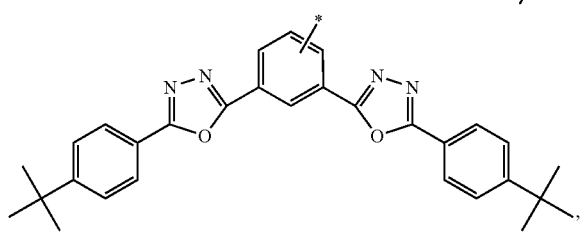

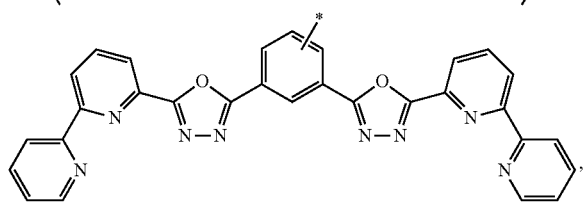

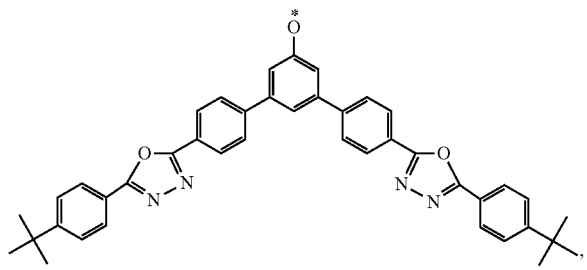

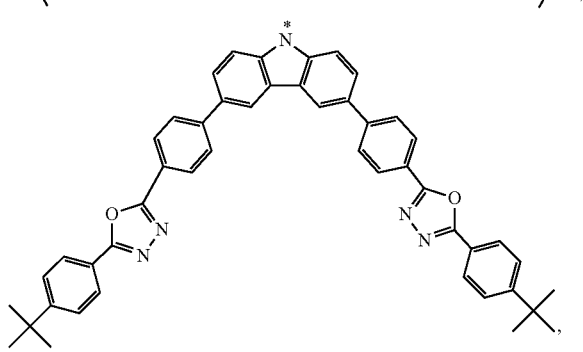

and

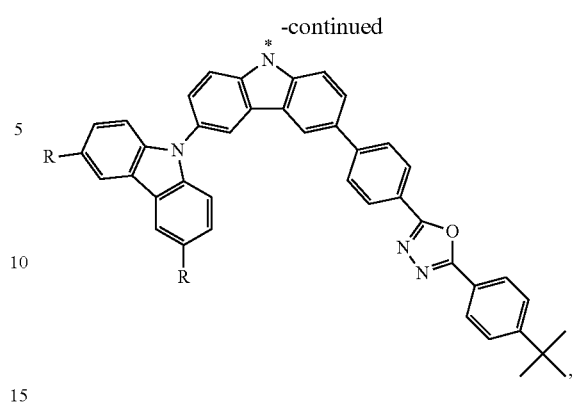

wherein R is independently selected from H or alkyl, and * indicates a point of attachment to Si or the alkyl group in $R^3$. In some embodiments, more than one host may be present in a iridium-functionalized nanoparticle complex. In some embodiments, a light-emitting composition may comprise a plurality of the iridium-functionalized nanoparticles independently selected from the compounds of Formula (I), (II) or (III).

In some embodiments, the first optionally substituted bidentate ligand may be independently selected from the following:

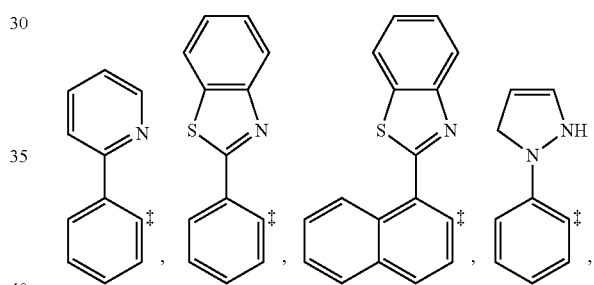

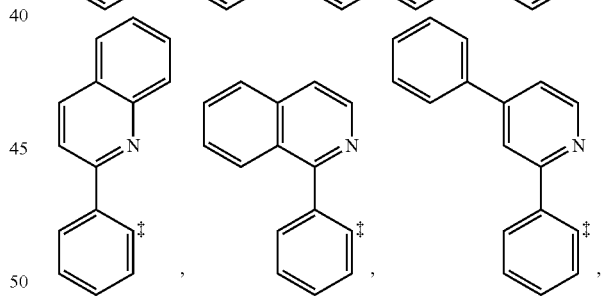

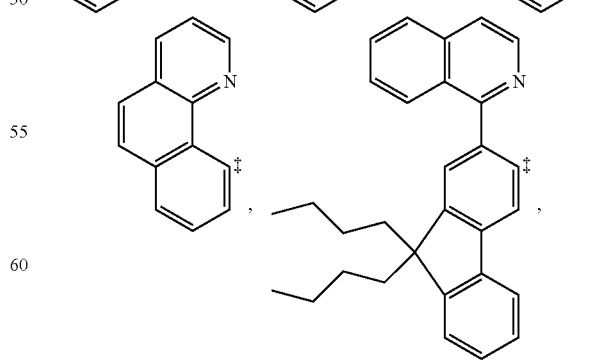

and optionally substituted derivatives thereof, wherein ‡ indicates a point of attachment to the Ir. In some embodiments, the first optionally substituted bidentate ligand may also be independently selected from substituted derivatives of the following:

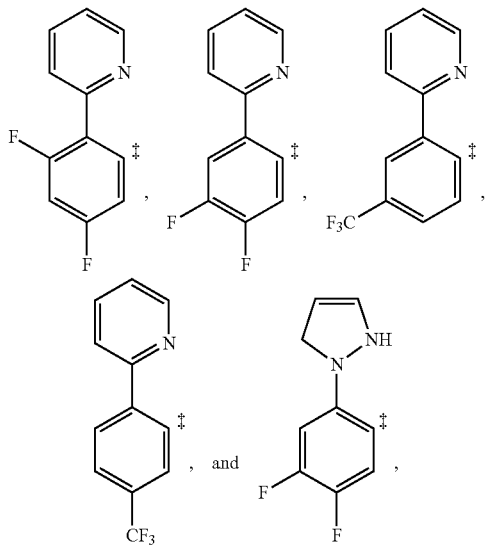

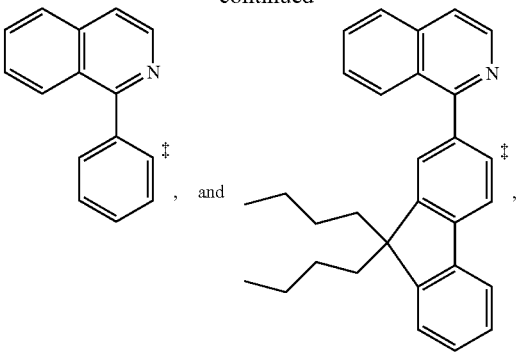

wherein ‡ indicates a point of attachment to the Ir. In some embodiments, the two bidentate ligands or the two optionally substituted bidentate ligands may be the same.

In some embodiments, the second optionally substituted bidentate ligand may be selected from the following group:

wherein ‡ indicates a point of attachment to the Ir. In some embodiments, the first bidentate ligand may be independently selected from the following:

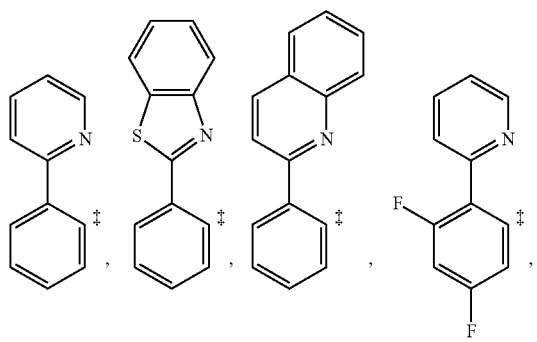

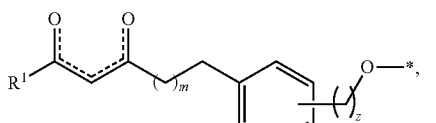

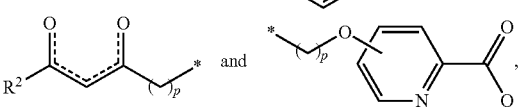

wherein m is an integer in the range of 1 to 9, p is an integer in the range of 1 to 20, z is 0, 1 or 2, $R^1$ is selected from alkyl, substituted alkyl, aryl and substituted aryl, and $R^2$ is selected from: alkyl, substituted alkyl, aryl and substituted aryl; and * indicates a point of attachment to the core or X.

An embodiment described herein relates to a light-emitting composition that comprises one or more compound of formula (I) selected from:

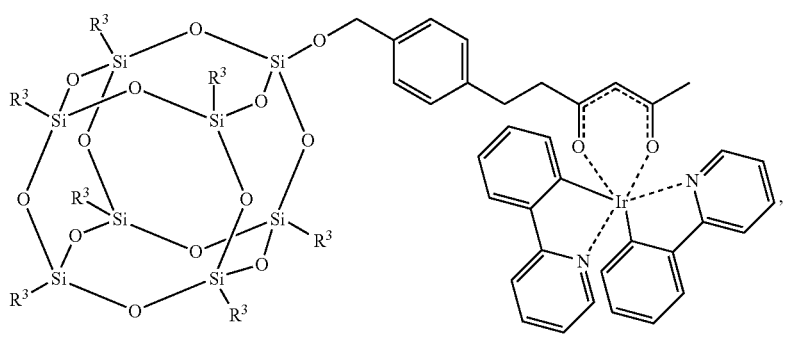

-continued
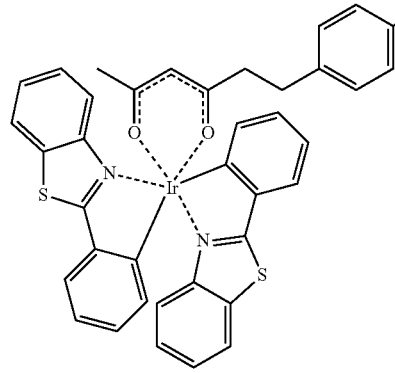
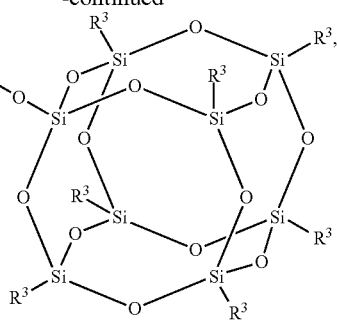
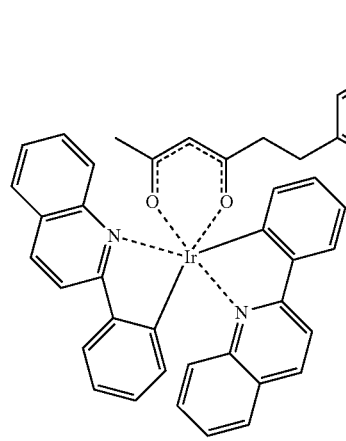
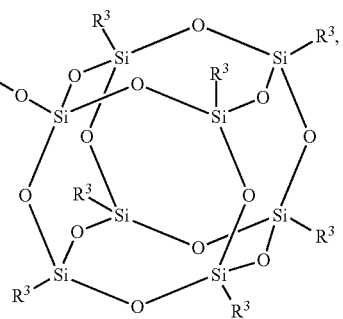
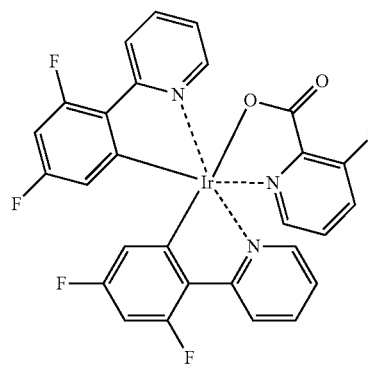
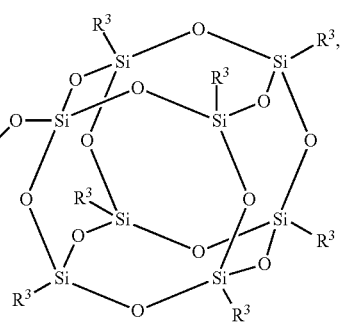
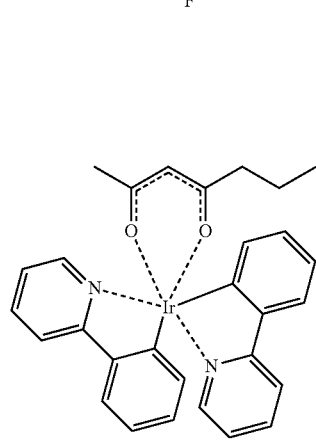
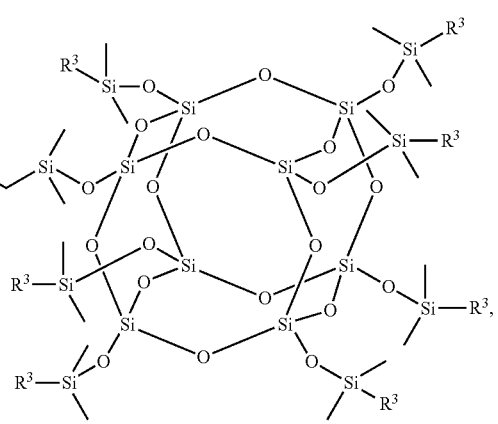

-continued
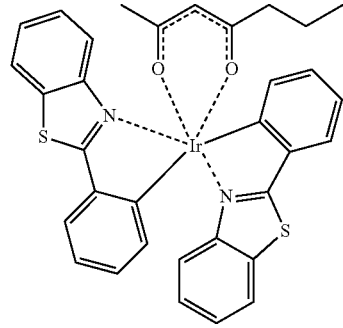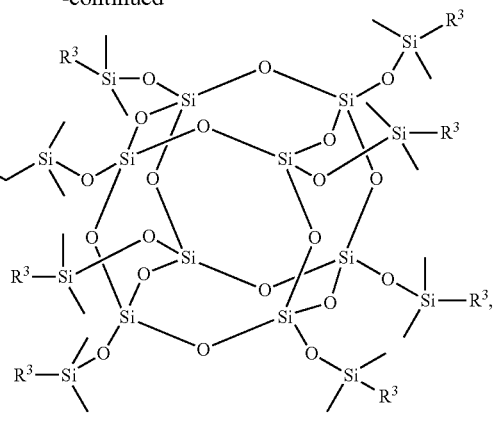
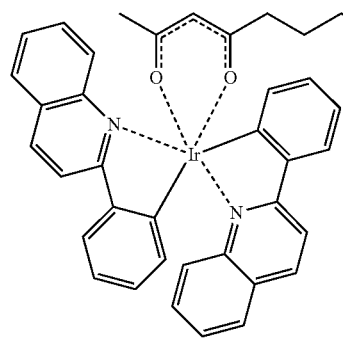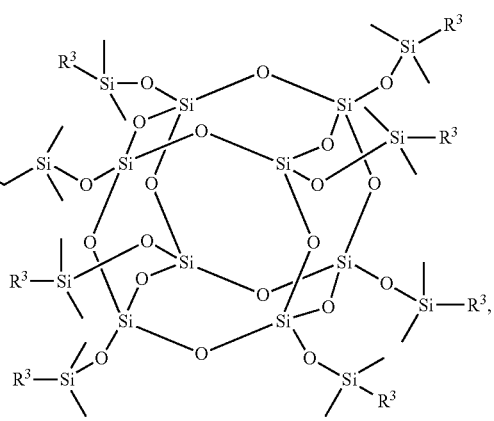
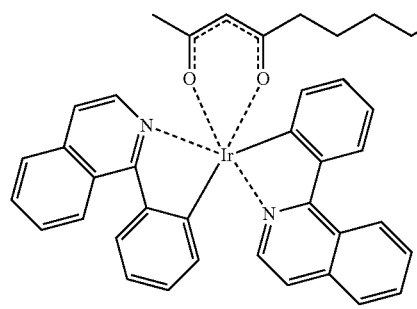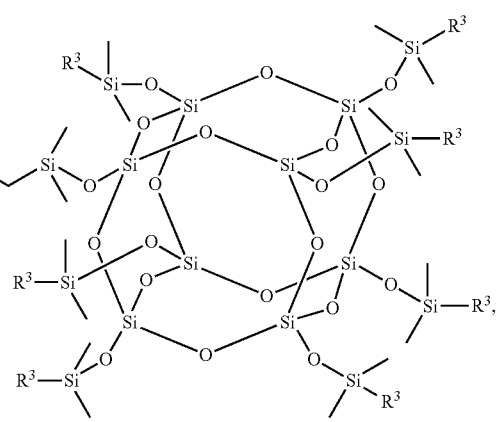

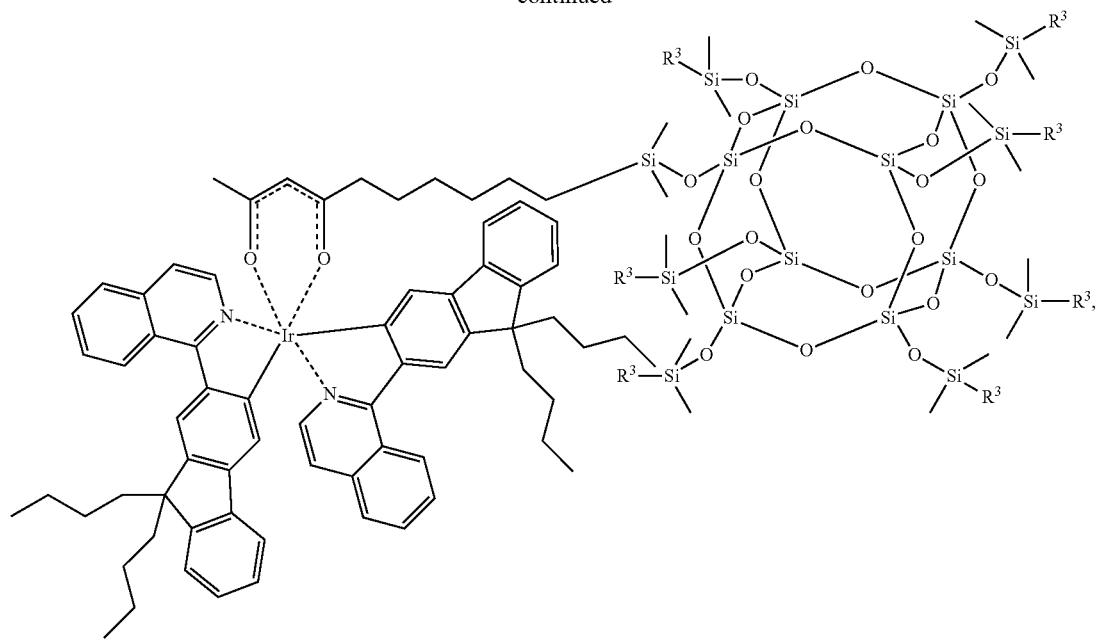
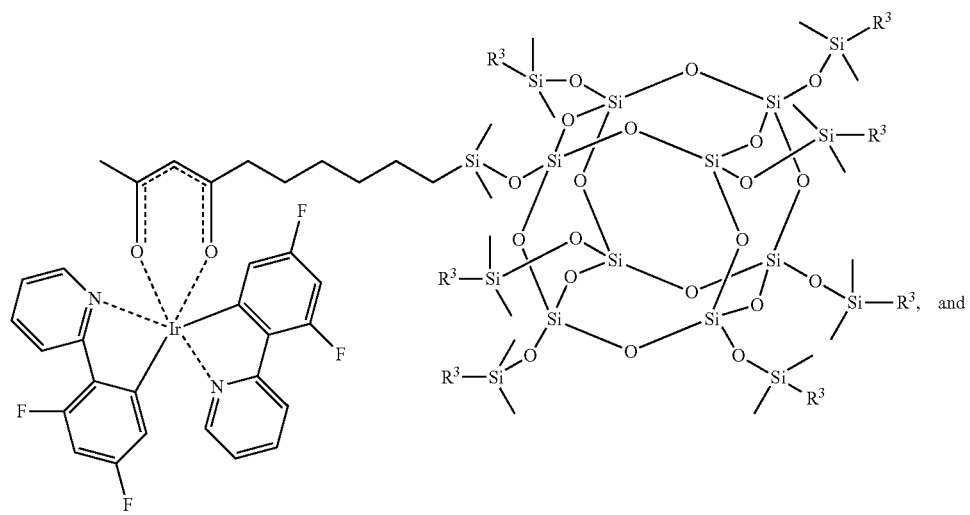
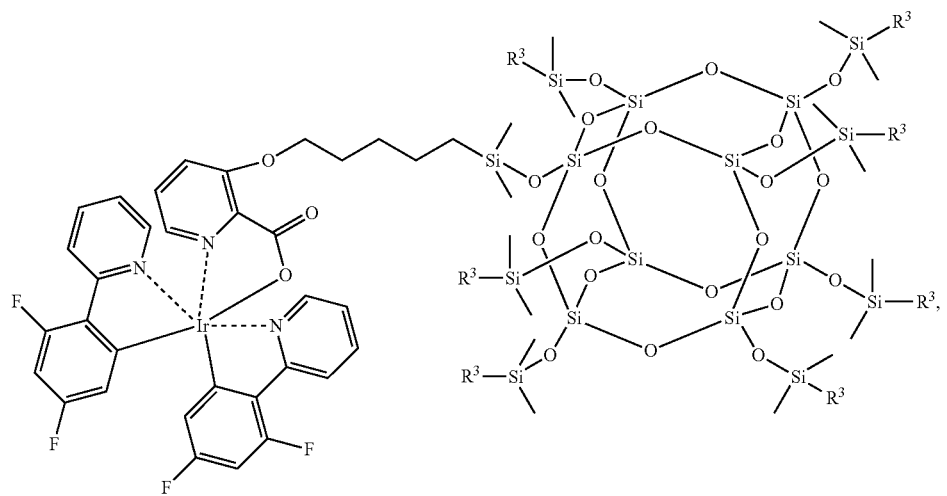

wherein R³ is the host having one of the following formulas
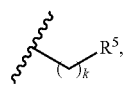
wherein k is 0 or an integer selected from 1 to 20, and R⁵ can be selected from the following:
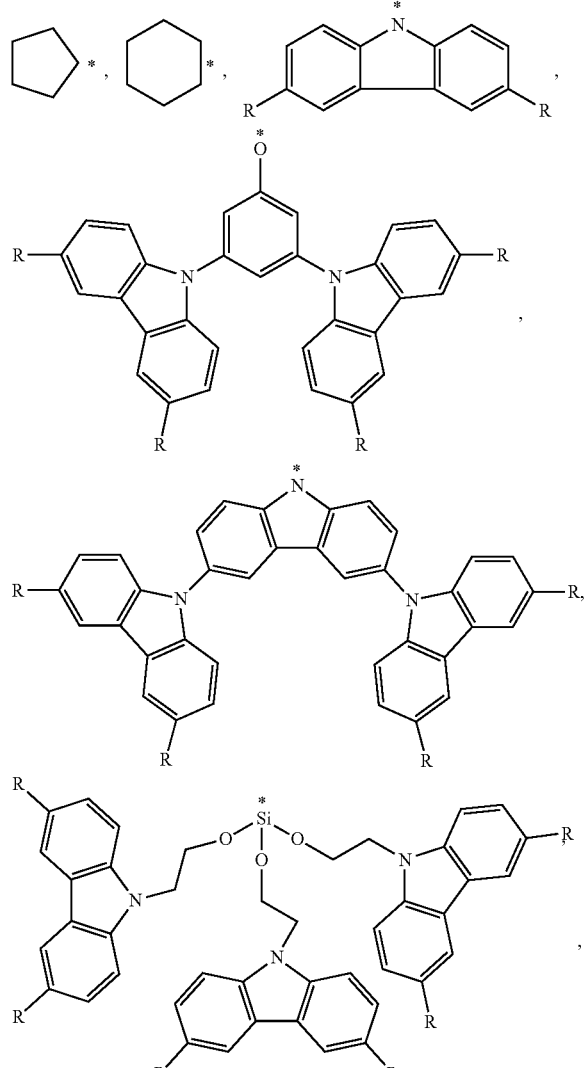
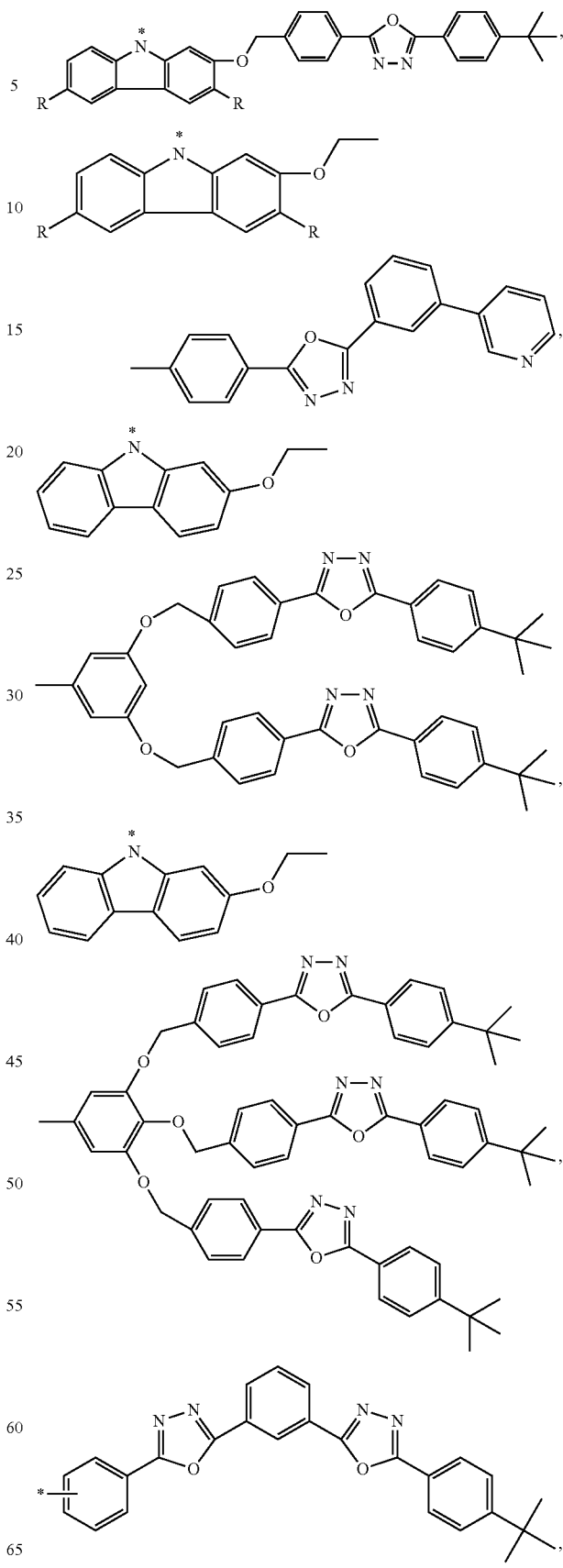

25
-continued

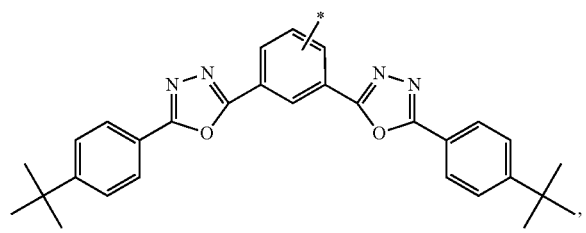

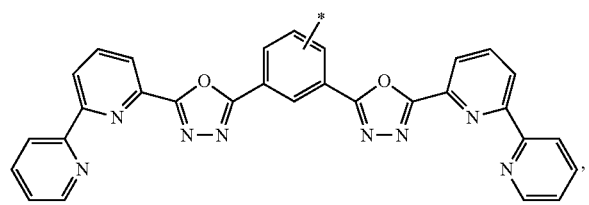

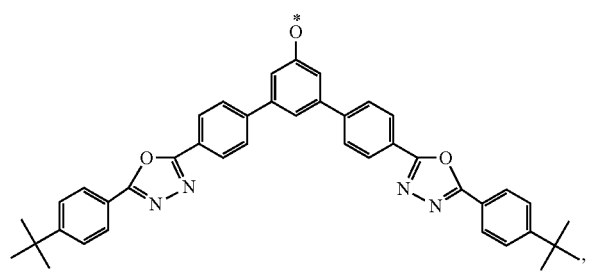

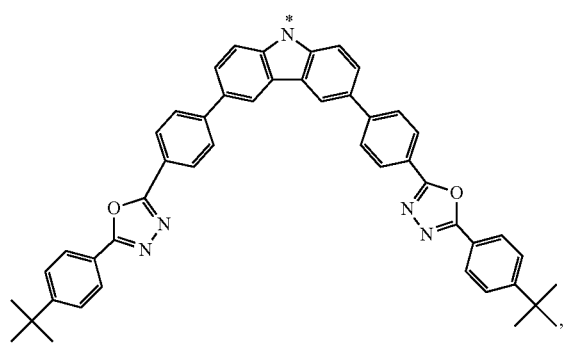

and

26
-continued

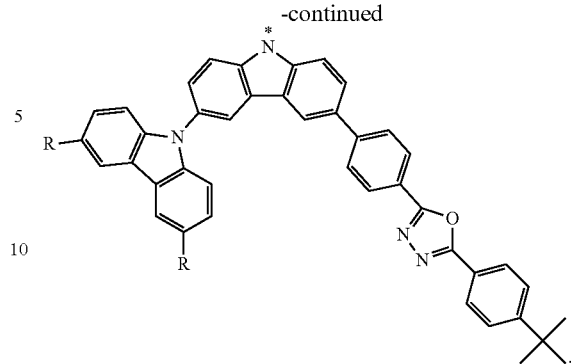

wherein R is independently selected from H or alkyl, and * indicates a point of attachment to the Si or the alkyl group in R³.

The iridium-functionalized nanoparticles can be prepared in various ways, e.g., by attaching the iridium-based complex to a nanoparticle core. A preferred method for making nanoparticles that emit light is illustrated herein. The covalent attachment of the iridium-complexes to the a silsesquioxane nanoparticle core is preferably carried out in the general manner as described herein and in PCT WO 02/05971, which is hereby incorporated by reference. A preferred nanoparticle core is a silsesquioxane as shown in Formula (II), more preferably a 1,3,5,7,9,11,13,15-octakis(dimethylsilyloxy)pentacyclo-[9.5.1.1$^{3,9}$.1$^{5,15}$.1$^{7,13}$]octasiloxane as shown in Formula (III), both formulas are shown above.

Light-emitting nanoparticles that emit various colors may be created by attaching one or more iridium-complexes to a nanoparticle core. An exemplary method for preparing the iridium-functionalized nanoparticles described herein is shown in Schemes 1a-c and 2a-d.

Scheme 1a

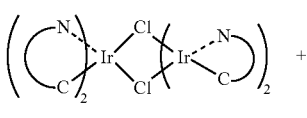

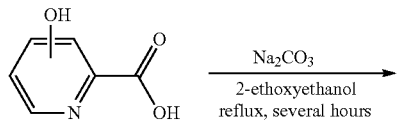

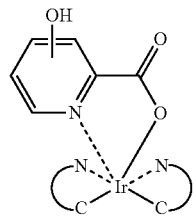

Scheme 1b
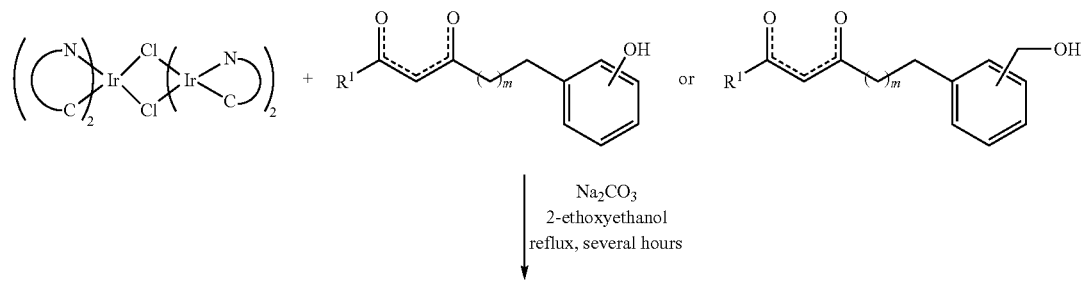
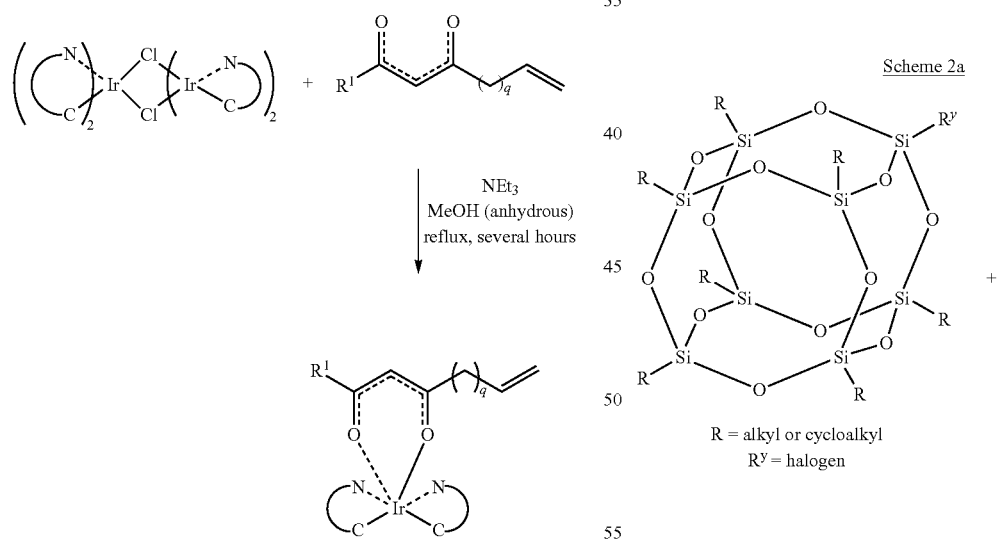
Scheme 1c
m, and $R^1$ are the same as described above, and q can be 0 or an integer in the range of 1 to 18.
Scheme 2a
R = alkyl or cycloalkyl
$R^y$ = halogen
In Schemes 1a, 1b and 1c,

-continued
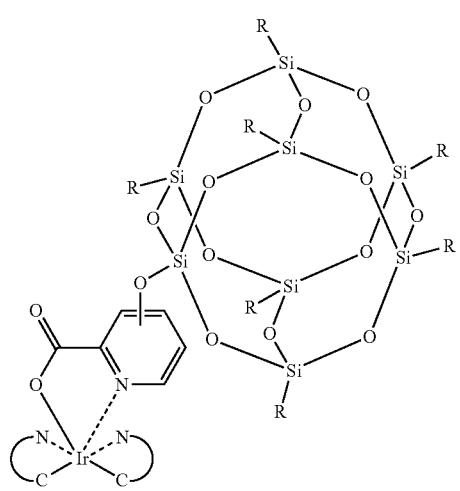
Scheme 2b
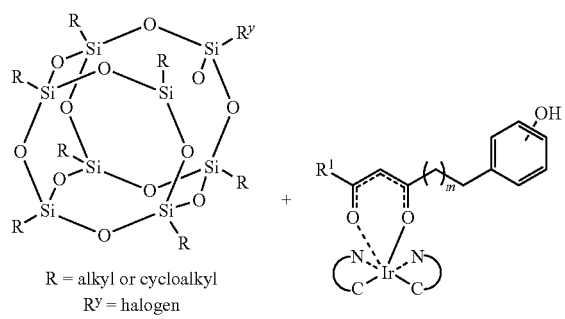
R = alkyl or cycloalkyl
R$^y$ = halogen
↓ base
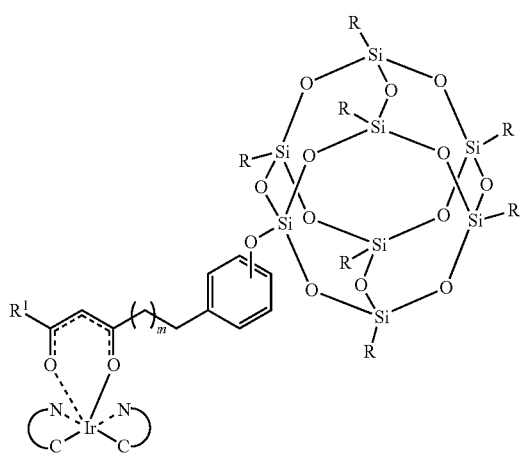
Scheme 2c
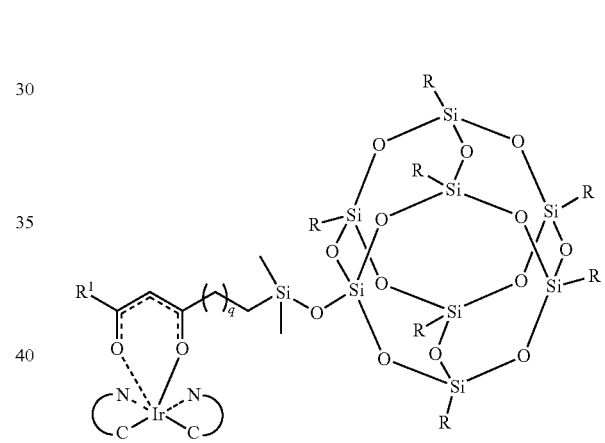
R = alkyl or cycloalkyl
R$^y$ = dimethylsilyloxy
[Pt] ↓ hydrosilylation
Scheme 2d
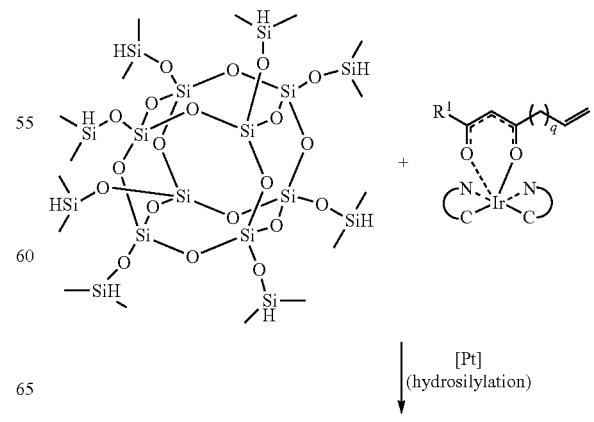
[Pt]
(hydrosilylation) ↓

31
-continued
32
-continued
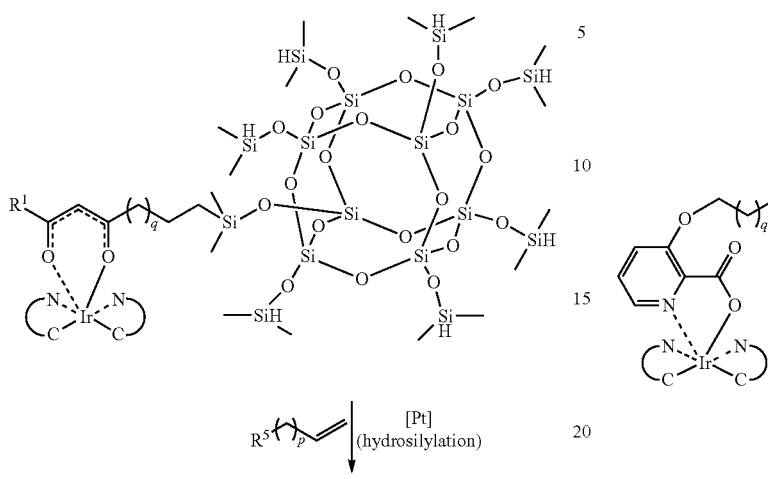
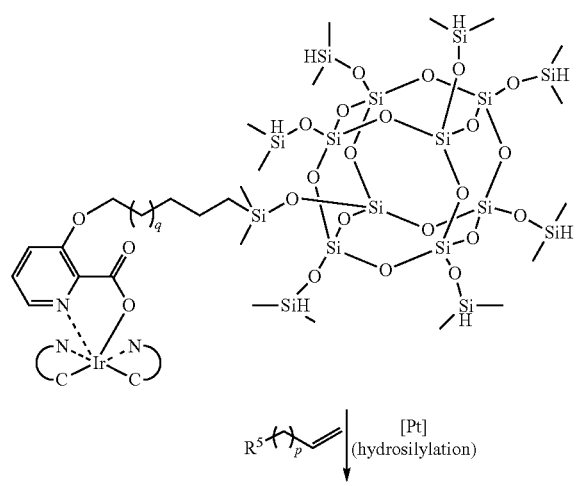
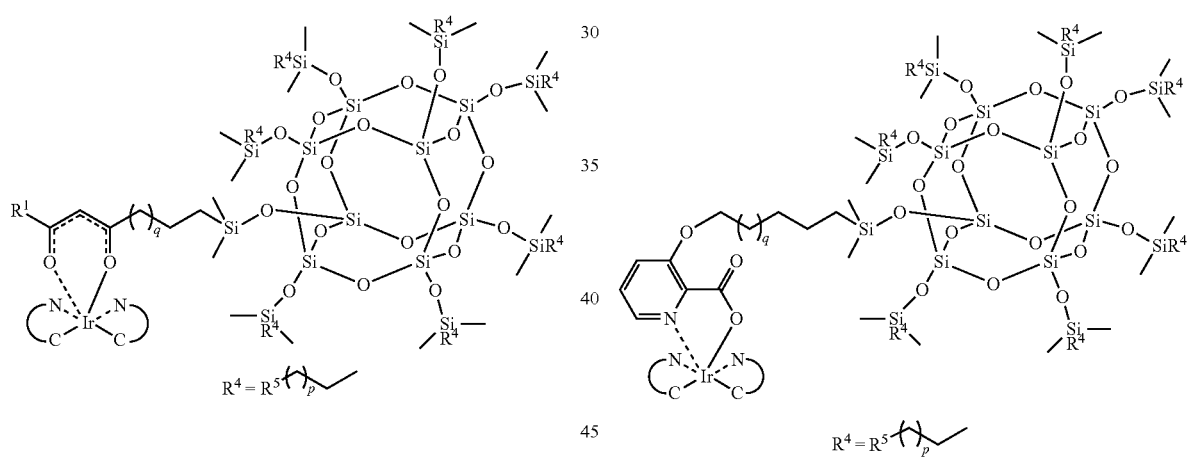
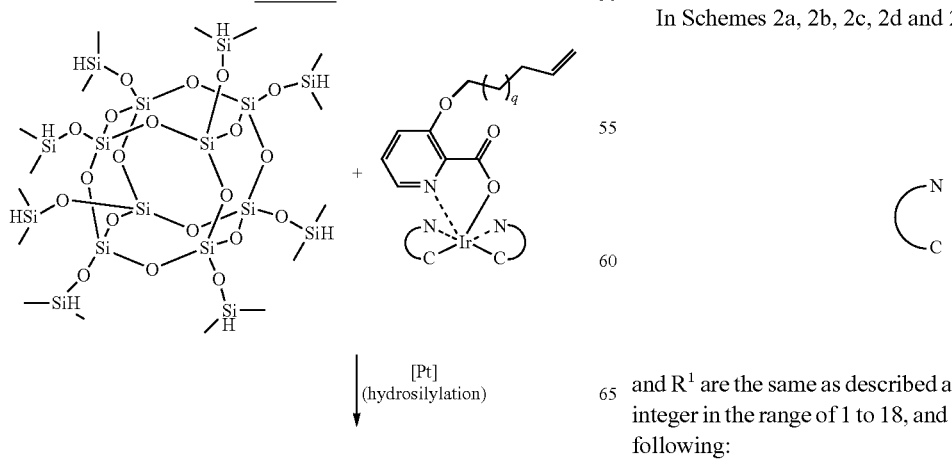
In Schemes 2a, 2b, 2c, 2d and 2e,
and $R^1$ are the same as described above, p and q can be 0 or an integer in the range of 1 to 18, and $R^5$ can be selected from the following:

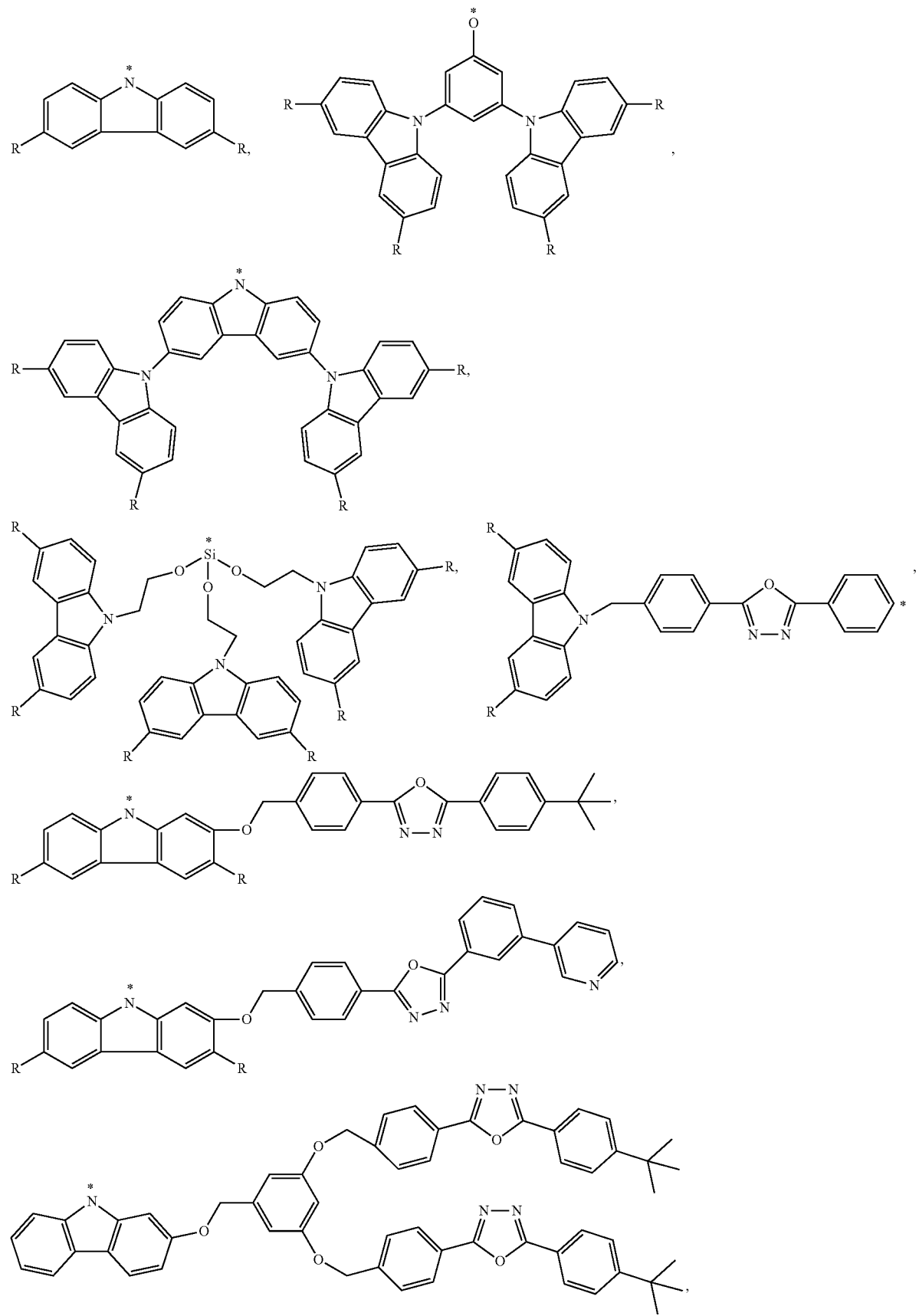

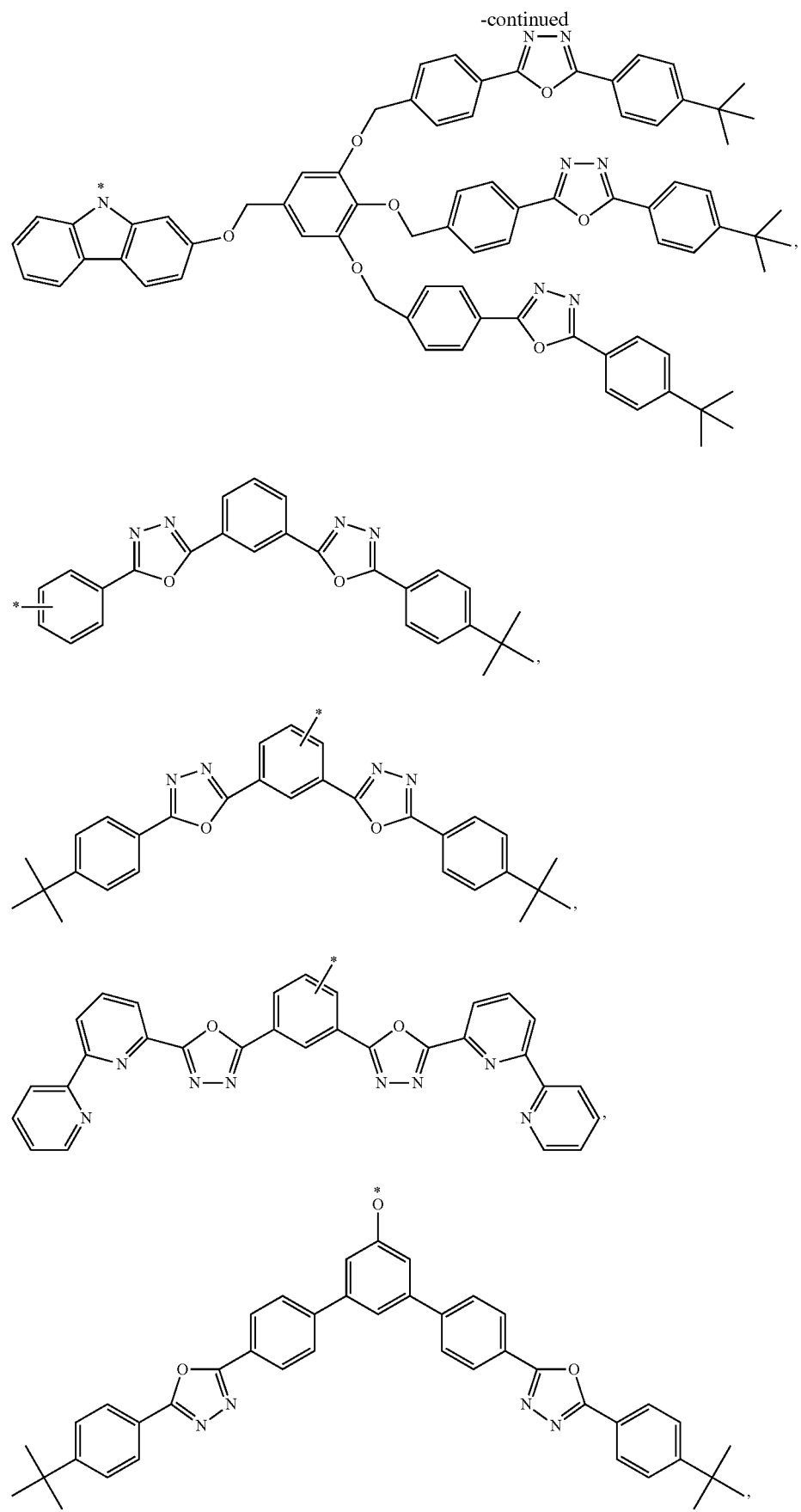

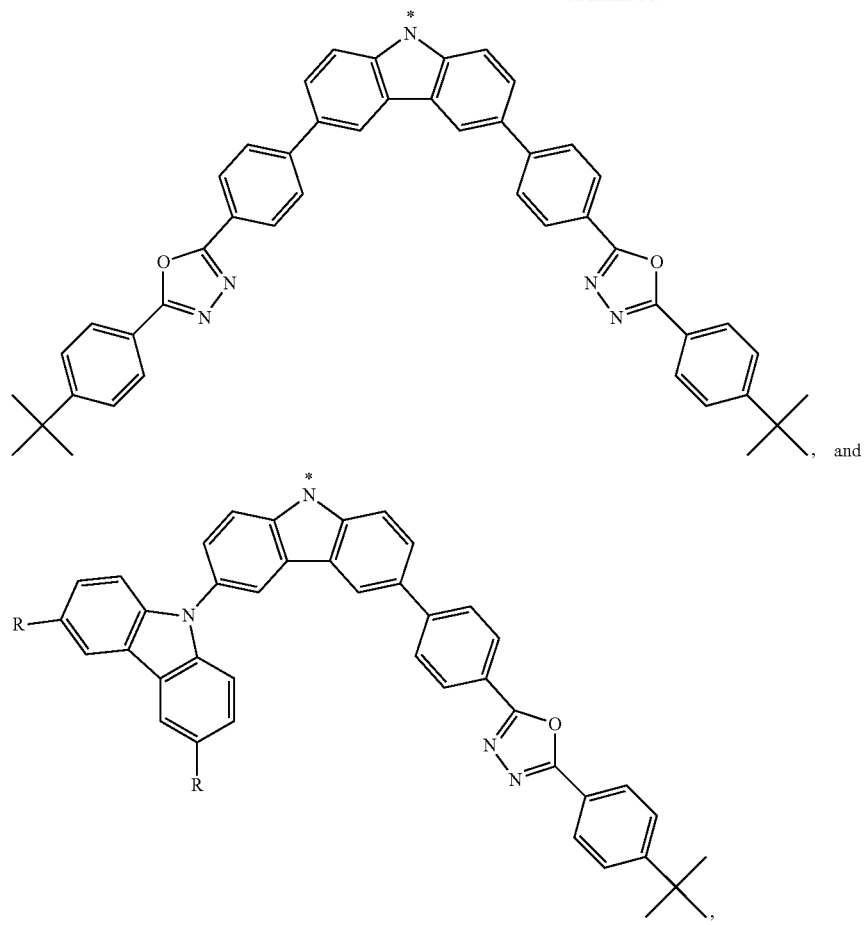

, and wherein R is independently selected from H or alkyl, and * indicates a point of attachment to the Si or the alkyl group in $R^4$. Suitable bases are known to those skilled in the art. In one embodiment, an exemplary base is imidazole. For the hydrosilylation reaction, suitable [Pt] catalysts are known to those skilled in the art. In one embodiment, an exemplary [Pt] catalyst is platinum divinyltetramethyldisiloxane (Pt(dvs)).

Iridium-functionalized nanoparticles may be configured to emit various colors, depending on the identities of the iridium complexes. The iridium complex is preferably selected so that the resulting iridium-functionalized nanoparticles emit the desired color, (e.g., white light). Those skilled in the art recognize that the color emitted by the iridium-functionalized nanoparticles can be tuned by the appropriate choice of the iridium complex In an embodiment, the nanoparticle core can be a single silsesquioxane with a silsesquioxane core represented by Formula (II). The silsesquioxane core shown in Formula (II) has a relatively stiff cubical structure and the iridium complexes, represented by R' groups in Formula (II), can be attached at the vertices of the silsesquioxane. Although this invention is not bound by any theory of operation, it is believed that linking the iridium-complex onto the exterior surface of the nanoparticle core with attached host material with a covalent bond rather than direct incorporation of iridium-complexes into the host may substantially reduce the interaction between iridium-complexes and thus prevent aggregation. As a result, the emission of light by the iridium-functionalized nanoparticles described herein is improved. In addition, it is believed that the silsesquioxane core lends some thermal stability to the light-emitting compositions described herein. In one embodiment, an exemplary iridium-functionalized nanoparticles with a silsesquioxane core is shown below:

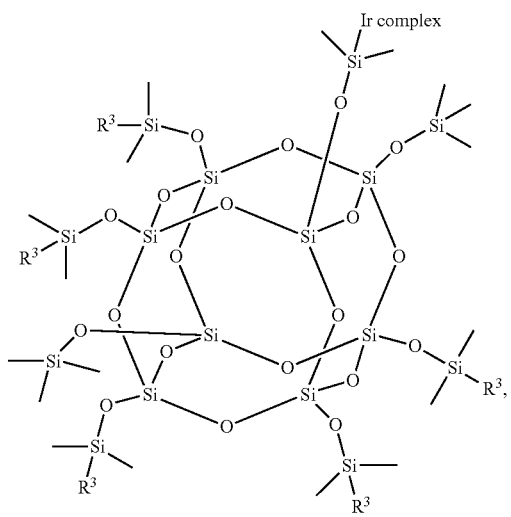

wherein "Ir complex" is an iridium-based complex and R³ is as defined above.

The iridium-functionalized nanoparticles described herein can be incorporated into light-emitting devices in various ways. For example, an embodiment provides a light-emitting device, comprising: an anode layer comprising a high work function metal; a cathode layer comprising a low work function metal; and a light-emitting layer positioned between, and electrically connected to, the anode layer and the cathode layer. The light-emitting layer comprises an iridium-functionalized nanoparticle or composition thereof, as described herein. For example, in an embodiment, the light-emitting layer comprises phosphorescent emitting-functionalized nanoparticles such as iridium-functionalized nanoparticles. In an embodiment, the iridium-functionalized nanoparticle is represented by Formula (I). In an embodiment, the iridium-functionalized nanoparticle is an organic-inorganic iridium-functionalized nanoparticle. In an embodiment, the organic-inorganic iridium-functionalized nanoparticle comprises a nanoparticle core that comprises inorganic elements such as phosphorous (P), silicon (Si), and/or a metal. For example, in an embodiment a nanoparticle core comprises a moiety selected from the group consisting of a silsesquioxane, a cyclophosphazene, a triazine, a cyclodextrin, a calizarene, a phthalocyanine, and a silica particle. The light-emitting compositions described herein can include one or more iridium-functionalized nanoparticles and/or other materials in addition to the iridium-functionalized nanoparticle(s).

An anode layer may comprise a conventional material such as a metal, mixed metal, alloy, metal oxide or mixed-metal oxide, or a conductive polymer. Examples of suitable metals include the Group 1 metals, the metals in Groups 4, 5, 6, and the Group 8-10 transition metals. If the anode layer is to be light-transmitting, mixed-metal oxides of Group 12, 13, and 14 metals or alloys thereof, such as Au, Pt, and indium-tin-oxide (ITO), may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In an embodiment, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and Li₂O may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In an embodiment, the cathode layer can have a thickness in the range of about 1 nm to about 1000 nm.

The amount of the iridium-functionalized nanoparticle(s) in the light-emitting composition can vary. In some embodiments, the amount of iridium-functionalized nanoparticles in the light-emitting composition layer can be in the range of from about 1% to about 100% by weight based on total weight of the light-emitting layer. In an embodiment, the amount of iridium-functionalized nanoparticles in the light-emitting layer can be in the range of from about 30% to about 70% by weight based on total weight of the light-emitting layer. In some embodiments, the amount of iridium-functionalized nanoparticles in the light-emitting layer can be in the range of from about 1% to about 10% by weight based on total weight of the light-emitting layer. In some embodiments, the light-emitting layer can have a thickness in the range of about 20 nm to about 150 nm.

In some embodiments, the light-emitting layer can further include a host material. Exemplary host materials are known to those skilled in the art. For example, the host material included in the light-emitting layer can be an optionally substituted compound selected from: an aromatic-substituted amine, an aromatic-substituted phosphine, a thiophene, an oxadiazole, 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), a triazole, 3-phenyl-4-(1'-naphthyl)-5-phenyl-1,2,4-triazole (TAZ), 3,4,5-Triphenyl-1,2,3-triazole, 3,5-Bis(4-tert-butyl-phenyl)-4-phenyl[1,2,4]triazole, an aromatic phenanthroline, 2,9-dimethyl-4,7-diphenyl-phenanthroline (bathocuproine or BCP), 2,9-Dimethyl-4,7-diphenyl-1,10-phenanthroline, a benzoxazole, a benzothiazole, a quinoline, aluminum tris(8-hydroxyquinolate) (Alq3), a pyridine, a dicyanoimidazole, cyano-substituted aromatic, 1,3,5-tris(2-N-phenylbenzimidazolyl)benzene (TPBI), 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4'-bis[N,N'-(3-tolyl)amino]-3,3'-dimethylbiphenyl (HMTPD), 1,1-Bis(4-bis(4-methylphenyl)aminophenyl)cyclohexane, a carbazole, 4,4'-N,N'-dicarbazole-biphenyl (CBP), poly(9-vinylcarbazole) (PVK), N,N'N''-1,3,5-tricarbazoloylbenzene (tCP), a polythiophene, a benzidine, N,N'-bis(4-butylphenyl)-N,N'-bis(phenyl)benzidine, a triphenylamine, 4,4',4''-Tris(N-(naphthylen-2-yl)-N-phenylamino)triphenylamine, 4,4',4''-tris(3-methylphenylphenylamino)triphenylamine (MTDATA), a phenylenediamine, a polyacetylene, and a phthalocyanine metal complex.

It is understood to those skilled in the art that the groups described above as possible hosts can function as hole-transport materials or electron-transport materials. Exemplary hole-transport materials include 4,4'-bis[N-(naphthyl)-N-phenyl-amino]biphenyl (α-NPD), N,N'-bis(3-methylphenyl) N,N'-diphenyl-[1,1'-biphenyl]-4,4'-diamine (TPD), 4,4'-bis[N,N'-(3-tolyl)amino]-3,3'-dimethylbiphenyl (M14), 4,4',4''-tris(3-methylphenylphenylamino)triphenylamine (MTDATA), 4,4'-bis[N,N'-(3-tolyl)amino]-3,3'-dimethylbiphenyl (HMTPD), N,N'N''-1,3,5-tricarbazoloylbenzene (tCP), 4,4'-N,N'-dicarbazole-biphenyl (CBP), poly(9-vinylcarbazole) (PVK), 3,4,5-Triphenyl-1,2,3-triazole, 3,5-Bis(4-tert-butyl-phenyl)-4-phenyl[1,2,4]triazole, 2,9-Dimethyl-4,7-diphenyl-1,10-phenanthroline, 1,1-Bis(4-bis(4-methylphenyl)aminophenyl)cyclohexane, N,N'-bis(4-butylphenyl)-N,N'-bis(phenyl)benzidine, 4,4',4''-Tris(N-(naphthylen-2-yl)-N-phenylamino)triphenylamine, and copper phthalocyanine. Examples of electron-transport materials include aluminum tris(8-hydroxyquinolate) (Alq3), 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), 3-phenyl-4-(1'-naphthyl)-5-phenyl-1,2,4-triazole (TAZ), 2,9-dimethyl-4,7-diphenyl-phenanthroline (bathocuproine or BCP), and 1,3,5-tris[2-N-phenylbenzimidazol-z-yl]benzene (TPBI).

If desired, additional layers may be included in the light-emitting device. Additional layers that may be included include an electron injection layer (EIL), electron transport layer (ETL), hole blocking layer (HBL), exciton blocking layer (EBL), hole transport layer (HTL), and/or hole injection layer (HIL). In an embodiment, the light-emitting device can include an electron injection layer e.g., between the cathode layer and the light emitting layer. The lowest un-occupied molecular orbital (LUMO) energy level of the material(s) that can be included in the electron injection layer is preferably high enough to prevent it from receiving an electron from the light emitting layer. The energy difference between the LUMO of the material(s) that can be included in the electron injection layer and the work function of the cathode layer is preferably small enough to allow efficient electron injection from the cathode. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tert-butylphenyl)-1, 3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc.

Some embodiments described herein can include an electron transport layer positioned between the cathode and light-emitting layer. Suitable electron transport materials are known to those skilled in the art. Exemplary electron transport materials that can be included in the electron transport layer are an optionally substituted compound selected from: aluminum tris(8-hydroxyquinolate) (Alq3), 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), 3-phenyl-4-(1'-naphthyl)-5-phenyl-1,2,4-triazole (TAZ), 2,9-dimethyl-4,7-diphenyl-phenanthroline (bathocuproine or BCP), and 1,3,5-tris[2-N-phenylbenzimidazol-z-yl]benzene (TPBI).

In another embodiment, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1, 2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In still another embodiment, the light-emitting device can include an exciton blocking layer, e.g., between the light-emitting layer and the anode. The band gap of the material(s) that comprise exciton blocking layer is preferably large enough to substantially prevent the diffusion of excitons. A number of suitable exciton blocking materials that can be included in the exciton blocking layer are known to those skilled in the art. Examples of material(s) that can compose an exciton blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In yet still another embodiment, the light-emitting device can include a hole transport layer, e.g., between the light-emitting layer and the anode. Suitable hole transport materials that can be included in the hole transport layer are known those skilled in the art. For example, hole transport material(s) that can be included in the hole transport layer are 4,4'-bis[N-(naphthyl)-N-phenyl-amino]biphenyl (α-NPD), N,N'-bis(3-methylphenyl)N,N'-diphenyl-[1,1'-biphenyl]-4, 4'-diamine (TPD), 4,4'-bis[N,N'-(3-tolyl)amino]-3,3'-dimethylbiphenyl (M14), 4,4',4'-tris(3-methylphenylphenylamino)triphenylamine (MTDATA), 4,4'-bis[N,N'-(3-tolyl) amino]-3,3'-dimethylbiphenyl (HMTPD), N,N'N"-1,3,5-tricarbazoloylbenzene (tCP), 4,4'-N,N'-dicarbazole-biphenyl (CBP), poly(9-vinylcarbazole) (PVK), 3,4,5-Triphenyl-1,2, 3-triazole, 3,5-Bis(4-tert-butyl-phenyl)-4-phenyl[1,2,4]triazole, 2,9-Dimethyl-4,7-diphenyl-1,10-phenanthroline, 1,1-Bis(4-bis(4-methylphenyl)aminophenyl)cyclohexane, a carbazole, a polythiophene, a benzidine, N,N'-bis(4-butylphenyl)-N,N'-bis(phenyl)benzidine, a triphenylamine, a phenylenediamine, 4,4',4"-Tris(N-(naphthylen-2-yl)-N-phenylamino)triphenylamine, an oxadiazole, a polyacetylene and a phthalocyanine metal complex.

In an embodiment, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), or a phthalocyanine metal complex derivative such as phthalocyanine copper. Hole-injection materials while still being able to transport holes are distinguished from conventional hole-transport materials in that hole injection materials have a hole mobility substantially less than the hole mobility of conventional hole transport materials.

Those skilled in the art recognize that the various materials described above can be incorporated in several different layers depending on the configuration of the device. Preferably, the materials used in each layer are selected to result in the recombination of the holes and electrons in the light-emitting layer. An example of a device configuration that incorporates the various layers described herein is illustrated schematically in FIG. 1. The electron injection layer (EIL), electron transport layer (ETL), hole blocking layer (HBL), exciton blocking layer (EBL), hole transport layer (HTL), and hole injection layer (HIL) can be added to the light-emitting device using methods known to those skilled in the art (e.g., vapor deposition).

Light-emitting devices comprising iridium-functionalized nanoparticles can be fabricated using techniques known in the art, as informed by the guidance provided herein. For example, a glass substrate can be coated with a high work functioning metal such as ITO which can act as an anode. After patterning the anode layer, a light-emitting composition layer that includes the iridium-functionalized nanoparticles can be deposited on the anode. The cathode layer, comprising a low work functioning metal (e.g., Mg:Ag), can then be vapor evaporated onto the light-emitting composition layer. If desired, the device can also include an electron transport/injection layer, a hole blocking layer, a hole injection layer, an exciton blocking layer and/or a second light-emitting layer that can be added to the device using techniques known in the art, as informed by the guidance provided herein. In a preferred embodiment, an advantage of the light-emitting compositions described herein is that their molecular weights are large enough to allow for spray, dip, printing, and/or spray coating. Thus, the lighting-emitting device can be produced without having to employ complicated and expensive multilayer vapor deposition. Furthermore, in another preferred embodiment, the iridium-functionalized nanoparticles described herein can be easily spun off onto a hard or flexible substrate. As a result, the manufacture of the OLED device becomes much easier.

The light emitting devices described herein can be configured to emit various colors of light. In an embodiment, two or more iridium-functionalized nanoparticles can be combined in different ratios to produce a color of light. In another embodiment, one or more iridium-functionalized nanoparticles can be combined with one or more light emitting compounds to produce a color of light. For example, blue emitting iridium-functionalized nanoparticles and orange emitting compound(s) (e.g., orange iridium-functionalized nanoparticles) can be placed in the light-emitting layer to produce white light. In some of the embodiments described herein the light-emitting composition is configured to emit light such as blue, green, orange, red and white.

In some embodiments, lumophore-functionalized nanoparticles may be configured to emit various colors, depending on the identities of the lumophores and host groups. The relative ratio of host groups to lumophores are selected so as to have a high level of energy transfer from the host(s) to the lumophore(s) and/or so that light is emitted when energy is transferred to the lumophore(s) from the host(s). White light can be obtained by the appropriate choice of lumophores and/or hosts, and/or the relative ratios of host groups to lumophores. In another embodiment, the chosen lumophores have Commission Internationale de L'Eclairage (CIE) color coordinates that lie on a line which substantially intersects the achromatic point.

Without being bound by any particular theory or operation, it is believed that the incorporation of hole-transport or electron-transport moieties onto the nanoparticle core as hosts can increase the charge mobility, and/or balance the hole-transport or electron-transport inside the device. The direct attachment of the host to the nanoparticle core can further improve the compatibility between hole-transport or electron-transport moieties (i.e., host) and emissive dopant (i.e., Ir complex) or reduce the possibility of phase separation.

In some embodiments, exemplary lumophore-functionalized nanoparticles with a silsesquioxane core are shown below:

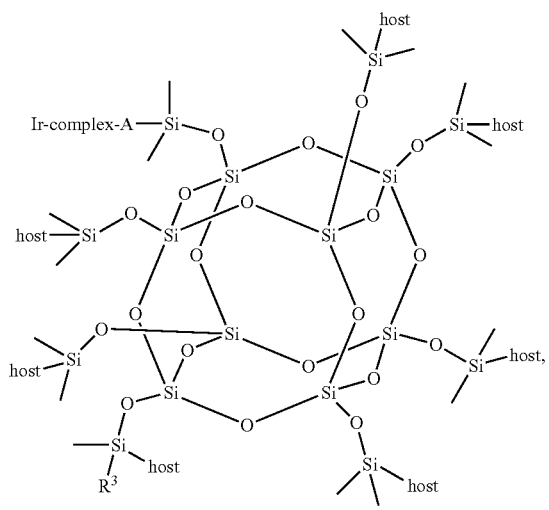

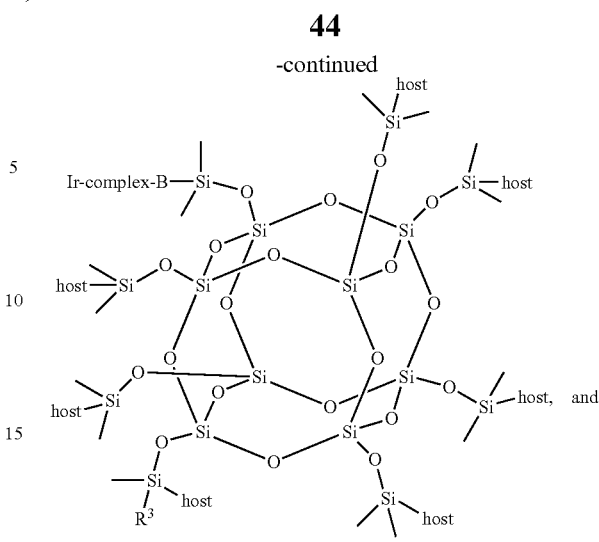

and

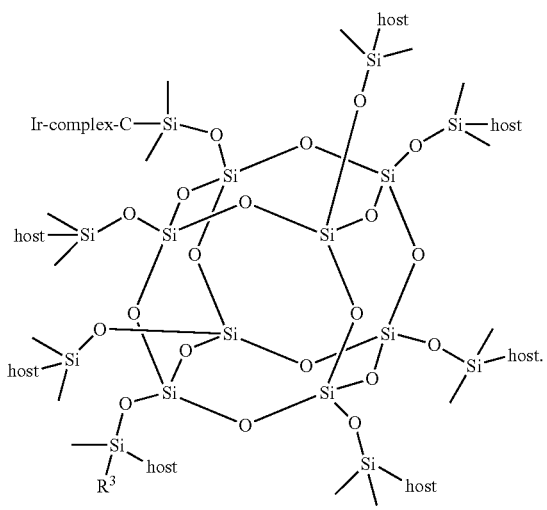

The Ir-complex-A, Ir-complex-B and Ir-complex-C represent three different Ir-complexes that can be any of the Ir-complexes described above. The "host" is also the same as defined above. By mixing different ratio of the three red-green-blue host/lumophore-functionalized nanoparticles, one embodiment of light-emitting device may emit white or near white light.

An embodiment provides a light-emitting composition that includes a mixture of different host/lumophore-functionalized nanoparticles. In some embodiments, the light-emitting composition may comprise one or more compound of formula (I) as defined above. In some embodiments, the light emitting composition may be a mixture of two or more compounds selected from the following group:

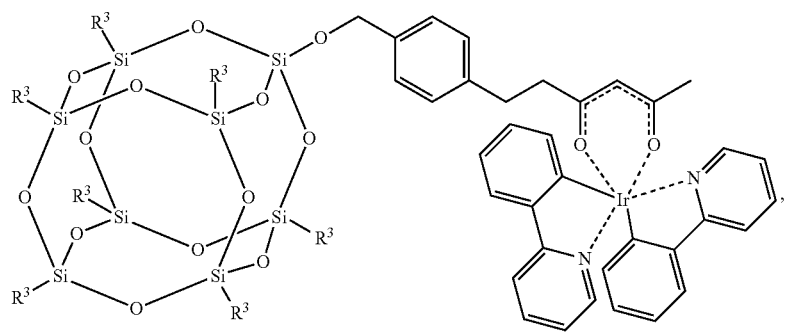
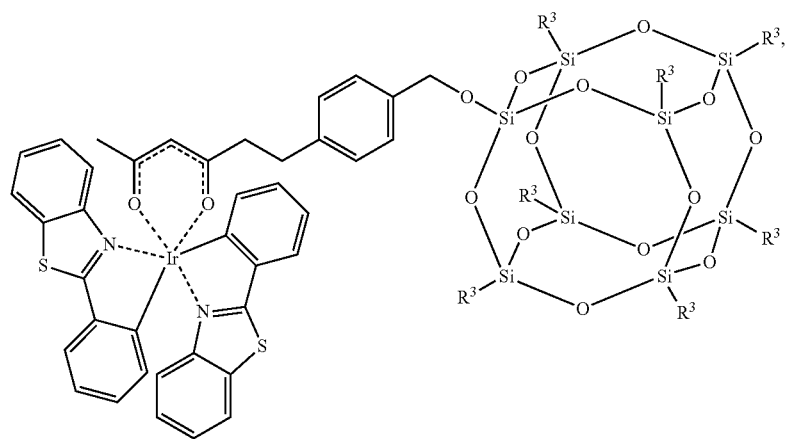
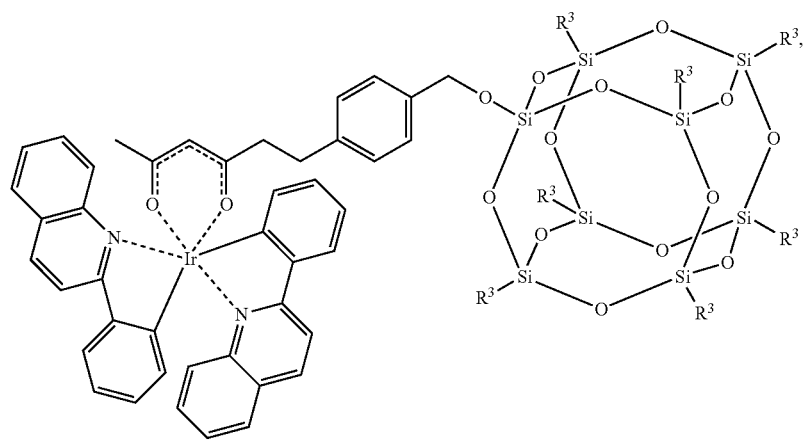
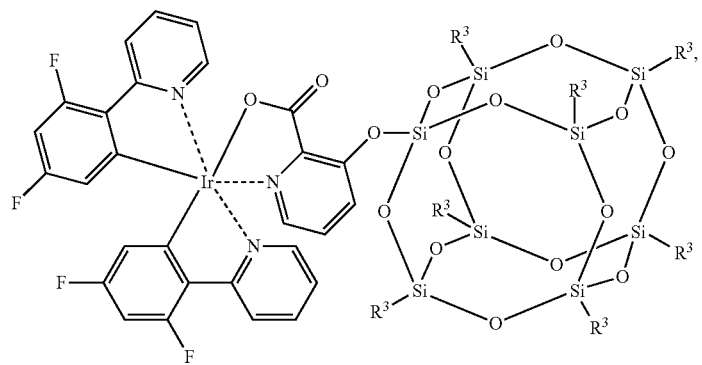

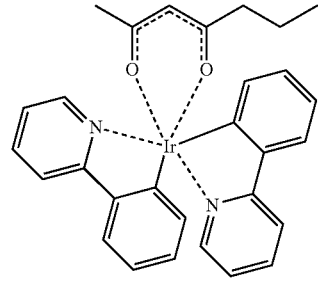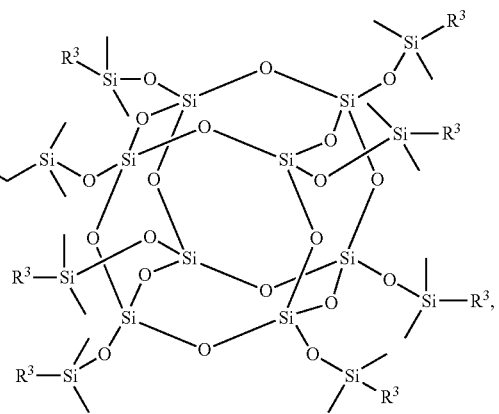
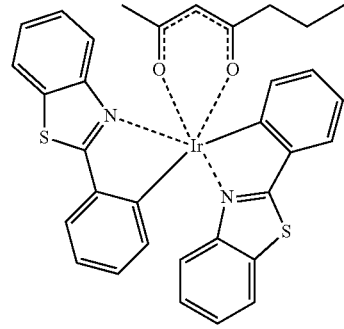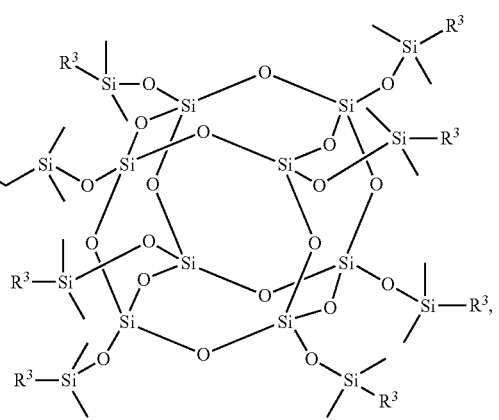
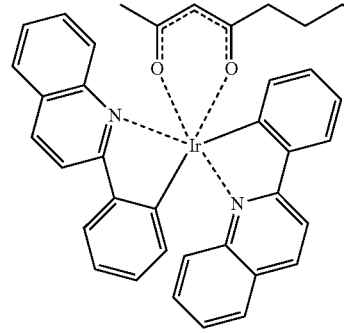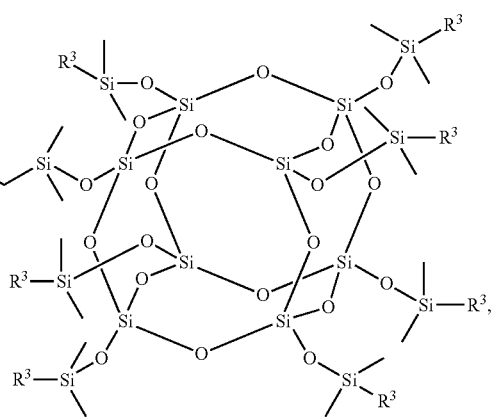

-continued
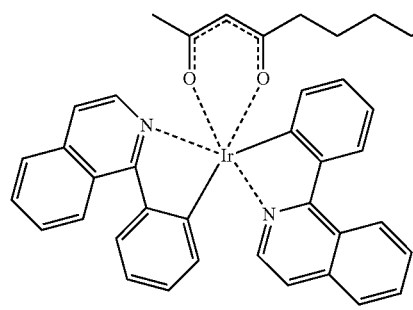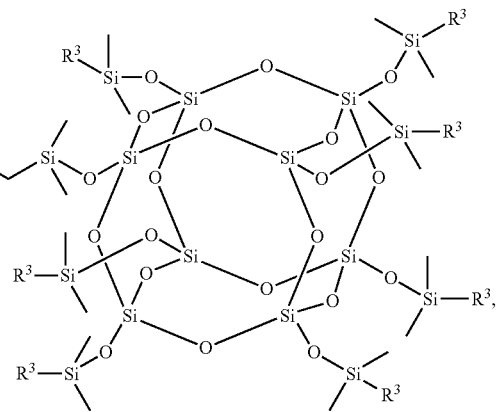
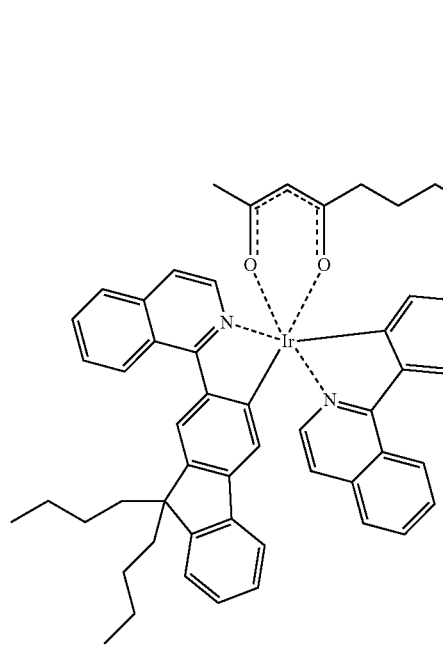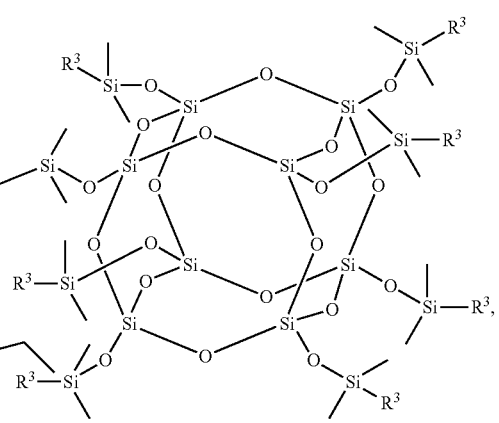
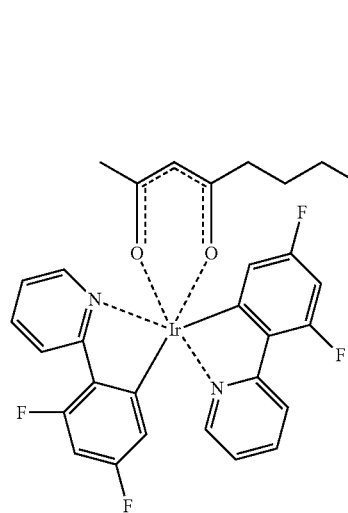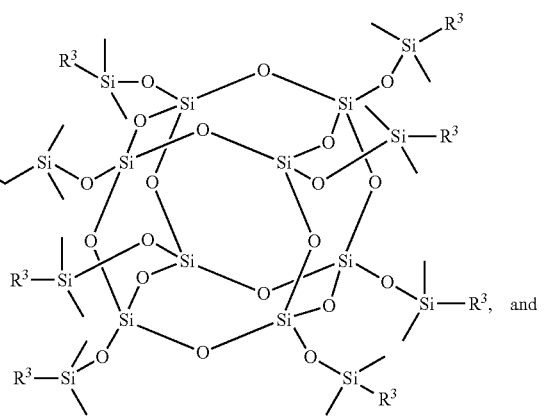

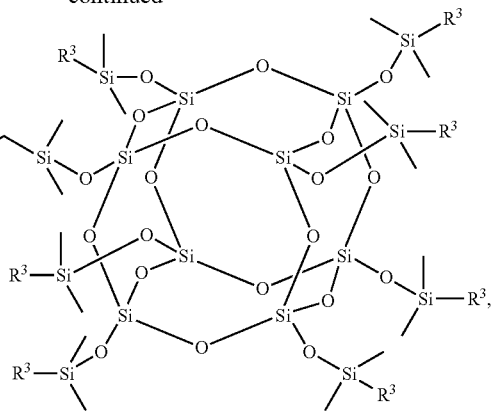
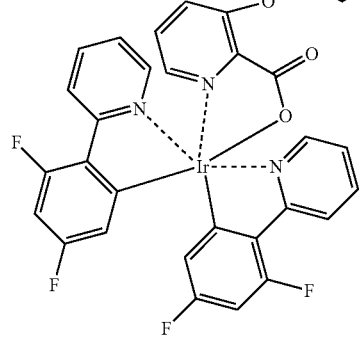
wherein R³ is the host having the formula
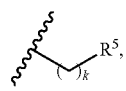
wherein k is 0 or an integer selected from 1 to 20 and R⁵ can be selected from the following:
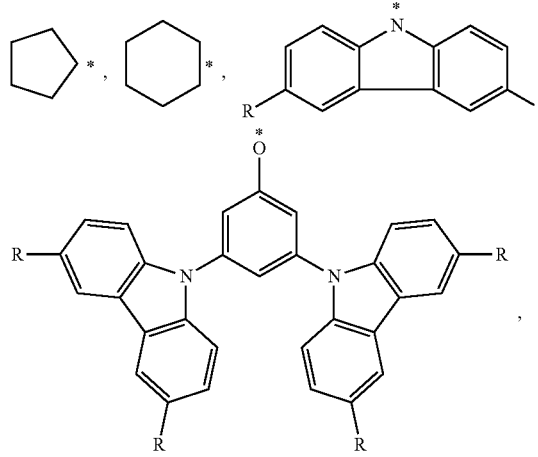
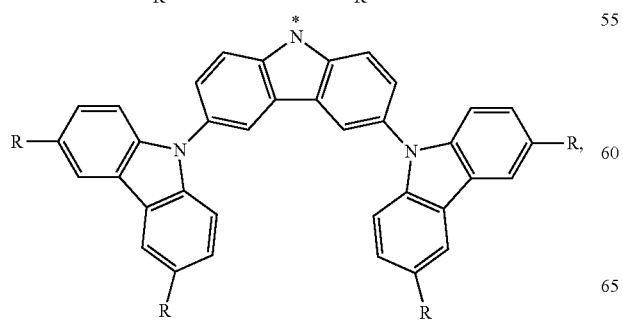
-continued
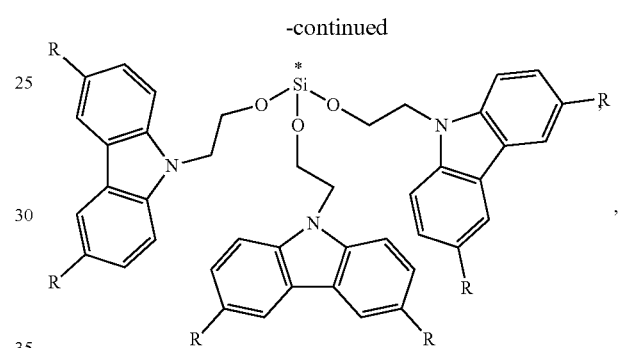
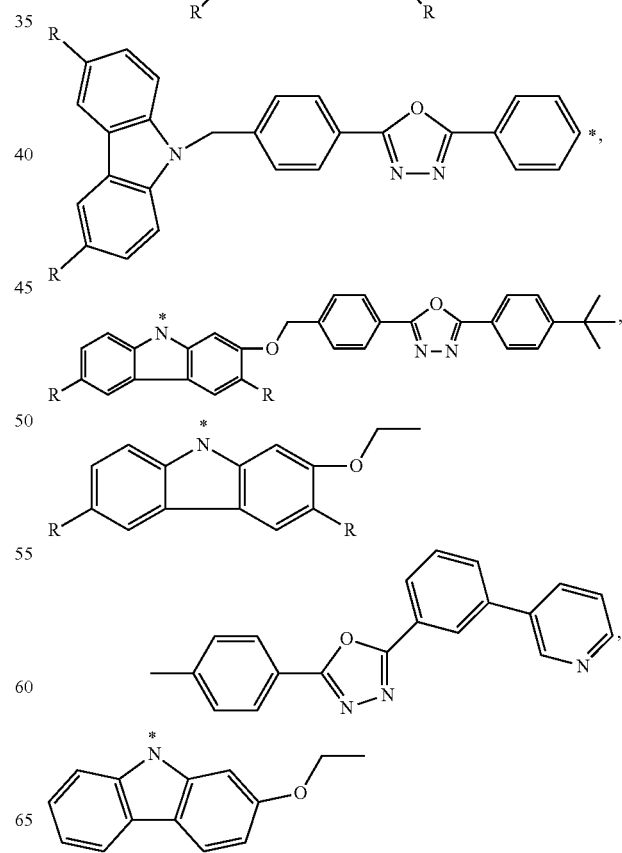

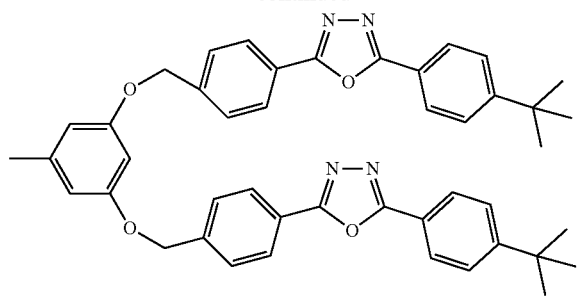

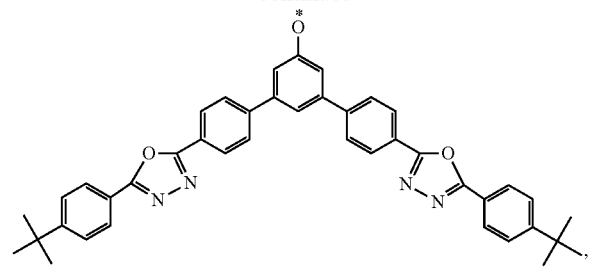

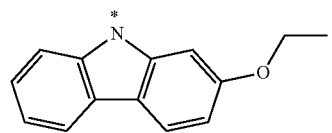

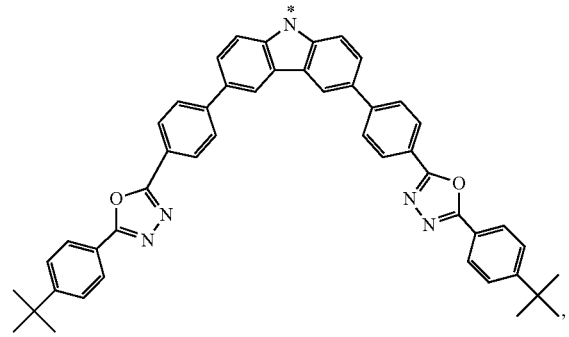

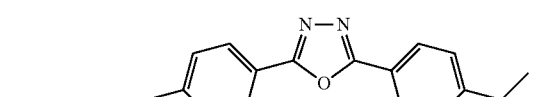

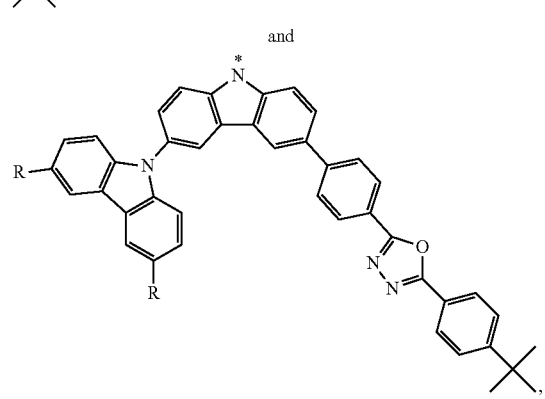

and

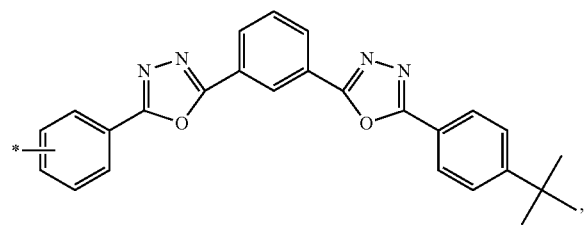

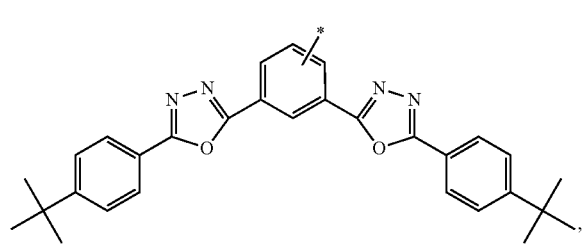

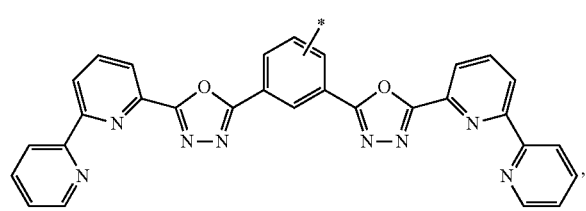

wherein R is independently selected from H or alkyl, and * indicates a point of attachment to the Si or the alkyl group in $R^3$.

In some embodiments, the identities of the lumophores and the relative ratio of lumophores to host groups can be selected to as to have a CRI value in the range of about 60 to about 100, about 80 to about 100, or greater than 70.

EXAMPLES

Representative embodiments of the invention will now be described, including how such embodiments may be made. It is understood that the methods, materials, conditions, process parameters, apparatus and the like do not necessarily limit the scope of the invention.

All chemicals, solvents, and reagents were purchased from Aldrich and ACROS ORGANICS and used without further purification. All procedures involving $IrCl_3 \cdot H_2O$ or any other Ir(III) species were carried out in inert gas atmosphere despite the air stability of the compounds, the main concern being their oxidative stability and stability of intermediate complexes at high temperature. $^1H$ and $^{13}C$ NMR data were measured at room temperature on a 400 MHz (100 MHz for $^{13}C\{1H\}$) in $CDCl_3$ or $(CD_3)_2CO$. UV-vis spectra were recorded on a Perkin-Elmer UV-vis Lambda spectrometer and were recorded as solution in spectroscopic grade chloroform or dichloromethane. Mass spectra were recorded on a Brummer Daltonics microflex LT. Melting and decomposition temperatures were measured on a Perkin-Elmer differential scanning calorimeter Pyris 1.

Example 1

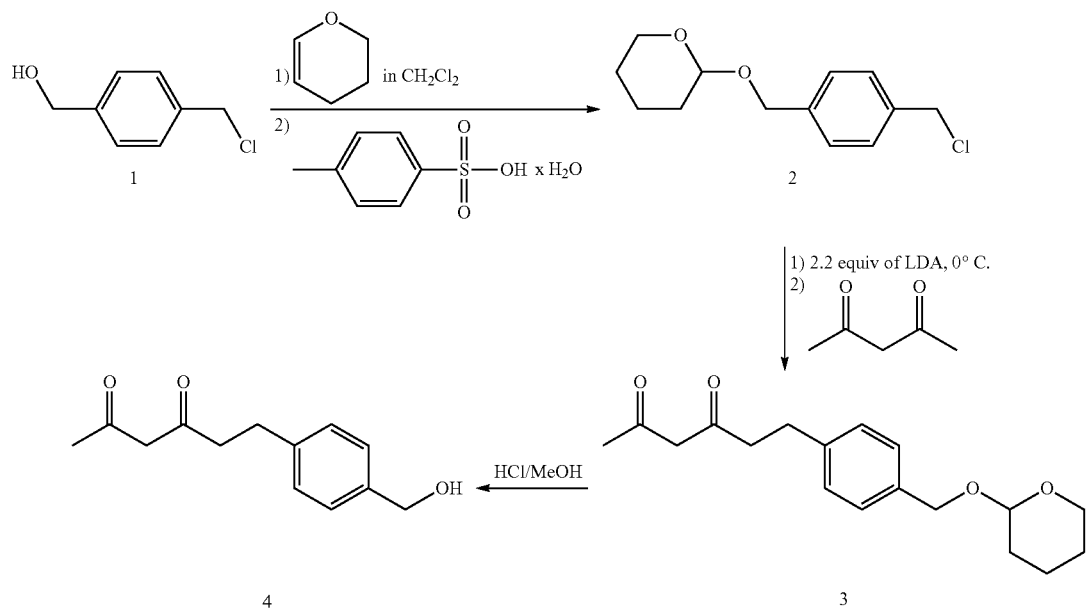

Synthetic Procedure of 2:

4-(chloromethyl)benzyl alcohol 1 (5 g, 32 mmol), 3,4-Dihydro-2H-pyran (2.69 g, 32 mmol) and p-Toluenesulfonic acid monohydrate (60 mg, 0.32 mmol) were dissolved in 60 mL of anhydrous dichloromethane. The mixture was stirred for 3 h under argon at room temperature. After which, the crude mixture was extracted with dichloromethane and washed three times with water (50 mL×3), brine (50 mL), and dried over anhydrous magnesium sulfate, $MgSO_4$. The organic solvent was then evaporated under reduced pressure. The crude product was eluted with 1:4 ratios ($R_f$=0.63) of ethyl acetate and hexane by flash chromatograph, and gave 6.15 g (80%) 2 as a colorless oil.

Synthetic Procedure of 3:

Acetylacetone (2 g, 20 mmol) was reacted with 2.2 equiv of 1.8 M of LDA (24 mL, 44 mmol) in anhydrous THF at 0° C. in ice/water bath. The reaction mixture was stirred for 20 min at 0° C. followed by slow addition of 2 (3.05 g, 20 mmol). The reaction mixture was then stirred for another 20 min at 0° C. and then was quenched with 1M of HCl (aq). The organic solvent was completely evaporated by rotary evaporator and the residue was dissolved in dichloromethane. The organic layer was washed three times (3×50 mL) with water and brine, dried over $MgSO_4$. The crude product was further purified by a silica gel chromatography with a 1:4 ratio ($R_f$=0.45) of ethyl acetate and hexane, and gave 1.35 g (31% yield) 3 as a pale yellow oil.

Synthetic Procedure of 4:

3 (1.06 g, 3.48 mmol) was dissolved in methanol (20 mL) and was mixed with 0.5 mL of conc. HCl (aq). The mixture was stirred for 2 h at room temperature. The methanol was removed by rotary evaporator and the residue was dissolved in ethyl acetate. The organic layer was washed with water, brine, and dried over $MgSO_4$. The crude mixture was further purified by a silica-gel chromatography with a 1:1 ratio ($R_f$=0.65) of ethyl acetate and hexane, and gave 0.72 g (94%) 4 as a purified product.

Example 2

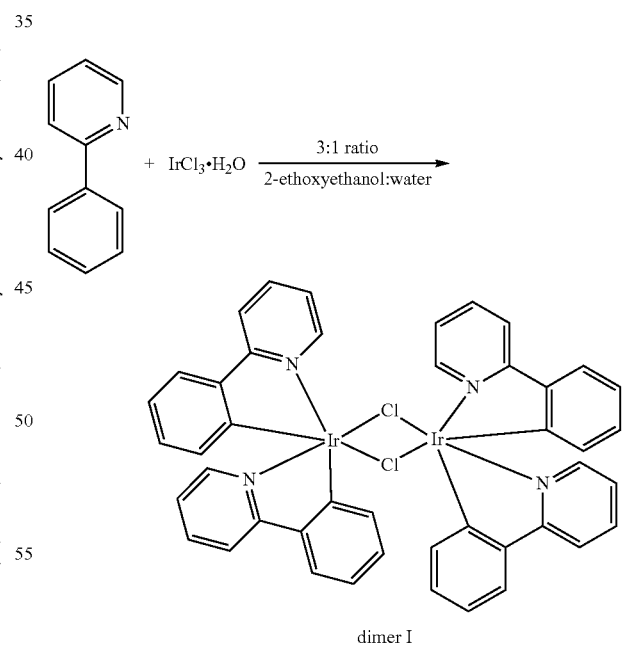

dimer I

Synthetic Procedure of Dimer I, $[Ir(\mu-Cl)(ppy)_2]_2$:

Dimer I was synthesized in accordance with the procedures described in *J. Am. Chem. Soc.*, 1984, 106, 6647 and *Bull. Chem. Soc. Jpn.*, 1974, 47, 767, which are both hereby incorporated by reference in their entireties. Iridium trichloride hydrate (1 mmol) was combined with 2-phenylpyridine (4.46 mmol) dissolved in a mixture of 2-ethoxyethanol and water (3/1). The mixture was refluxed for 24 h. The solution was then cooled to room temperature, and the yellow precipitate was washed with 95% ethanol and acetone. The yellow precipitate was then dissolved in dichloromethane and filtered. Toluene and hexane were added to the filtrate, which was then reduced in volume by evaporation. After cooling, crystals of dimer I was obtained.

Example 3

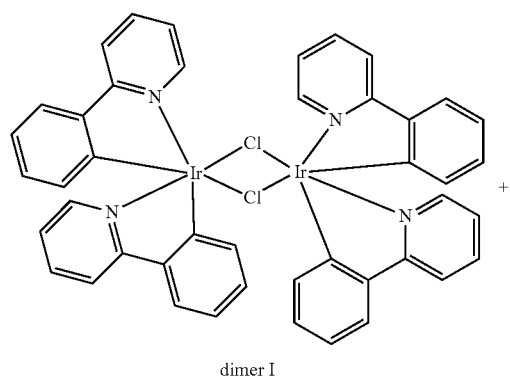

dimer I

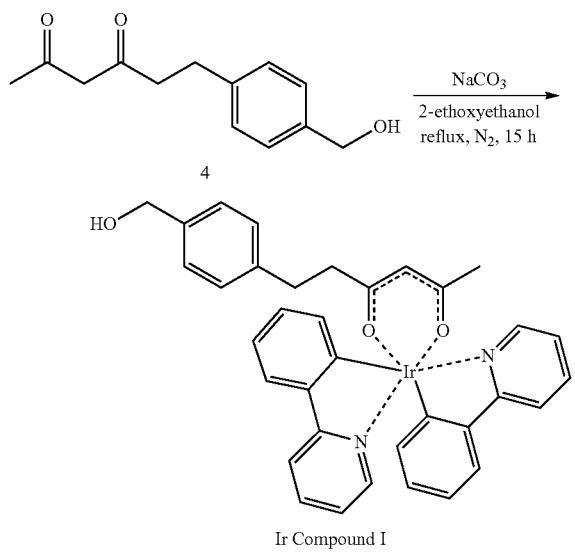

Ir Compound I

Example 4

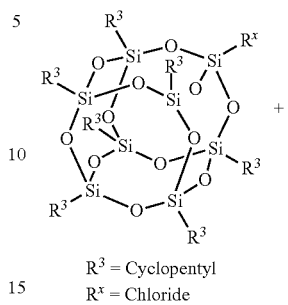

$R^3$ = Cyclopentyl
$R^x$ = Chloride

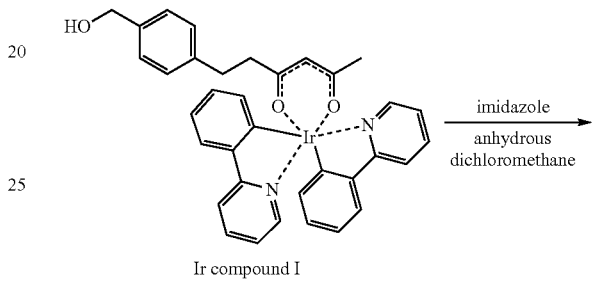

Ir compound I

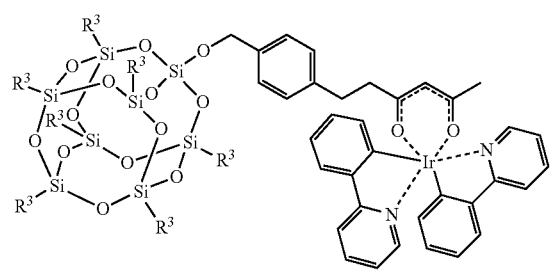

$R^3$ = Cyclopentyl
(POSS)(Ir Compound I)

Synthetic Procedure of Ir-Compound I:

Dimer I (3.11 g, 2.9 mmol), 4 (1.64 g, 7.45 mmol), and sodium bicarbonate $Na_2CO_3$ (3.26 g) were dissolved in 2-ethoxyethanol (50 mL) and refluxed under argon atmosphere for 12-15 h. After cooling, $Na_2CO_3$ was filtered off. The filtrate was evaporated under a reduced pressure and the resulting residue was redissolved in dichloromethane. The solution was washed with water and brine. The organic layer was dried over $MgSO_4$ and then subjected to silica-gel column chromatography eluted with 1:1 ratio ($R_f$=0.33) of ethyl acetate and hexane, and gave 2.85 g (68%) of Ir compound I. MS (m/z): calculated for $C_{35}H_{31}IrN_2O_3$ 719.85. found 720.0. Melting point: 245° C. TGA; $T_{5\%}$=309° C. in air.

Synthetic Procedure of (POSS)(Ir-Compound I)—Green Emitting:

Ir compound I (0.47 g, 0.65 mmol), 1.5 equiv of POSS-Chloro-heptacyclopentyl substituted (0.92 g, 0.98 mmol), and 2 equiv of imidazole (89 mg, 1.3 mmol) in anhydrous dichloromethane was stirred for 2 h at room temperature. The reaction mixture was then washed with water and brine. The organic layer was dried over $MgSO_4$, giving 1.54 g of the crude product as a yellow solid. The crude solid was purified by a silica-gel chromatography eluting with 1:4 ratio ($R_f$=0.25) of ethyl acetate and hexane, and gave 0.88 g (83%) (POSS)(Ir Compound I). $C_{70}H_{94}IrN_2O_{15}Si_8$ m/e: 1619.44 (100%). MS (m/z): calculated for $C_{70}H_{93}IrN_2O_{15}Si_8$ 1619.39. found 1619.

Example 5

[Ir(μ-Cl)(bt)$_2$]$_2$, dimer II, was synthesized in a similar manner as described with respect to dimer I in Example 2.

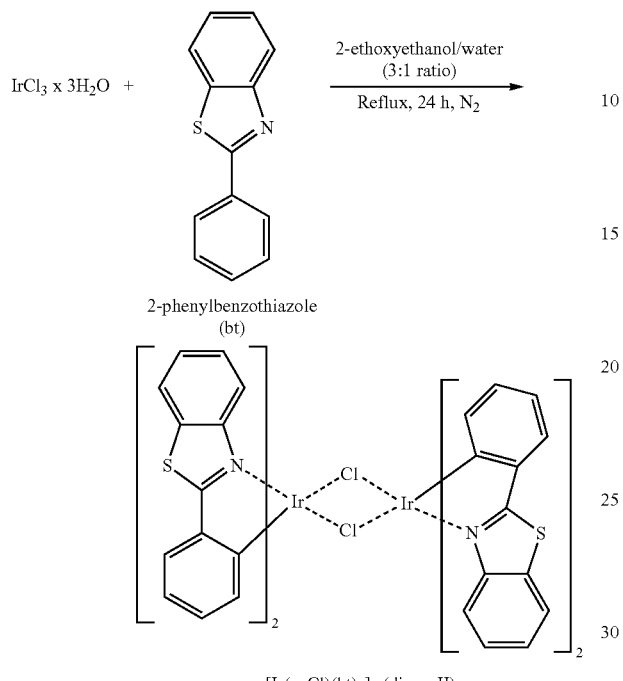

Example 6

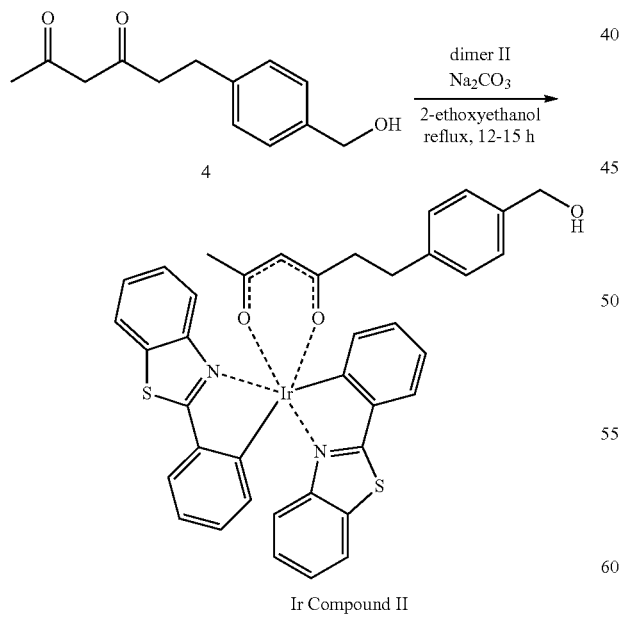

Synthetic Procedure of Ir Compound II:

Dimer II (3.095 g, 2.36 mmol), 4 (1.33 g, 6.0 mmol), and sodium carbonate (2.66 g, 23.6 mmol) were dissolved in 2-ethoxyethanol and refluxed for 12-15 h under nitrogen atmosphere. The crude mixture was then cooled to room temperature and the solvent was evaporated by reduced pressure. The dark orange crude product was purified via silica-gel chromatography using a 1:1 ratio of EtOAc and hexane ($R_f$=0.56), and gave 2.8 g (73% yield) of Ir Compound II as fine red powder.

Example 7

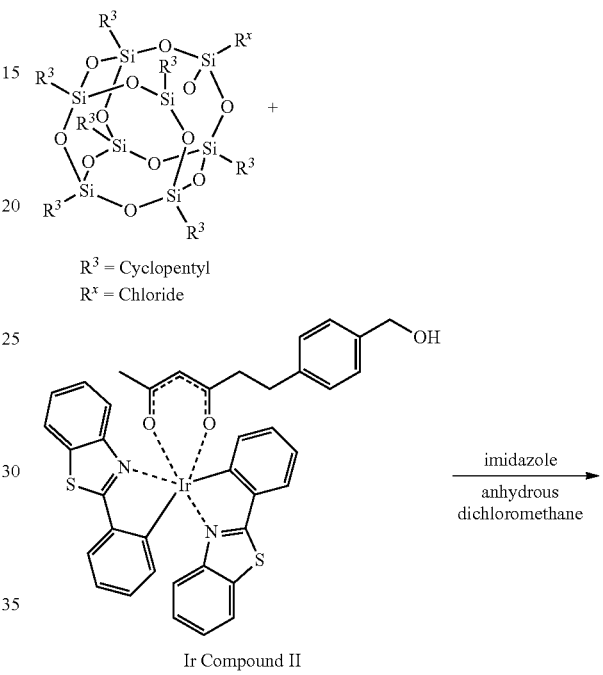

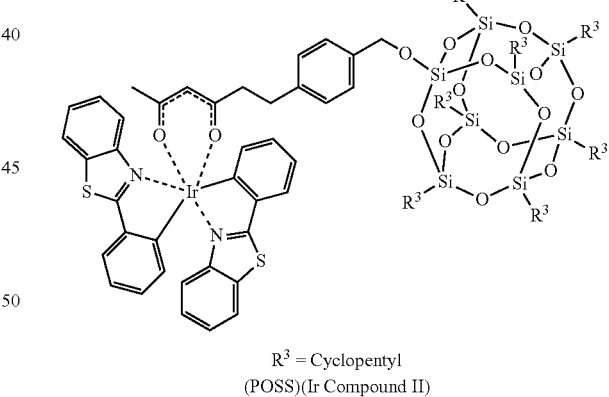

Synthetic Procedure of (POSS)(Ir-Compound II)—Orange Emitting:

Ir Compound II (0.3 g, 0.36 mmol), 1.5 equiv of POSS-Chloro-heptacyclopentyl substituted (0.51 g, 0.54 mmol), and 2 equiv of imidazole (49 mg, 0.72 mmol) were dissolved in anhydrous dichloromethane and stirred for 2 h at room temperature. The reaction mixture was evaporated by rotary evaporator and then extracted with ethylacetate. The crude product was purified via silica-gel chromatography using 1:4 ratio of EtOAc and hexane ($R_f$=0.44), and gave 0.6 g (96% yield) of (POSS)(Ir Compound II) as a fine orange powder.

Example 8

[Ir(pq)$_2$(μ-Cl)]$_2$, dimer III, was synthesized in a similar manner as described with respect to dimer I in Example 2.

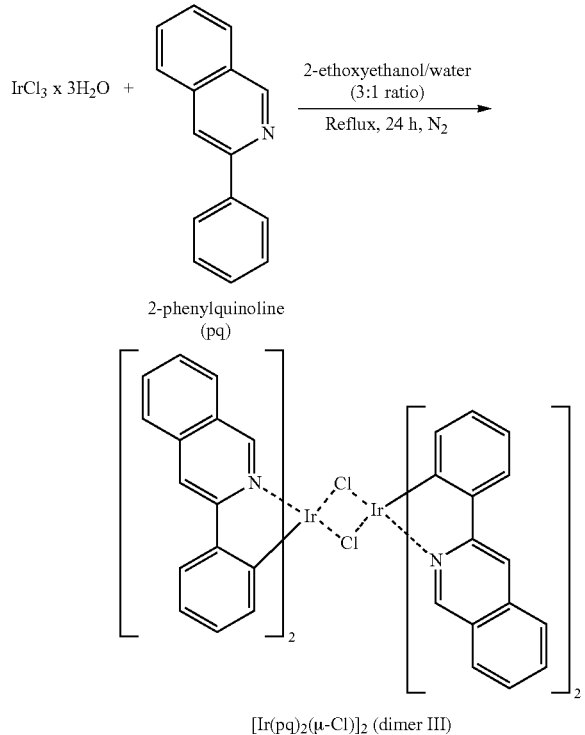

[Ir(pq)$_2$(μ-Cl)]$_2$ (dimer III)

Example 9

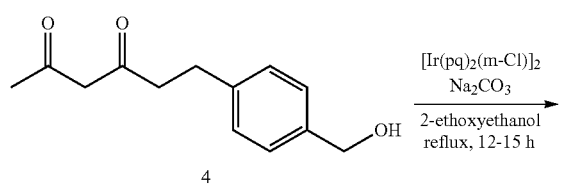

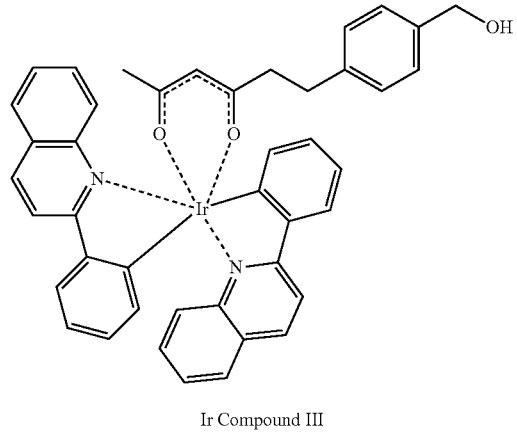

Ir Compound III

Synthetic Procedure of Ir Compound III:
Ir compound III was synthesized in a similar manner as described with respect to Ir compound I and Ir compound II in Examples 3 and 6, respectively.

Example 10

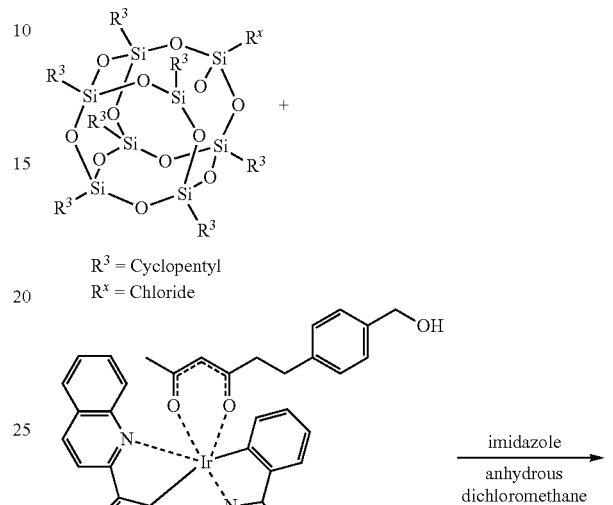

$R^3$ = Cyclopentyl
$R^x$ = Chloride

Ir Compound III $R^3$ = Cyclopentyl
(POSS)(Ir Compound III)

Synthetic Procedure of (POSS)(Ir Compound III)—Red Emitting:
(POSS)(Ir compound III) was synthesized in a similar manner as described with respect to (POSS)(Ir compound II) in Example 7.

Example 11

-continued

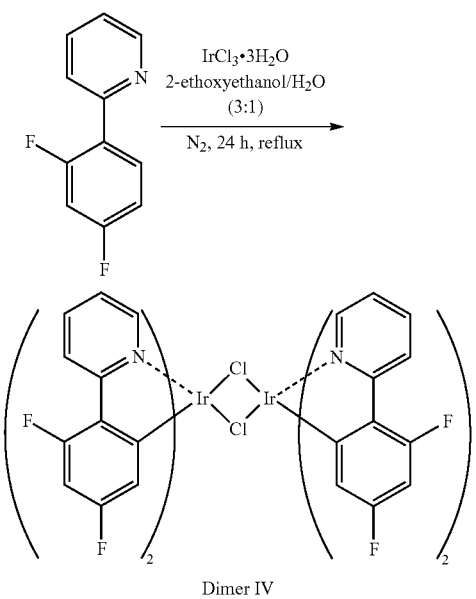

Dimer IV

Synthetic Procedure of Dimer IV, [(dfppy)$_2$Ir(μ-Cl)]$_2$:

Dimer IV was synthesized in accordance to the procedures disclosed in *J. Am. Chem. Soc.,* 2005, 127, 12438, which is hereby incorporated by reference in its entirety. Yield of dimer IV was 76%.

Example 12

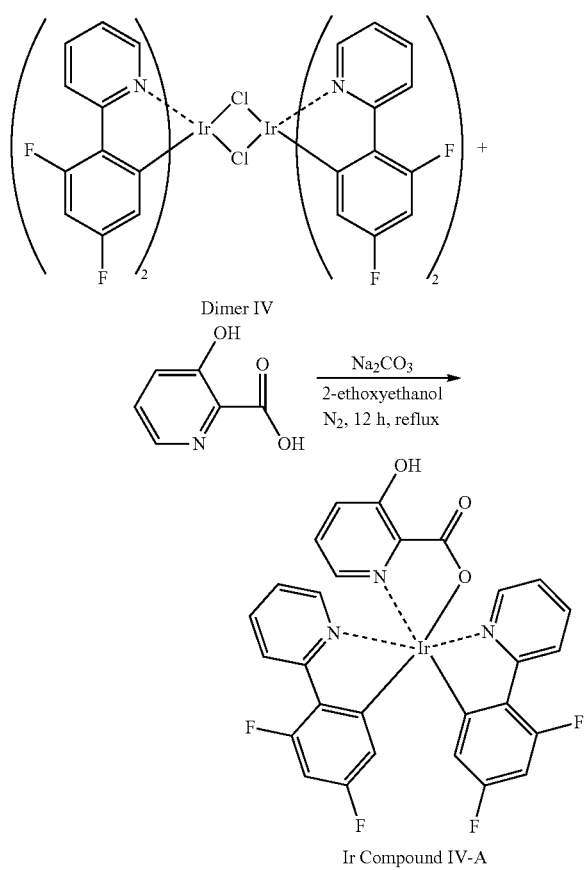

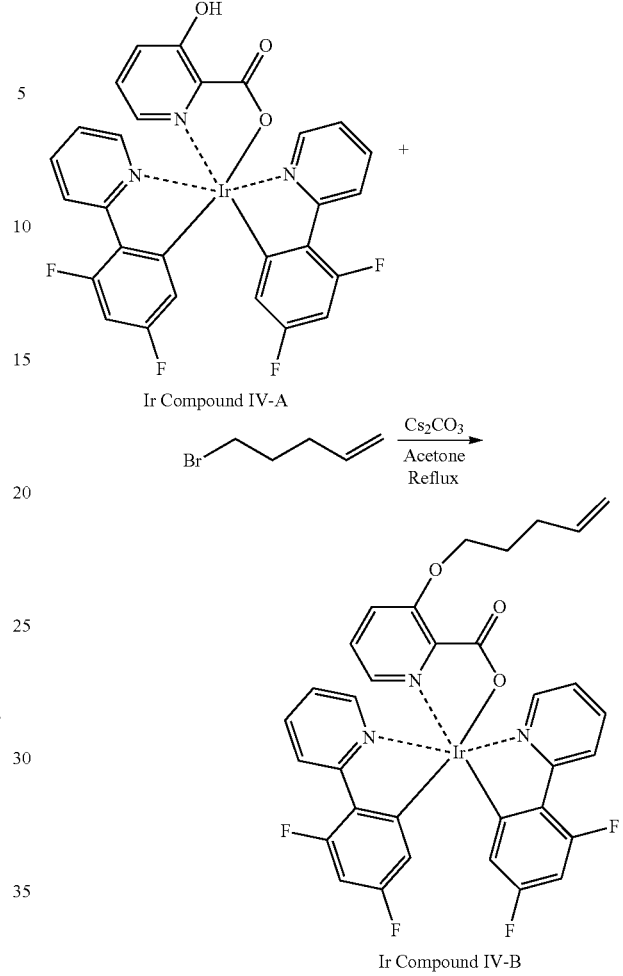

Synthetic Procedure of (Ir Compound IV-A):

Dimer IV (500 mg, 0.41 mmol), sodium carbonate (437 mg, 4.1 mmol), and 2.6 equivalent of 3-hydroxypicolinc acid (148 mg, 1.06 mmol) were dissolved in 30 mL of 2-ethoxyethanol. The reaction vessel was degrassed and maintained under nitrogen. The temperature was raised to 140° C. and the reaction mixture was stirred for 12 h. After cooling to room temperature, the crude mixture was poured into EtOAc (150 mL). The mixture was washed with water (100 mL×3 times) to remove 2-ethoxyethanol. The product was recrystallized from ethyl acetate and gave 355 mg (61%) of the product as a fine yellow powder.

Synthetic Procedure of (Ir Compound IV-B):

To a solution of Ir Compound IV-A (1.80 g, 2.5 mmol) in acetone (80 mL) were added 5-bromo-1-pentene (300 μL, 2.5 mmol) and Cs$_2$CO$_3$ (1.20 g, 3.8 mmol). The reaction mixture was refluxed for 24 h. After cooling to room temperature, the solvent was evaporated in vacuum and methylene chloride was added into the mixture. The organic phase was washed with water and dried over Na$_2$SO4. The solvent was evaporated to give the crude product, which was applied to column chromatography on silica gel, eluting with methylene chloride and ethyl acetate (1:1 v/v) to provide the product. The solidified product was filtered through a Buchner funnel and then washed with hexane several times to provide the desired product (Yield: 0.837 g, 42%) as a pale yellow-greenish fine powder.

Example 13

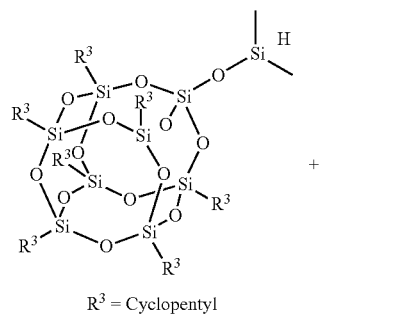

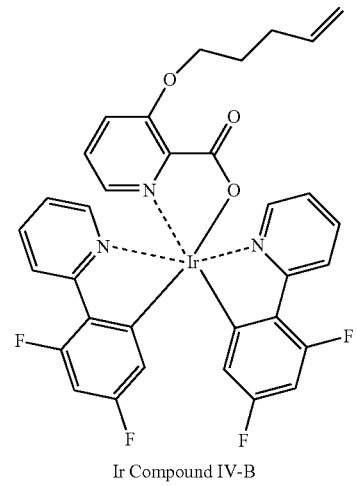

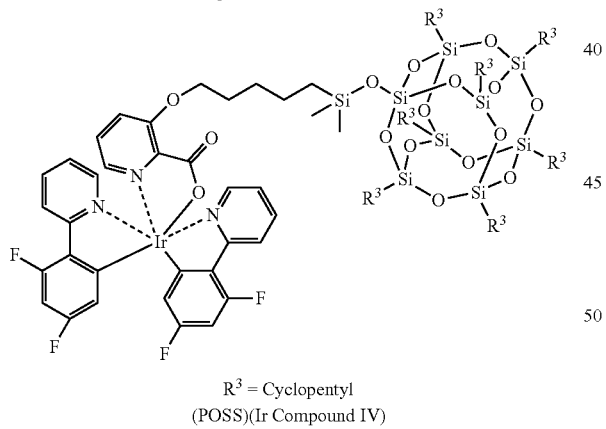

Synthetic Procedure of (POSS)(Ir Compound IV)—Blue Emitting:

Ir Compound IVB (0.96 g, 1.23 mmol), and PSS-(Hydridodimethyl-siloxy)-Heptacyclopentyl substituted (Aldrich) (1.20 g, 1.23 mmol) were dissolved in 10 mL dry toluene, followed by addition of Pt(0)-1,3-divinyl-1,1,3,3-tetramethyldisiloxane, Pt(dvs) catalyst (0.03 mL). The reaction mixture was stirred for 24 h under Ar atmosphere before poured into excess amount of methanol. The precipitate was purified by a silica-gel chromatography with 4:1 ratio of n-Hexane:EtOAc as eluent, giving 1.8 g (82%) of (POSS)(Ir Compound IV) as a pale green powder.

Example 14

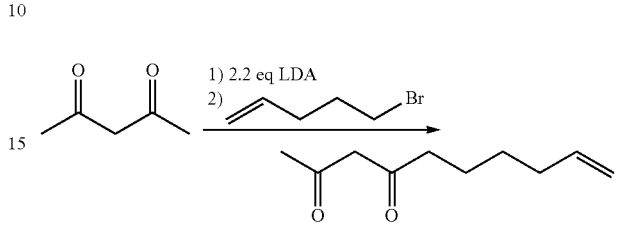

Dec-9-ene-2,4-dione was synthesized using a similar procedure as described in Example 1 or following the literature procedure described in *Helv. Chim. Acta.*, 1977, 60, 638.

Example 15

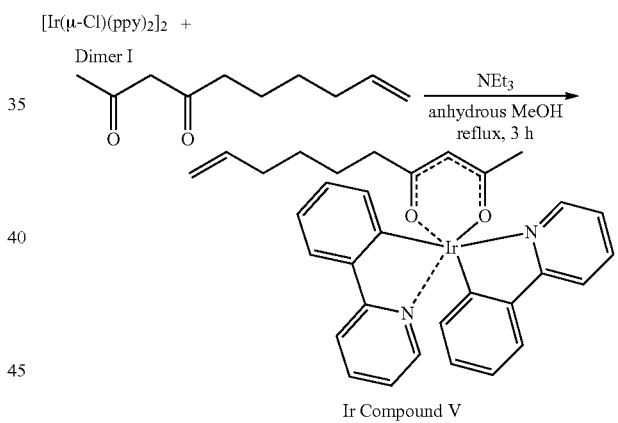

Synthetic Procedure of Ir Compound V:

Dimer I [Ir(ppy)$_2$(μ-Cl)] (6.0 g, 5.6 mmol) was suspended in 100 mL of anhydrous methanol degassed with nitrogen gas. Dec-9-ene-2,4-dione (2.19 g, 13 mmol) and triethylamine (NEt$_3$) (2.40 mL, 17.5 mmol) were added, and the obtained mixture was heated to reflux for 3 h. The resulting reaction mixture was cooled to room temperature and concentrated by using a rotary evaporator. The crude mixture was extracted with 200 mL of chloroform (CHCl$_3$) and washed with water (100 mL×3) and brine. The organic layer was dried over magnesium sulfate. After removal of the solvent, the residue was purified by flash chromatography using silica-gel, with 1:2 ratio of EtOAc:n-Hexane as eluent, giving 4.8 g (64%) the product, Ir Compound V, as of fine yellow powder.

Example 16

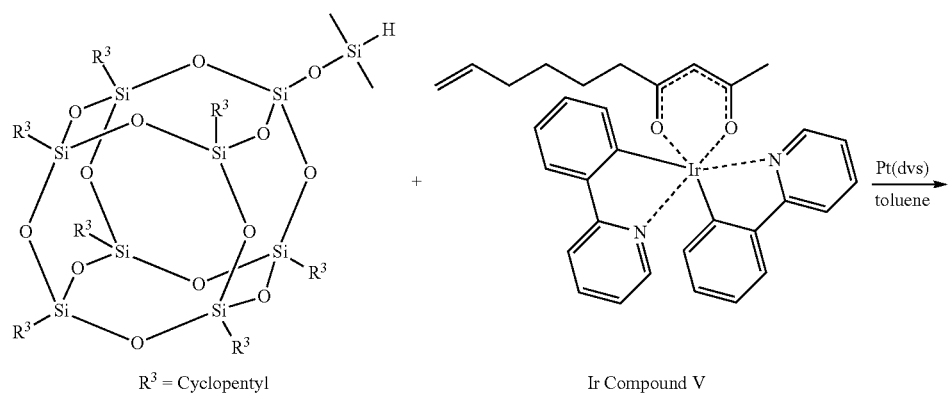

R³ = Cyclopentyl

Ir Compound V

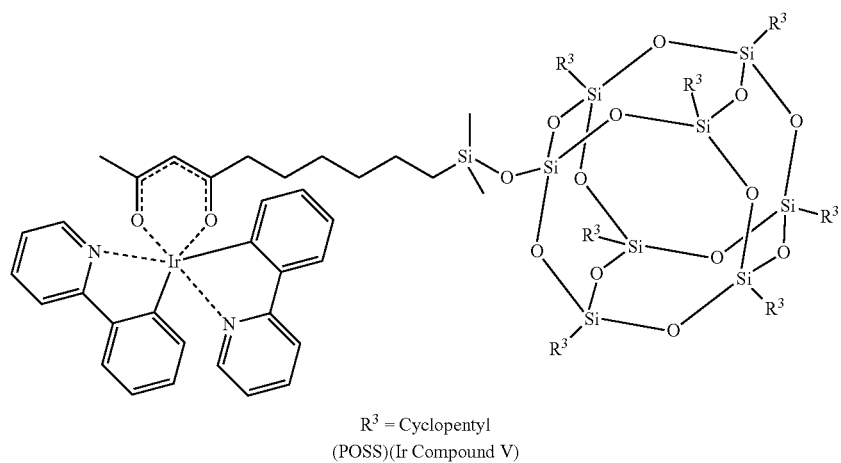

R³ = Cyclopentyl
(POSS)(Ir Compound V)

Synthetic Procedure of (POSS)(Ir-Compound V)—Green Emitting:

Ir Compound V (800 mg, 1.2 mmol) and PSS-(Hydridodimethyl-siloxy)-Heptacyclopentyl substituted (Aldrich) (1.17 g, 1.2 mmol) were dissolved in 10 mL of dry toluene, followed by addition of Pt(0)-1,3-divinyl-1,1,3,3-tetramethyldisiloxane, Pt(dvs) catalyst (0.03 mL). The reaction mixture was stirred for 24 h under Ar atmosphere before poured into excess amount of methanol. The precipitate was purified by a silica-gel chromatography with 1:4 ratio of n-Hexane: EtOAc as eluent, giving 1.8 g (92%) of (POSS)(Ir Compound V) as a pale yellow powder.

Example 17

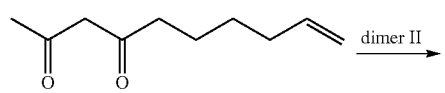

-continued

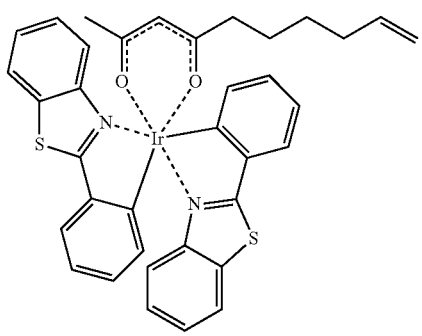

Ir Compound VI

Synthetic Procedure of Ir Compound VI:
Ir compound VI is synthesized in a similar manner as described with respect to Ir compound V in Example 15.

Example 18

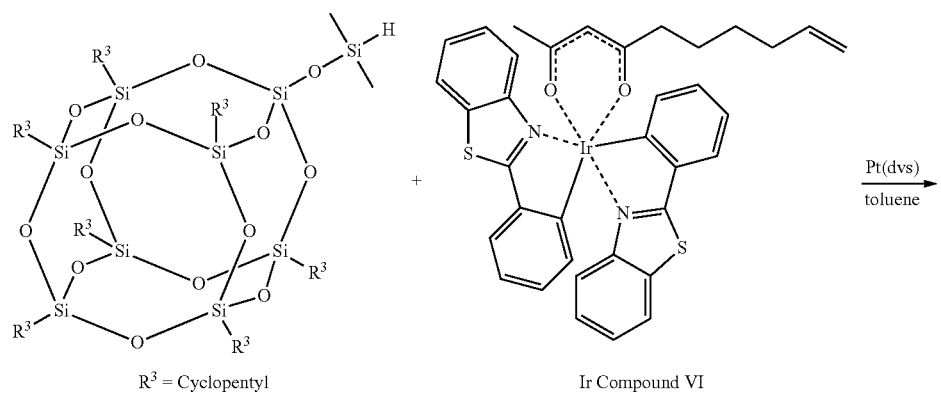

R³ = Cyclopentyl  
Ir Compound VI

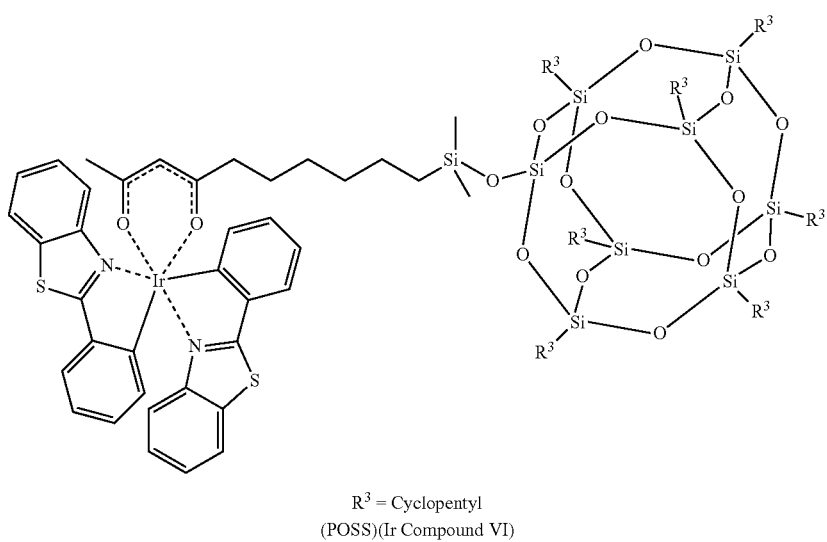

R³ = Cyclopentyl  
(POSS)(Ir Compound VI)

Synthetic Procedure of (POSS)(Ir Compound VI)—Orange Emitting:

(POSS)(Ir Compound VI) is synthesized in a similar manner as described with respect to (POSS)(Ir Compound V) in Example 16.

Example 19

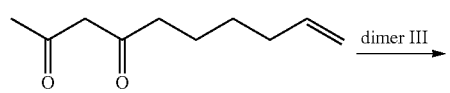

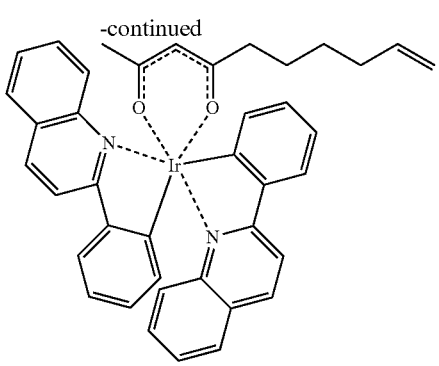

Ir Compound VII

Synthetic Procedure of Ir Compound VII:
Ir compound VII is synthesized in a similar manner as described with respect to Ir compound V in Example 15.

Example 20

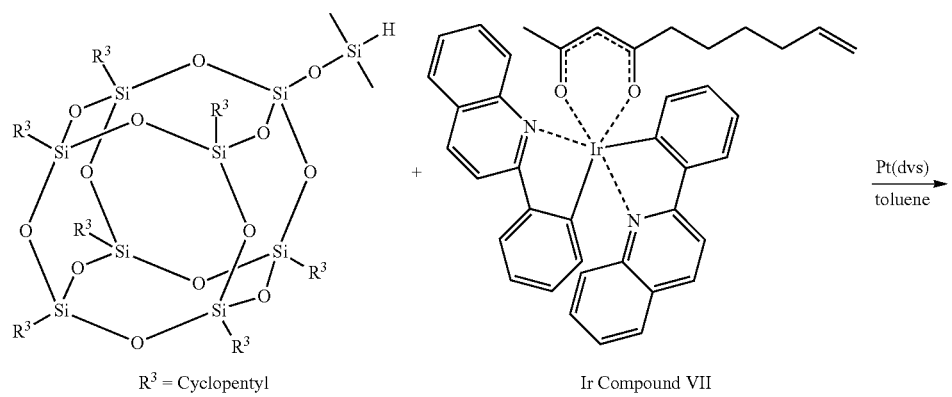

R³ = Cyclopentyl    Ir Compound VII

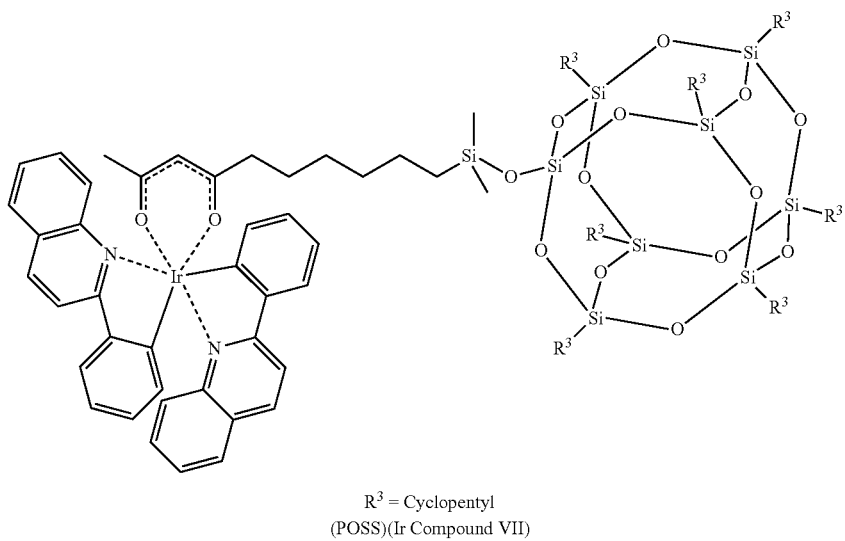

R³ = Cyclopentyl
(POSS)(Ir Compound VII)

Synthetic Procedure of (POSS)(Ir Compound VII)—Red Emitting:

(POSS)(Ir Compound VII) is synthesized in a similar manner as described with respect to (POSS)(Ir Compound V) in Example 16.

Example 21

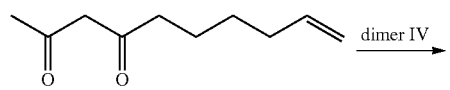 dimer IV →

-continued

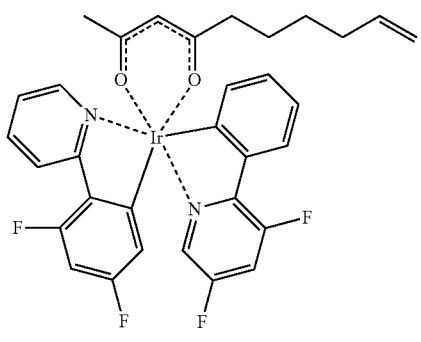

Ir Compound VIII

Synthetic Procedure of Ir Compound VIII:
Ir compound VIII is synthesized in a similar manner as described with respect to Ir compound V in Example 15.

Example 22

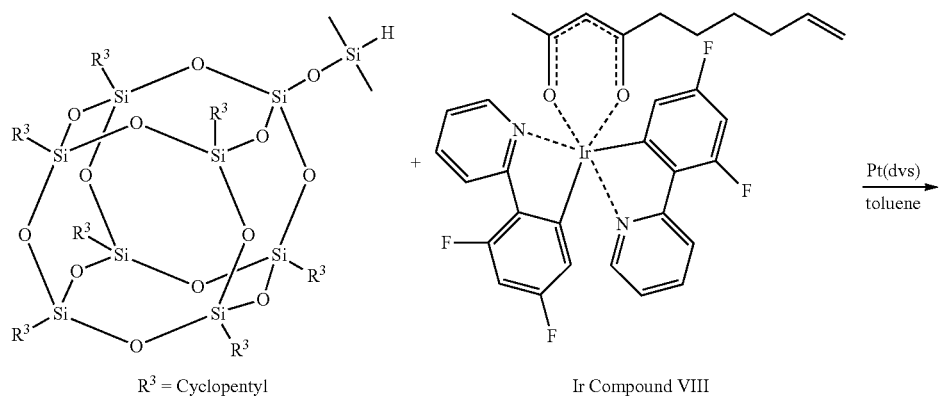

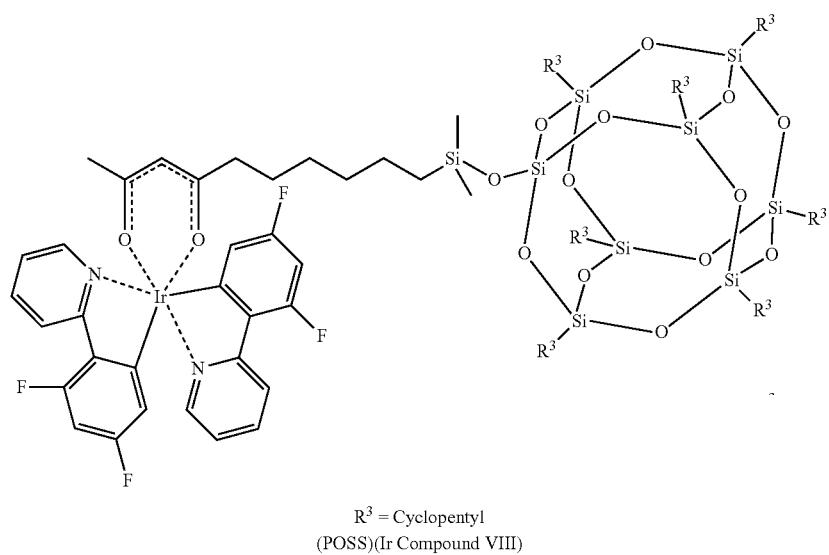

Synthetic Procedure of (POSS)(Ir Compound VIII)—Blue Emitting:

(POSS)(Ir Compound VIII) is synthesized in a similar manner as described with respect to (POSS)(Ir Compound V) in Example 16.

Example 23

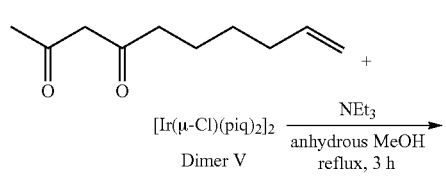

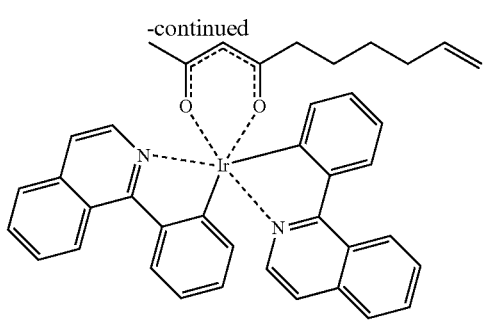

Synthetic Procedure of Ir Compound IX:

Ir compound IX is synthesized in a similar manner as described with respect to Ir compound V in Example 15. The synthesis of Dimer V was adopted from literature: *Adv. Mater.* 2003, 15, 884.

Example 24
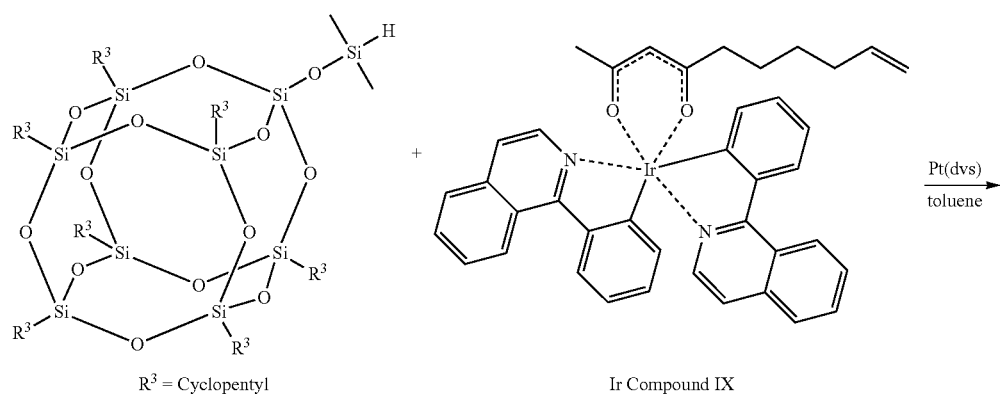
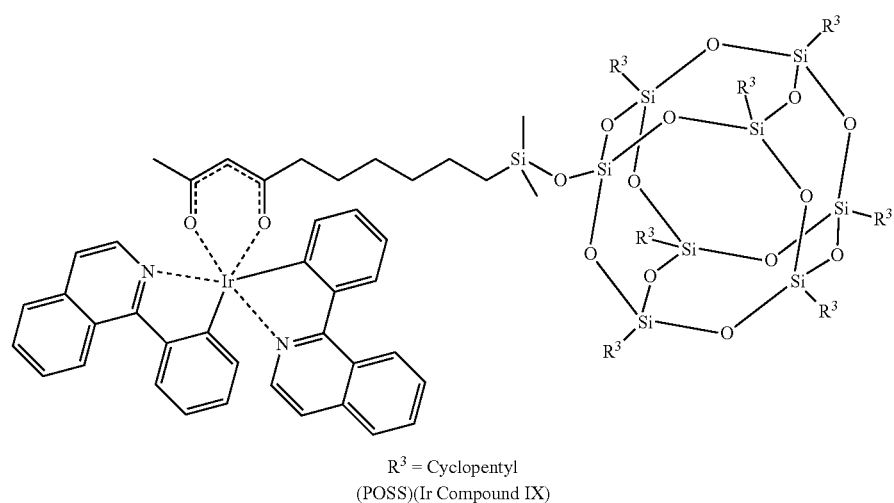
Synthetic Procedure of (POSS)(Ir Compound IX)—Red Emitting:
(POSS)(Ir Compound IX) is synthesized in a similar manner as described with respect to (POSS)(Ir Compound V) in Example 16.

Example 25

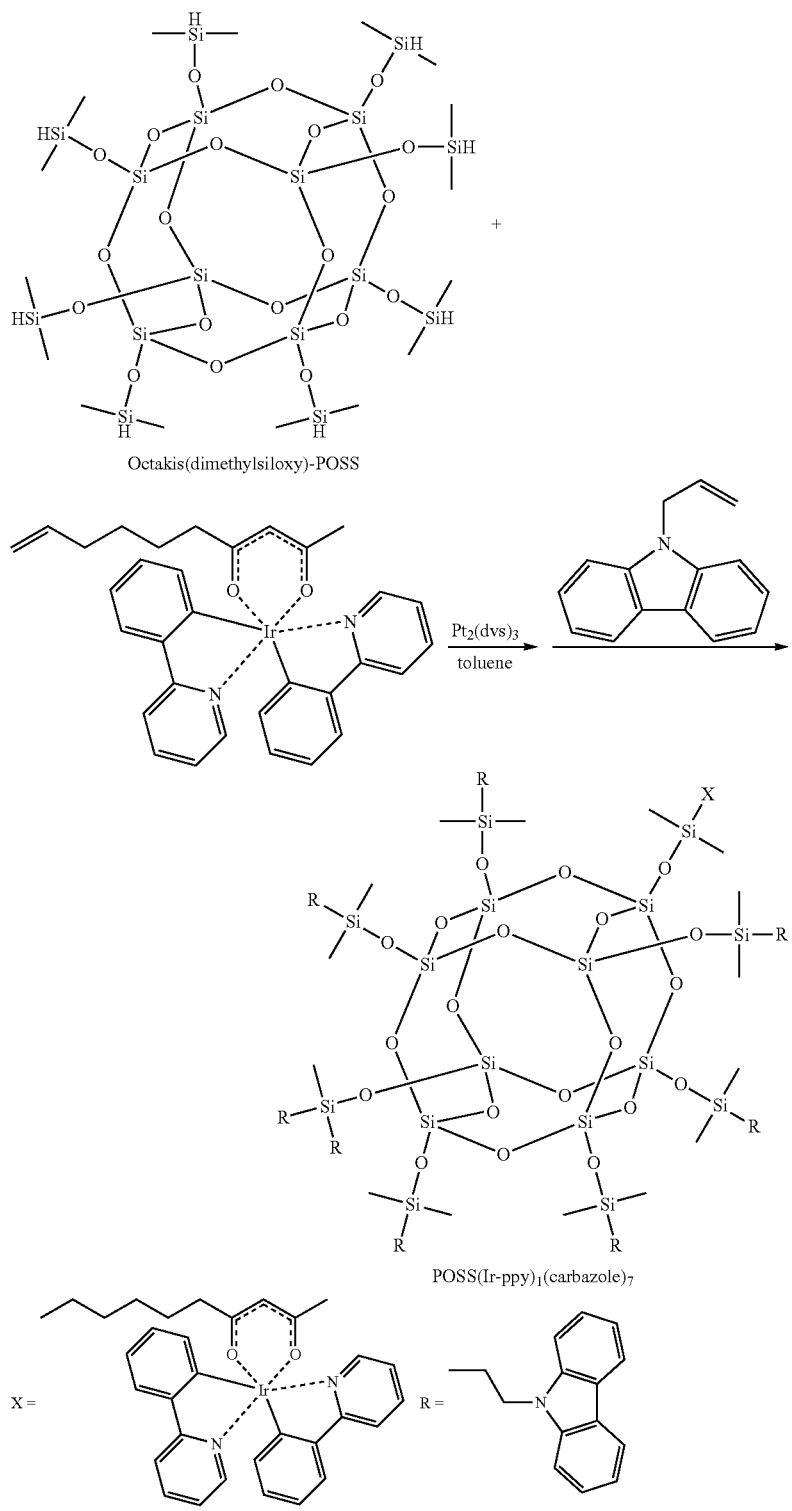

Octakis(dimethylsiloxy)-POSS

POSS(Ir-ppy)$_1$(carbazole)$_7$

Synthetic Procedure of POSS(Ir-ppy)$_1$(carbazole)$_7$:

a round bottom flask was charged with a stirbar, Octakis (dimethylsiloxy)-POSS (492 mg, 0.483 mmol), (Ir Compound V) (323 mg, 0.483 mmol), and anhydrous toluene (20 ml). The solution was degassed with argon for 5 minutes and then platinum-divinyltetramethyl disiloxane (Pt(dvs)) (0.04 ml, 2% Pt wt. solution in xylene) was added and the reaction mixture was stirred at room temperature under positive argon pressure for 1 hour. N-allylcarbazole (1.00 g, 4.83 mmol) was added and the reaction mixture was allowed to stir at room temperature for 2 hours. The toluene was evaporated in vacuo and the product was separated chromatographically using 1:1 dichloromethane:hexanes to yield 301 mg (20%).
Example 26
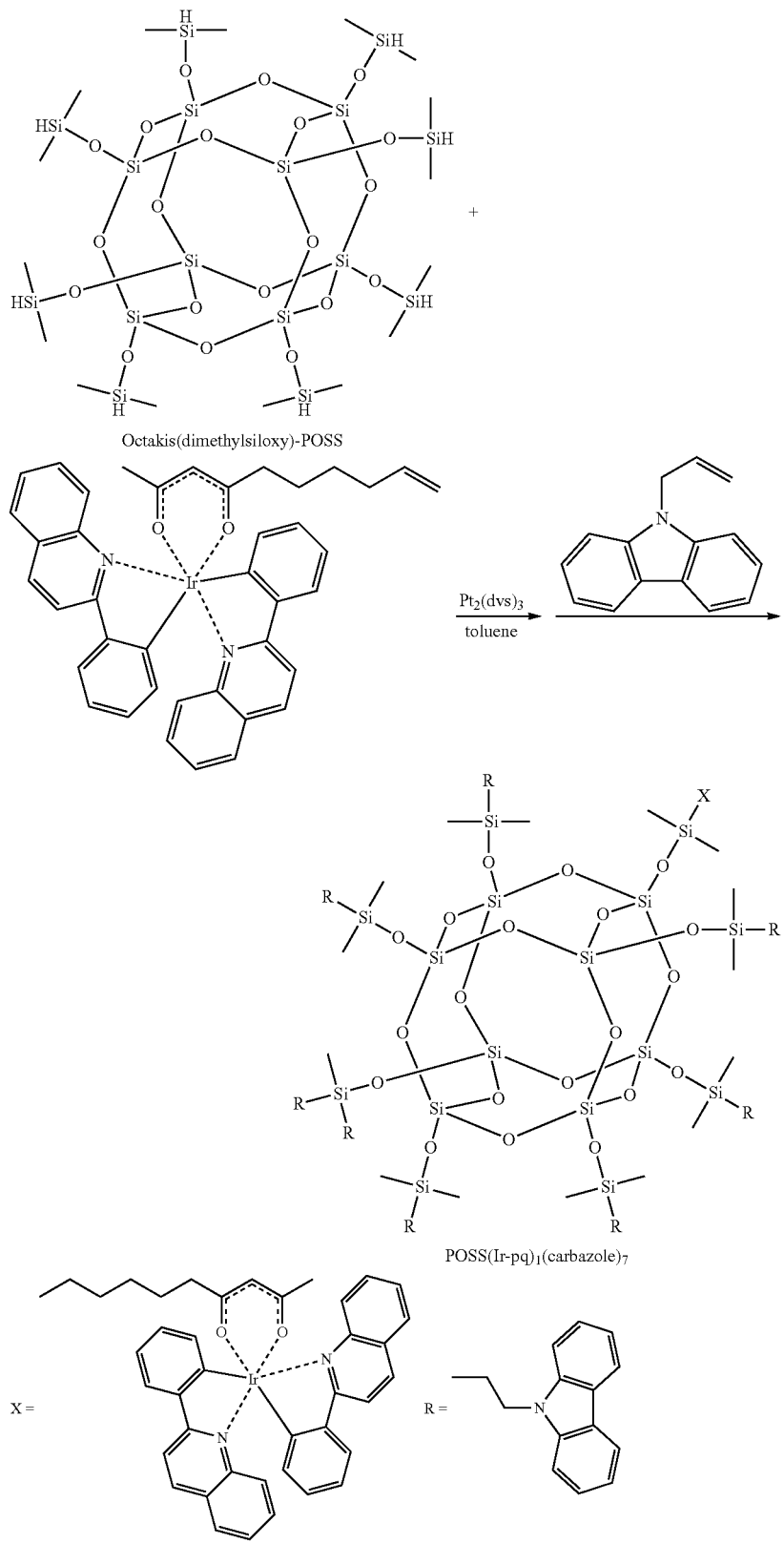

Synthetic Procedure of POSS(Ir-pq)₁(carbazole)₇:

a round bottom flask was charged with a stirbar, Octakis(dimethylsiloxy)-POSS (492 mg, 0.483 mmol), (Ir Compound VII) (371 mg, 0.483 mmol), and anhydrous toluene (20 ml). The solution was degassed with argon for 5 minutes and then platinum-divinyltetramethyl disiloxane (Pt(dvs)) (0.04 ml, 2% Pt wt. solution in xylene) was added and the reaction mixture was stirred at room temperature under positive argon pressure for 1 hour. N-allylcarbazole (1.00 g, 4.83 mmol) was added and the reaction mixture was allowed to stir at room temperature for 2 hours. The toluene was evaporated in vacuo and the product was separated chromatographically using 1:1 dichloromethane:hexanes to yield 299 mg (19%).

Example 27

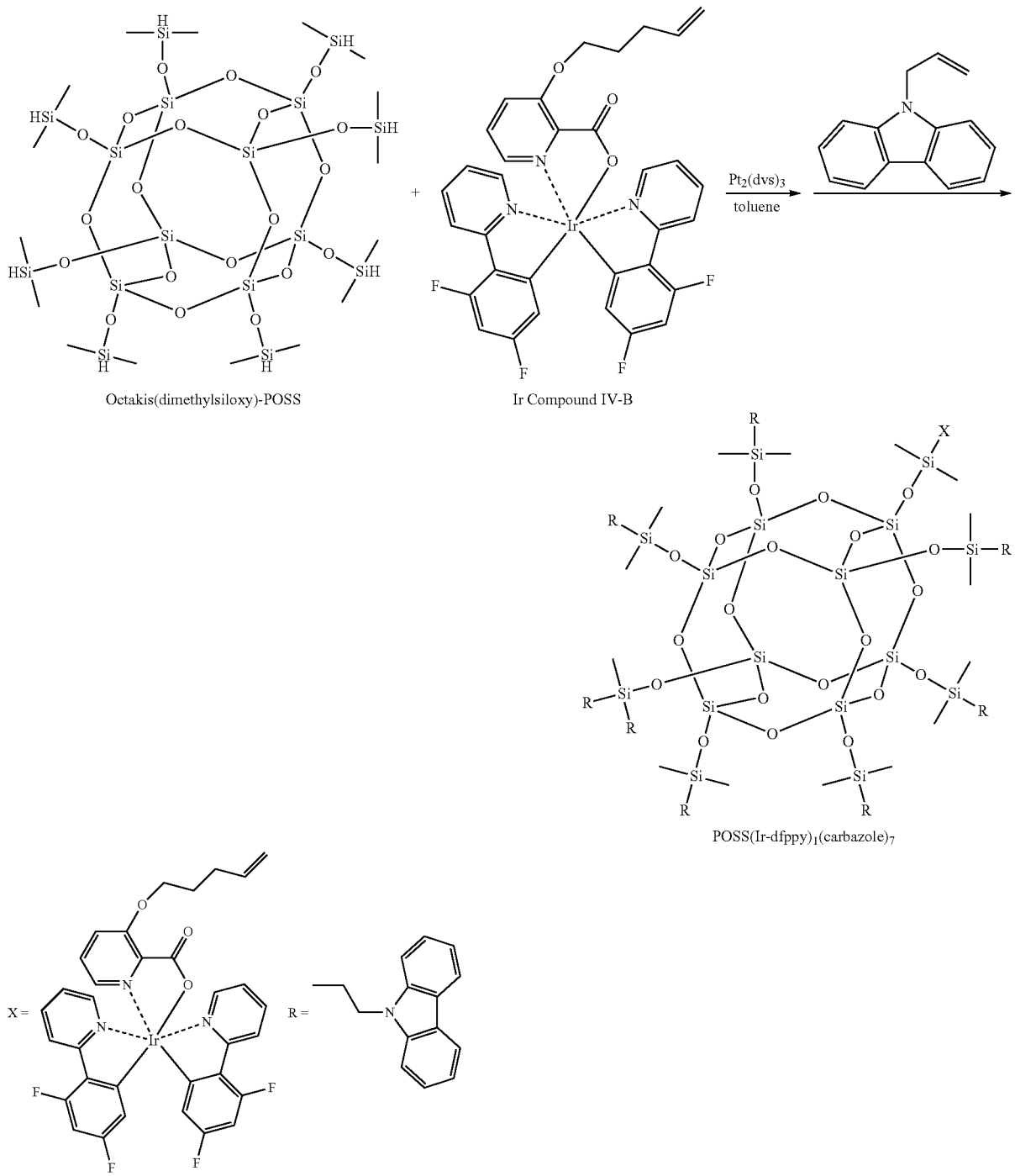

Synthetic Procedure of POSS(Ir-dfppy)₁(carbazole)₇:

synthesized in a similar manner as described in POSS(Ir-ppy)₁(carbazole)₇ in Example 25.

Example 28
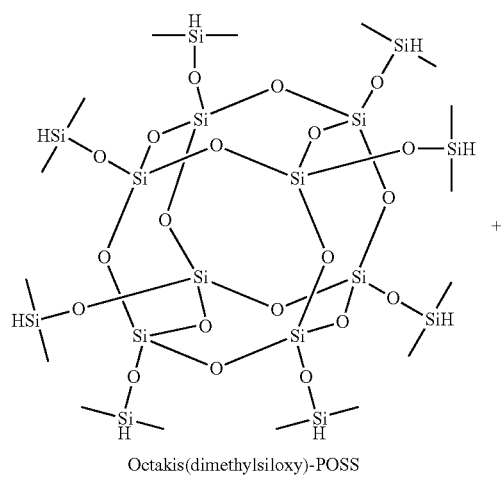
Octakis(dimethylsiloxy)-POSS
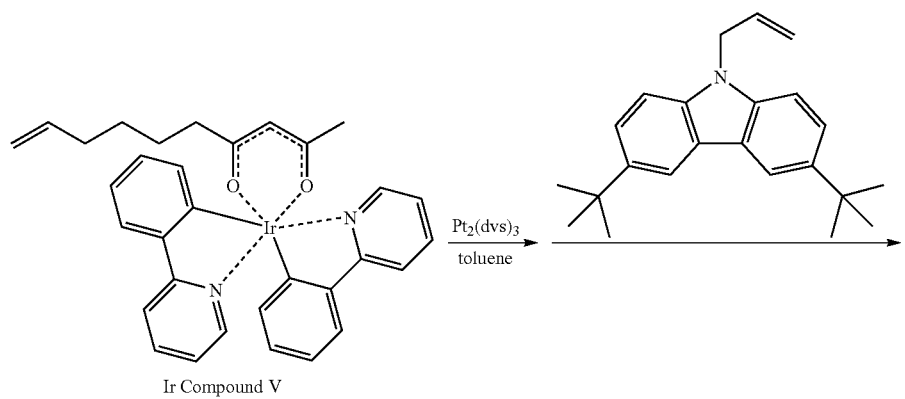
Ir Compound V
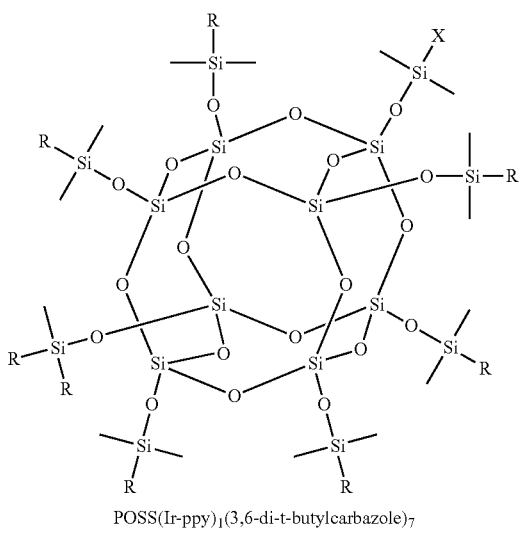
POSS(Ir-ppy)₁(3,6-di-t-butylcarbazole)₇

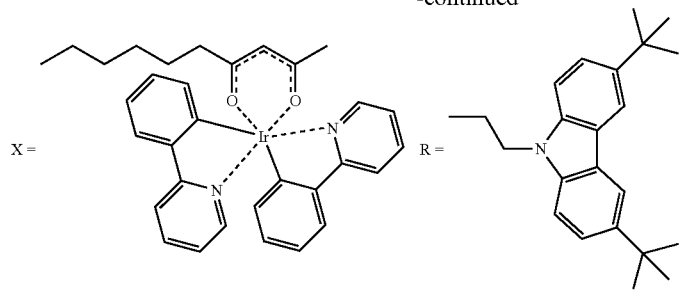

Synthetic Procedure of POSS(Ir-ppy)₁(3,6-di-t-butylcarbazole)₇:

a round bottom flask was charged with a stirbar, Octakis(dimethylsiloxy)-POSS (463 mg, 0.455 mmol), (Ir Compound V) (304 mg, 0.455 mmol), and anhydrous toluene (20 ml). The solution was degassed with argon for 5 minutes and then platinum-divinyltetramethyl disiloxane (Pt(dvs)) (0.04 ml, 2% Pt wt. solution in xylene) was added and the reaction mixture was stirred at room temperature under positive argon pressure for 1 hour. 9-allyl-3,6-di-tert-butylcarbazole (1.450 g, 4.455 mmol) was added and the reaction mixture was allowed to stir at room temperature overnight. The toluene was evaporated in vacuo and the product was separated chromatographically using 1:1 dichloromethane:hexanes to yield 290 mg (16%).

Example 29

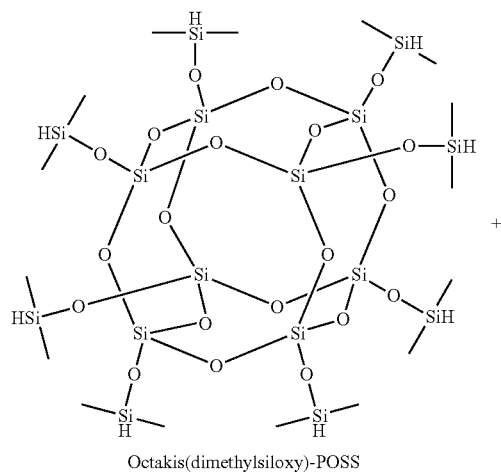

Octakis(dimethylsiloxy)-POSS

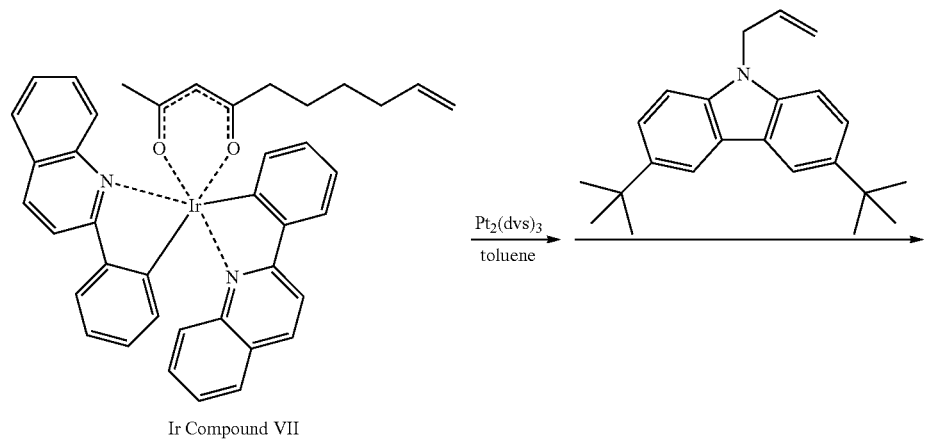

Ir Compound VII

-continued
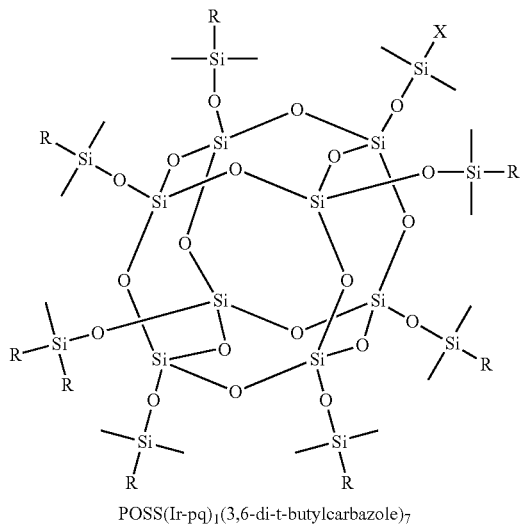
POSS(Ir-pq)₁(3,6-di-t-butylcarbazole)₇
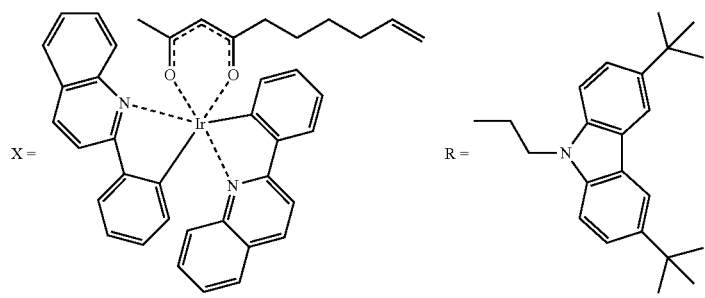
Synthetic Procedure of POSS(Ir-pq)₁(3,6-di-t-butylcarbazole)₇:
POSS(Ir-pq)₁(3,6-di-t-butylcarbazole)₇ is synthesized in a similar manner as described in Example 28.
Example 30
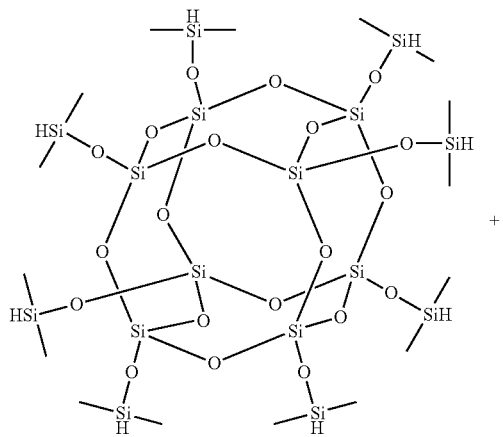
Octakis(dimethylsiloxy)-POSS
+

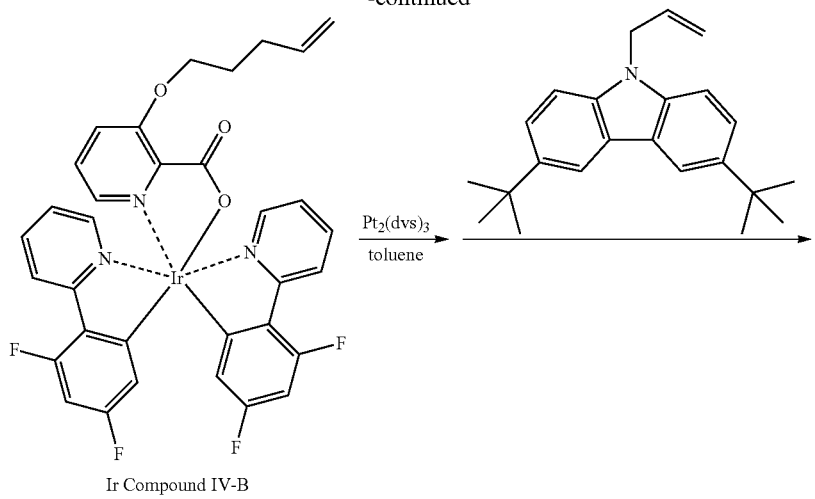

Ir Compound IV-B

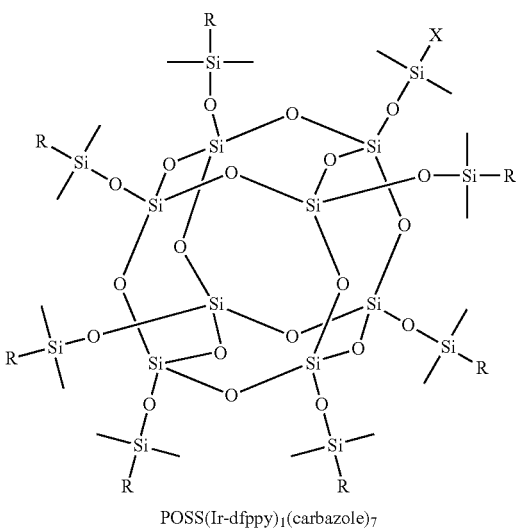

POSS(Ir-dfppy)₁(carbazole)₇

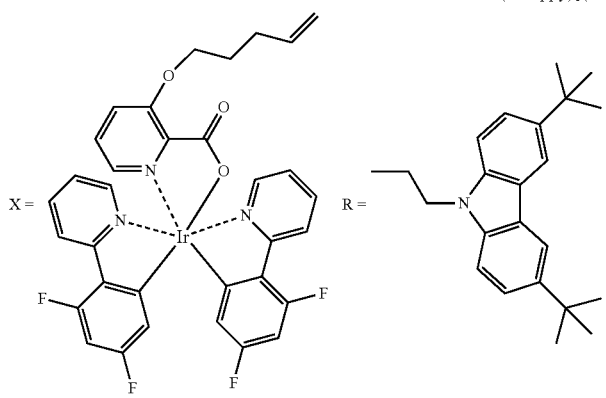

Synthetic Procedure of POSS(Ir-dfppy)₁(3,6-di-t-butyl-carbazole)₇:

POSS(Ir-dfppy)₁(3,6-di-t-butylcarbazole)₇ is synthesized in a similar manner as described in Example 28.

Example 31

Figure 2:
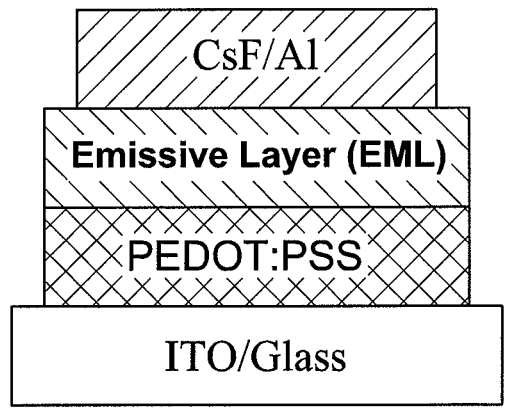
FIG. 2 is exemplary configuration of a single layer device structure.
Figure 3:
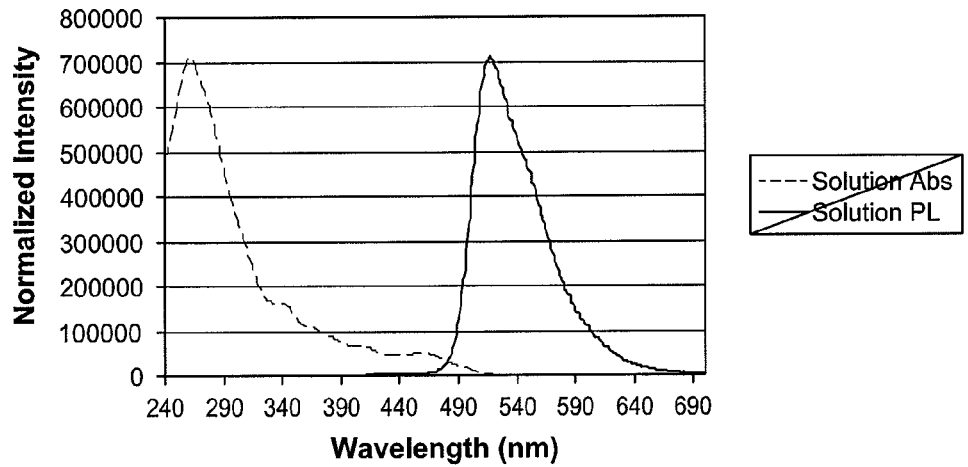
FIG. 3 shows the photoluminescence spectra (PL) of (POSS)(Ir Compound I) in diluted $CHCl_3$.
Figure 4:
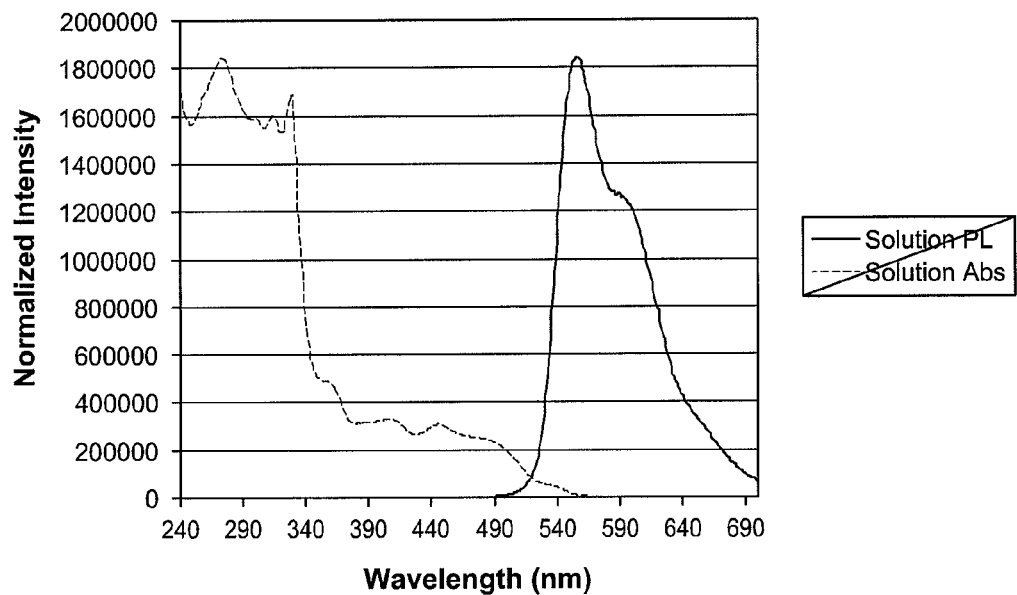
FIG. 4 shows an absorption (Abs) and photoluminescence spectra (PL) of (POSS)(Ir Compound II) in diluted $CHCl_3$.
Figure 5:
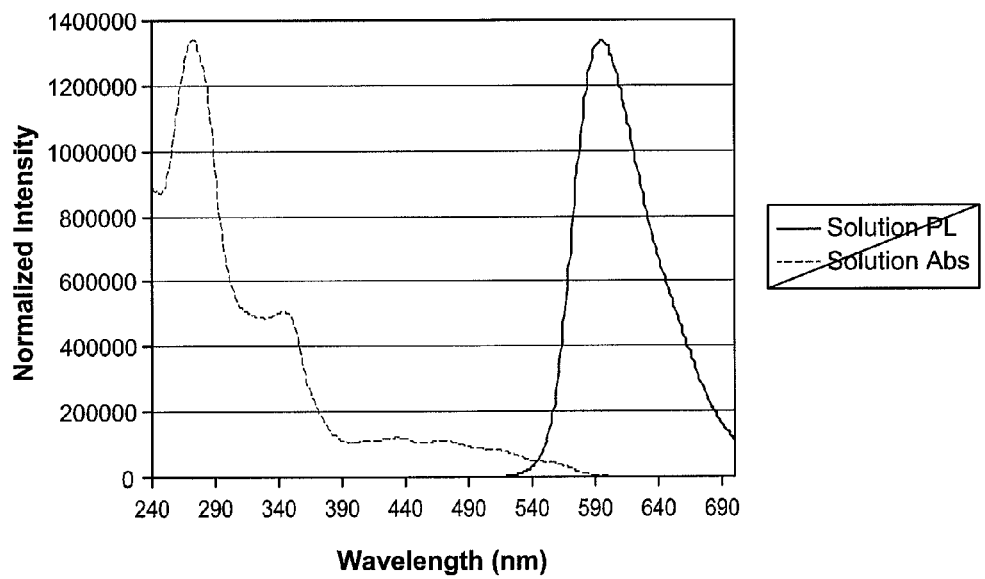
FIG. 5 shows an absorption (Abs) and shows photoluminescence spectra (PL) of (POSS)(Ir Compound III) in diluted $CHCl_3$.
Figure 6:
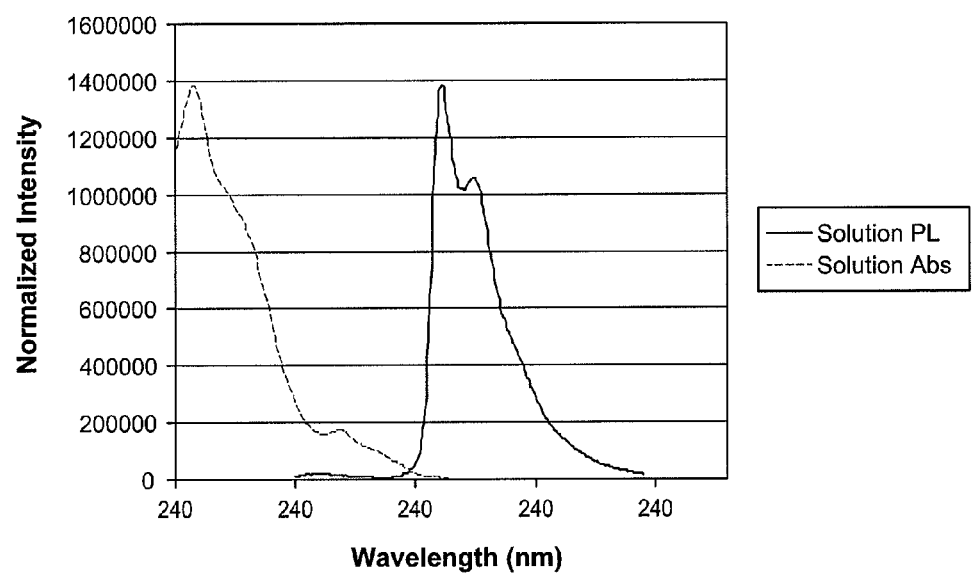
FIG. 6 shows an absorption (Abs) and photoluminescence spectra (PL) of (POSS)(Ir Compound IV) in diluted $CH_2Cl_2$.
Figure 7:
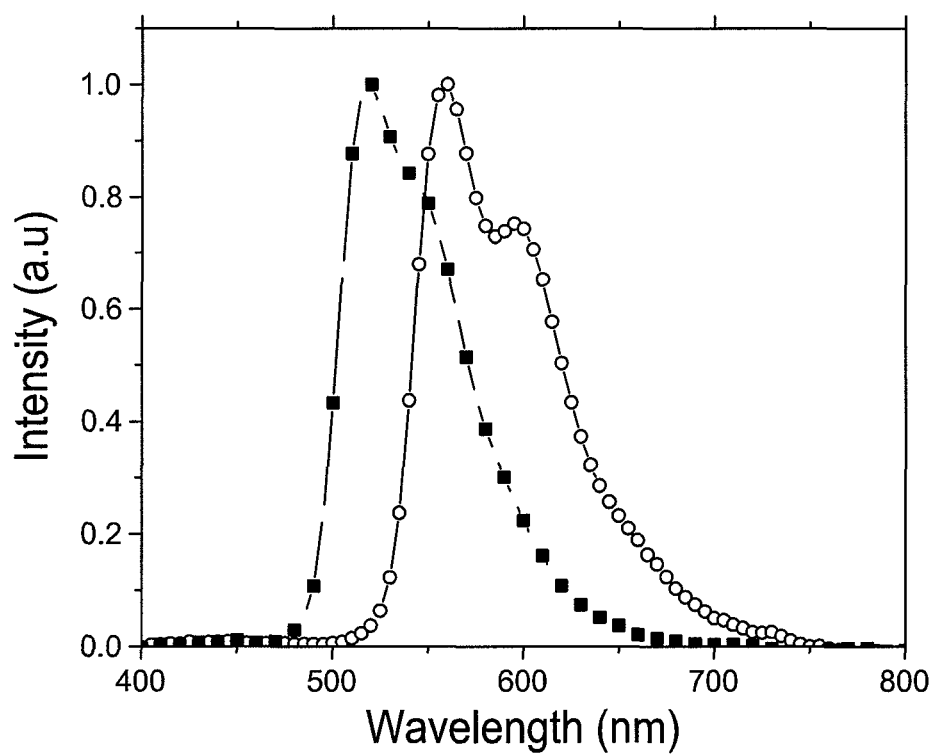
FIG. 7 shows electroluminescent spectra (EL) of a device incorporating (POSS)(Ir Compound I), indicated by squares, and a device incorporating (POSS)(Ir Compound II), indicated by circles, in which the devices have the configuration of ITO/PEDOT:PSS/PVK+PBD+(POSS)(Ir Compound I)/CsF/Al or ITO/PEDOT:PSS/PVK+PBD+(POSS)(Ir Compound II)/CsF/Al, respectively.
Figure 8:
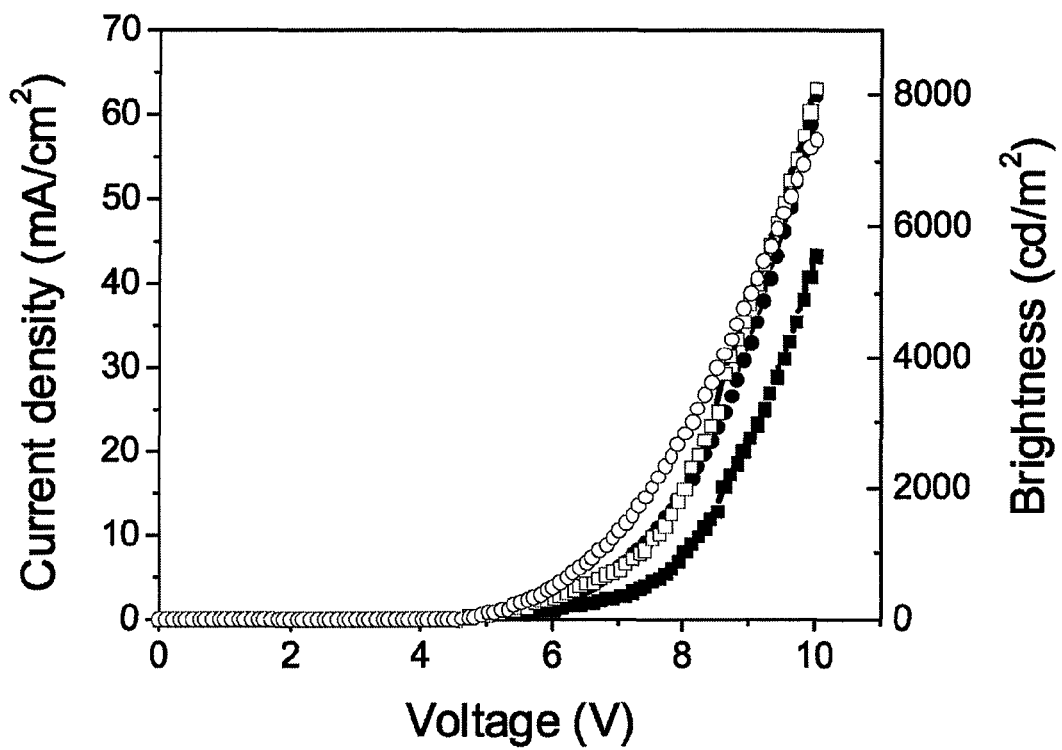
FIG. 8 shows the current density of a device incorporating (POSS)(Ir Compound I), indicated by closed squares, and a device incorporating (POSS)(Ir Compound II), indicated by closed circles; and the brightness of a device incorporating (POSS)(Ir Compound I), indicated by open squares, and a device incorporating (POSS)(Ir Compound II), indicated by open circles.
Figure 9:
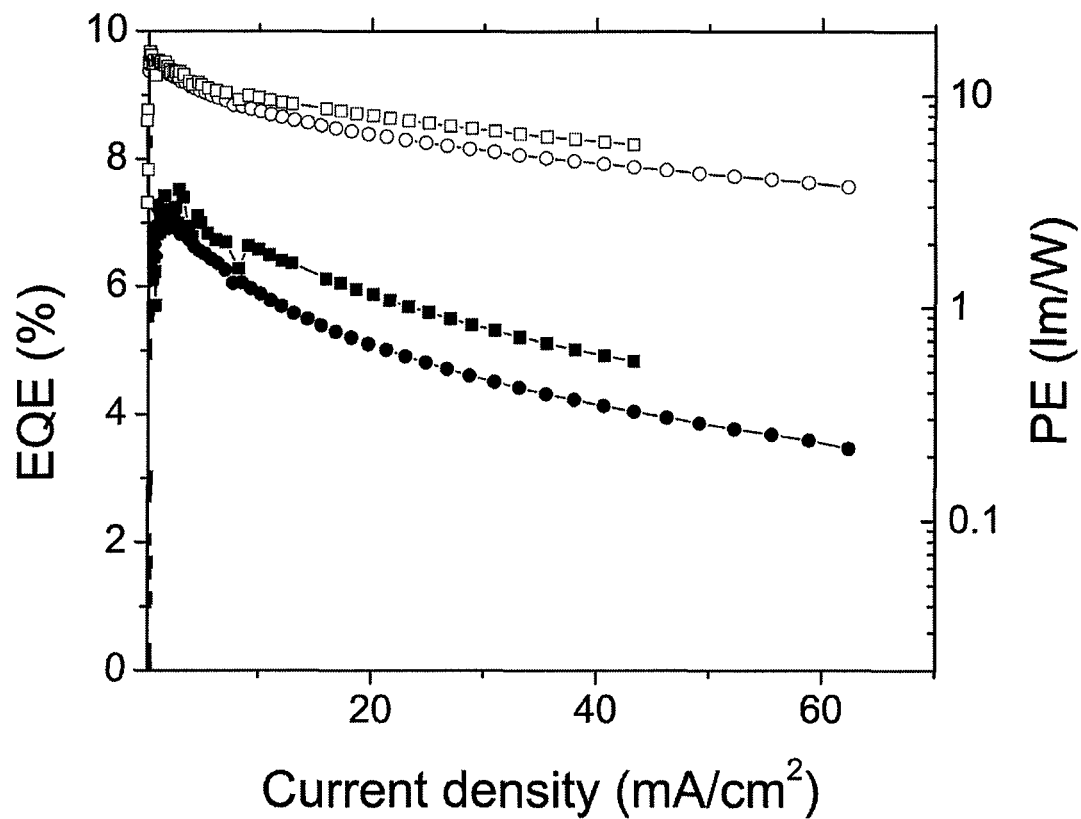
FIG. 9 shows the external quantum efficiency (EQE) of a device incorporating (POSS)(Ir Compound I) indicated by closed squares and a device incorporating (POSS)(Ir Compound II) indicated by closed circles; the power efficiency PE of a device incorporating (POSS)(Ir Compound I) indicated by open squares and a device incorporating (POSS)(Ir Compound II) indicated by open circles.
Figure 10:
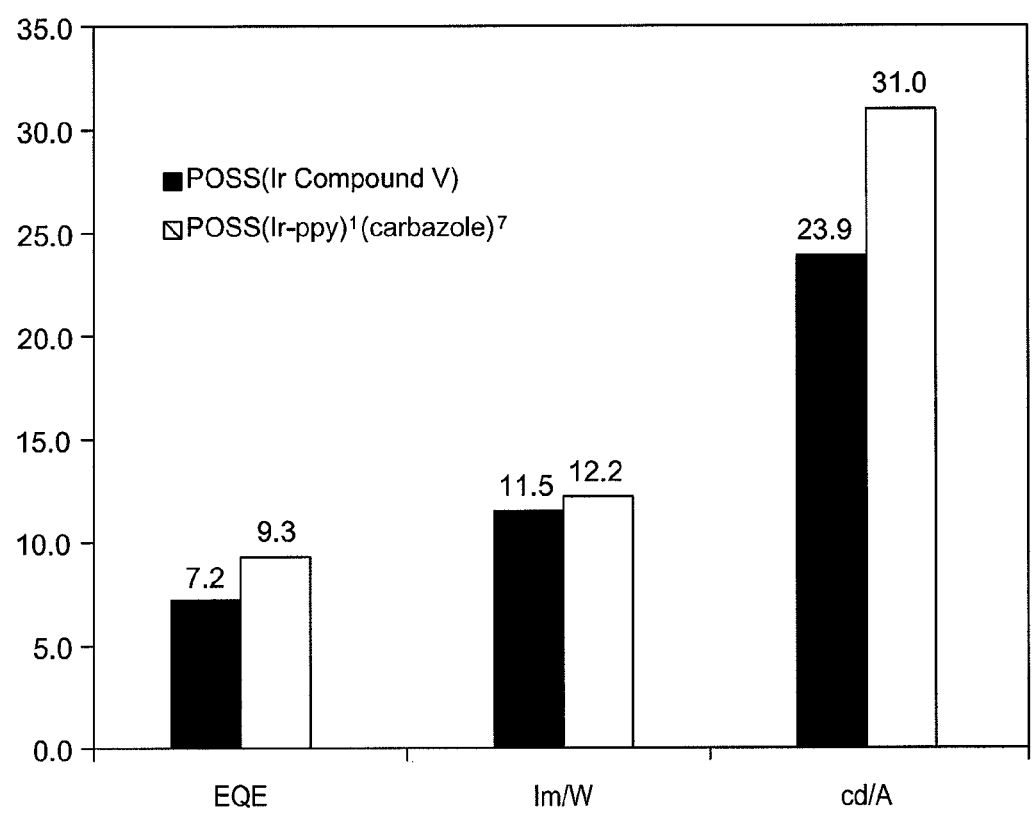
FIG. 10 shows comparison data (EQE, and power efficiency) between POSS(Ir Compound V) and POSS(Ir-ppy)1(carbazole)7.

Fabrication of Light-Emitting Device:

The ITO coated glass substrates were cleaned by ultrasound in acetone and 2-propanol, followed by treatment with oxygen plasma. A layer of PEDOT:PSS (Baytron P purchased from H.C. Starck) was spin-coated at 3000 rpm and annealed at 180° C. for 10 min onto the pre-cleaned and $O_2$-plasma treated (ITO)-substrate, yielding a thickness of around 40 nm. A blend of PVK/PBD (or PVK/OXD-7) (weight ratio 70:30), and iridium complexes (1-6 wt %) in chlorobenzene solution were spin-coated on top of the PEDOT:PSS layer, yielding a 70 nm thick film. Next, the samples were annealed at 80° C. for 30 minutes. A cathode layer comprising an ultra-thin CsF interface layer with a nominal thickness of 1 nm and a ca. 70 nm thick Al layer was deposited by thermal evaporation at a base pressure of $10^{-6}$ mbar onto the annealed blend. Spectra were measured with an ocean optics HR4000 spectrometer and I-V light output measurements were taken with a Keithley 2400 SourceMeter and Newport 2832-C power meter and 818 UV detector. All device operation was carried out inside a nitrogen-filled glove-box. Individual devices had area of about 0.14 cm². An exemplary configuration of the device is shown in FIG. 2.

Example 32

Figure 11:
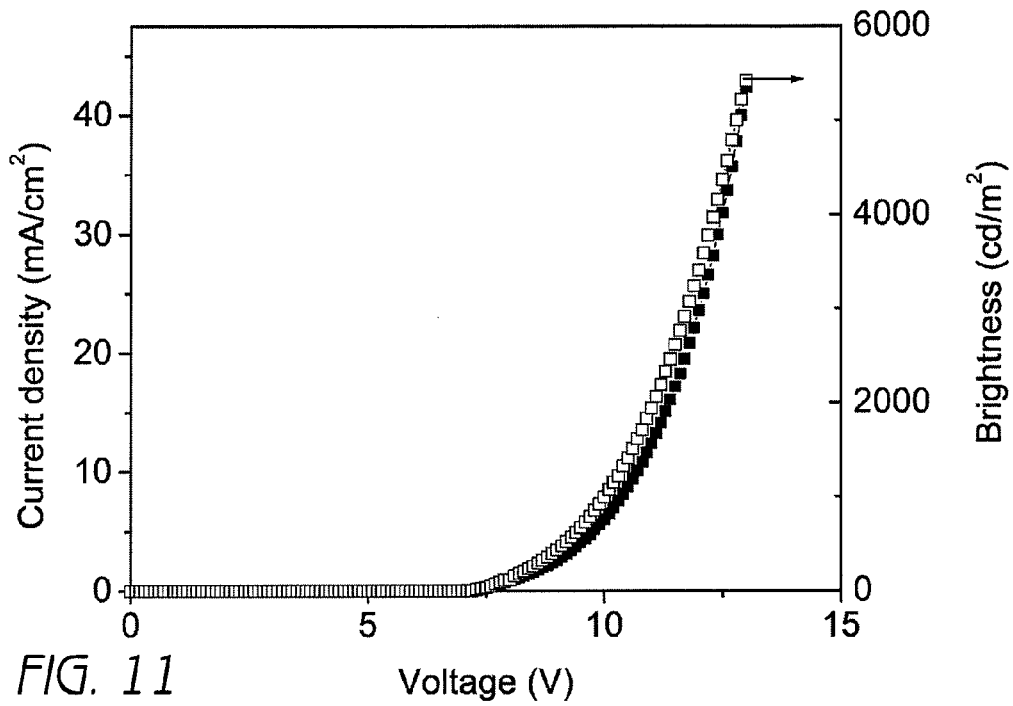
FIG. 11 shows the current density-voltage curve of a device incorporating 0.2 wt % of (POSS)(Ir compound I), 0.4 wt % of (POSS)(Ir compound III) and 5 wt % of (POSS)(Ir compound IV), as indicated by closed squares, and the brightness of the same device as a function of voltage as indicated by open squares.
Figure 12:
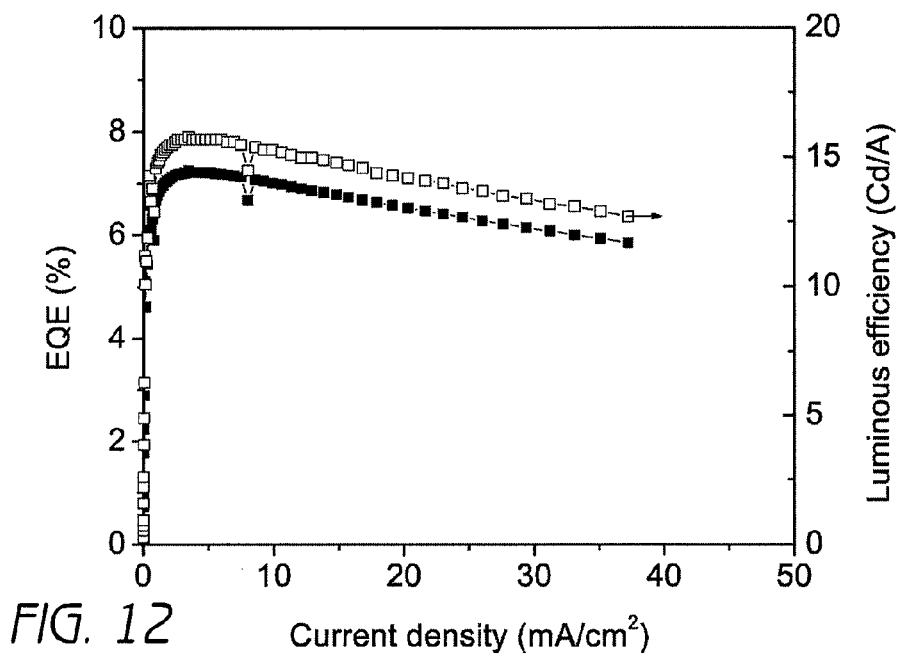
FIG. 12 shows the EQE (indicated by closed squares) and luminous efficiency (indicated by open squares) of a device incorporating 0.2 wt % of (POSS)(Ir compound I), 0.4 wt % of (POSS)(Ir compound III) and 5 wt % of (POSS)(Ir compound IV) as a function of current density.
Figure 13:
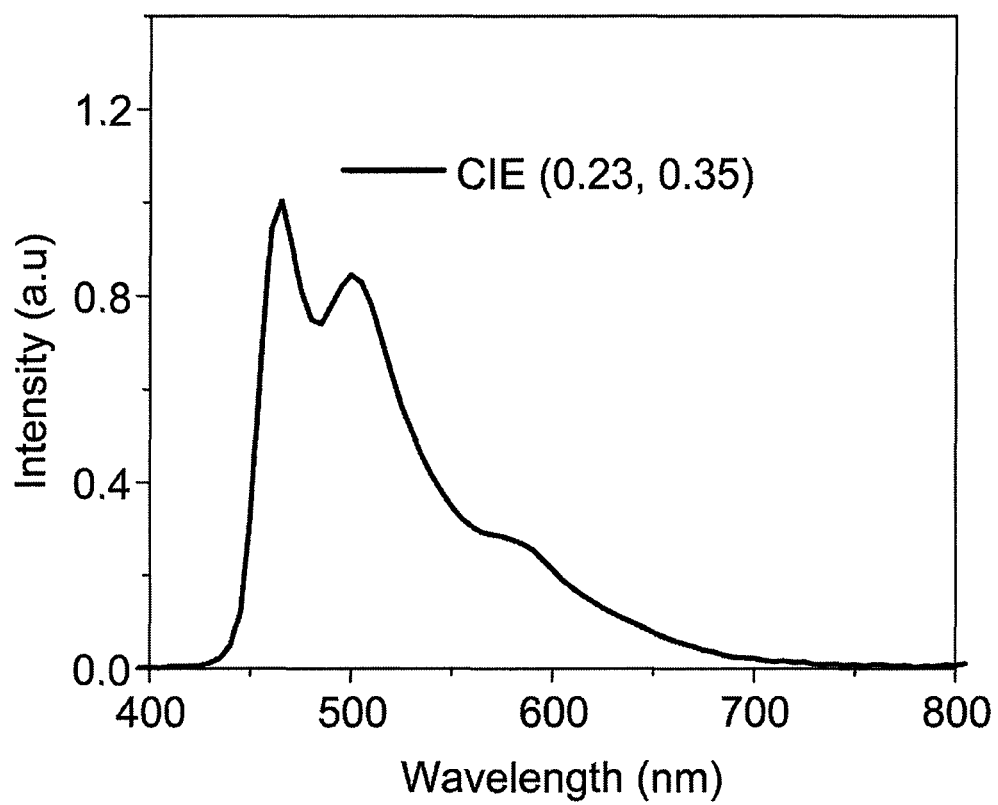
FIG. 13 shows the electroluminescence (EL) spectrum of a device incorporating 0.2 wt % of (POSS)(Ir compound I), 0.4 wt % of (POSS)(Ir compound III) and 5 wt % of (POSS)(Ir compound IV) as a function of wavelength. The CIE coordinate is (0.23, 0.35).

Light-emitting composition containing a mixture of host/lumophore-functionalized nanoparticles. A light-emitting device comprising a mixture of host/lumophore-functionalized nanoparticles can be fabricated using the technique described in EXAMPLE 31. Instead of using one iridium complex, three different Ir complex-functionalized POSS were used to form the light-emitting layer. The light-emitting layer of device A was made by using a mixture of the following Ir complex-functionalized POSS—0.2 wt % of (POSS)(Ir compound I), 0.4 wt % of (POSS)(Ir compound III) and 5 wt % of (POSS)(Ir compound IV). FIG. 11 shows Current-Voltage-Brightness chart of device A. FIG. 12 shows the external quantum efficiency (EQE) and luminous efficiency as a function of current density of device A. FIG. 13 shows the CIE chart of device A.

Figure 14:
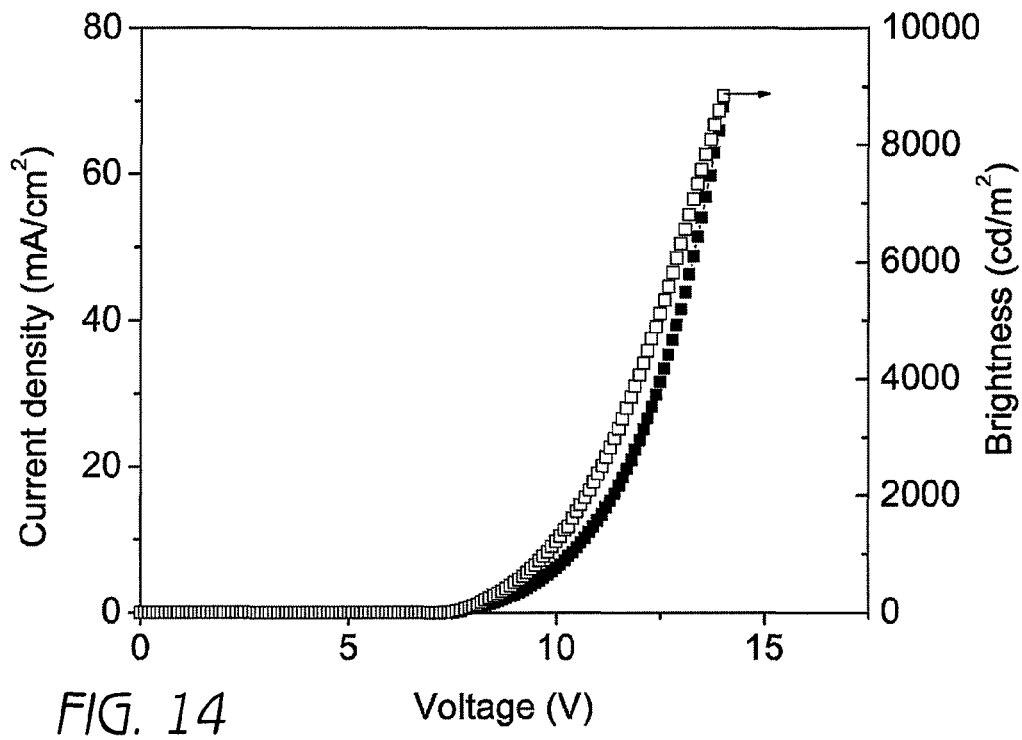
FIG. 14 shows the current density-voltage curve of a device incorporating 0.2 wt % of (POSS)(Ir compound I), 0.6 wt % of (POSS)(Ir compound III) and 5 wt % of (POSS)(Ir compound IV) and an additional electron injection layer, as indicated by closed squares, and the brightness of the same device as a function of voltage as indicated by open squares.
Figure 15:
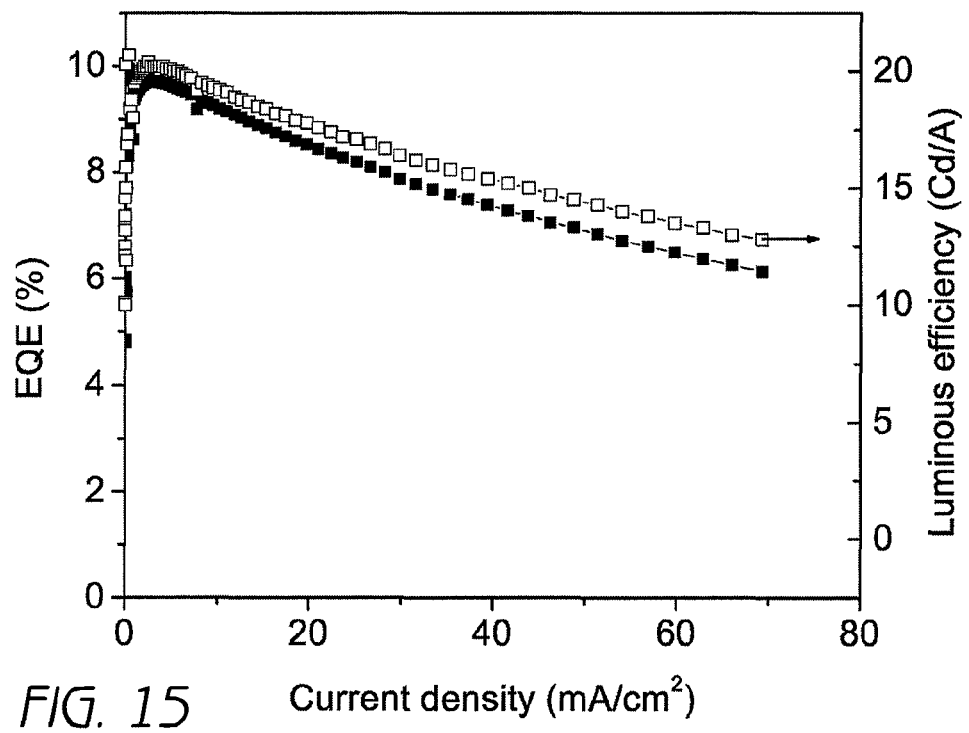
FIG. 15 shows the EQE (indicated by closed squares) and luminous efficiency (indicated by open squares) of a device incorporating 0.2 wt % of (POSS)(Ir compound I), 0.6 wt % of (POSS)(Ir compound III) and 5 wt % of (POSS)(Ir compound IV) and an additional electron injection layer as a function of current density.
Figure 16:
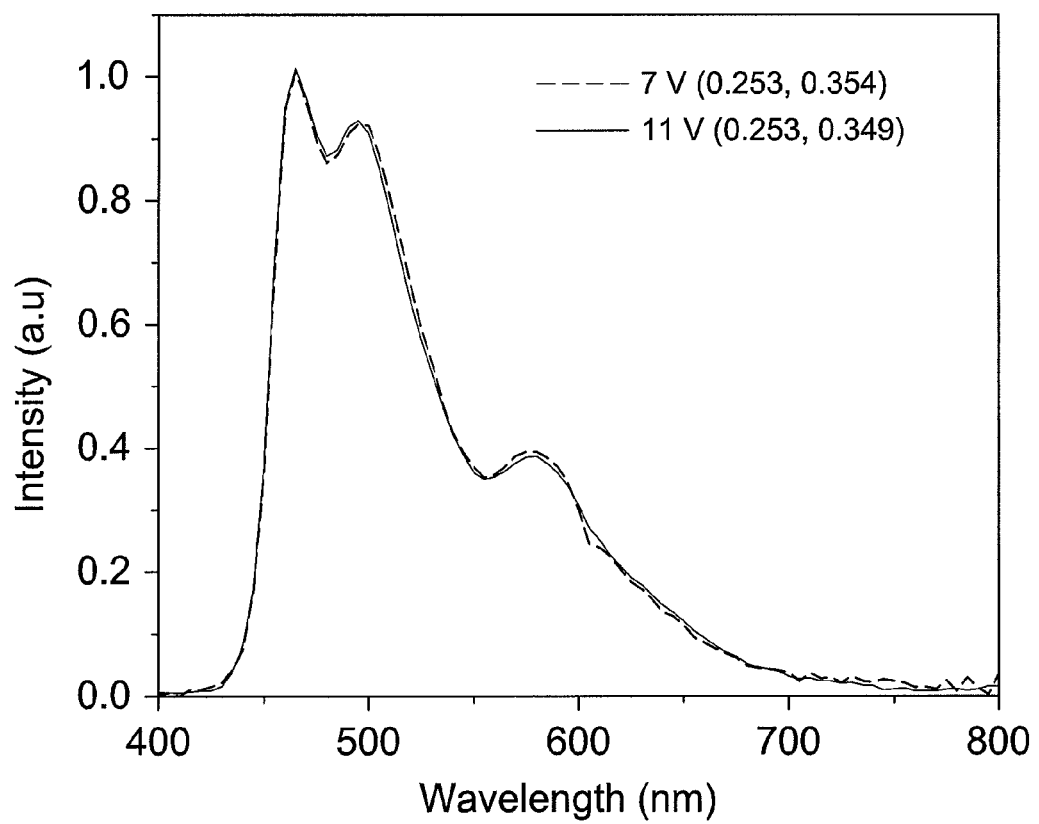
FIG. 16 shows the electroluminescence (EL) spectrum of a device incorporating 0.2 wt % of (POSS)(Ir compound I), 0.6 wt % of (POSS)(Ir compound III) and 5 wt % of (POSS)(Ir compound IV) and an additional electron injection layer as a function of wavelength at 7V and 11V. The CIE coordinate is (0.253, 0.354) at 7V and (0.253, 0.349) at 11V.

The light-emitting layer of device B was made by using a mixture of 0.2 wt % of (POSS)(Ir compound I), 0.6 wt % of (POSS)(Ir compound III) and 5 wt % of (POSS)(Ir compound IV). The device also has an additional electron injection layer, which was made of 30 nm of TPBI spin-coated on top of the light-emitting layer. FIG. 14 shows Current-Voltage-Brightness chart of device B. FIG. 15 shows the external quantum efficiency (EQE) and luminous efficiency as a function of current density of device B. FIG. 16 shows the CIE chart of device B at 7V and 11V. The color stability of device B is very good as the CIE coordinates varied only (0, 0.005) between 7V (1 cd/m²) and 11 V (2400 cd/m²).

It will be appreciated by those skilled in the art that various omissions, additions and modifications may be made to the processes described above without departing from the scope of the invention, and all such modifications and changes are intended to fall within the scope of the invention.

What is claimed is:

1. A light emitting composition comprising one or more compound of formula (I):

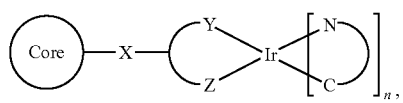
(I)

wherein:
core is a nanoparticle core;
n is 2;
X is a single bond or

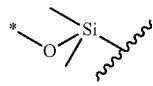 [SMILES: *O[Si](*)(C)C]

wherein * indicates a point of attachment to the core;

each

is independently a first optionally substituted bidentate ligand;

is a second optionally substituted bidentate ligand selected from:

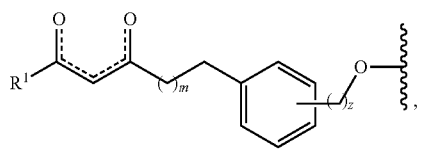

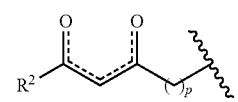

and

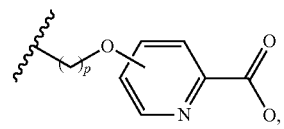

wherein m is an integer in the range of 1 to 9, p is an integer in the range or 1 to 20, z is 0, 1 or 2, R¹ is selected from alkyl, substituted alkyl, aryl and substituted aryl, R² is selected from: alkyl, substituted alkyl, aryl and substituted aryl;
wherein the one or more compound of formula (I) further comprises at least one host attached to the core, wherein the at least one host comprises a hole transport material, an electron transport material or a mixture thereof; and wherein the at least one host comprises

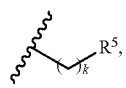

wherein k is 0 or an integer selected from 1 to 20 and each R⁵ is independently selected from the following:

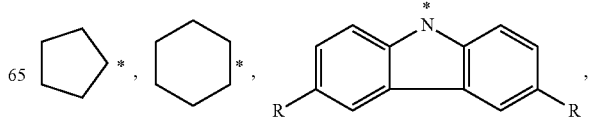

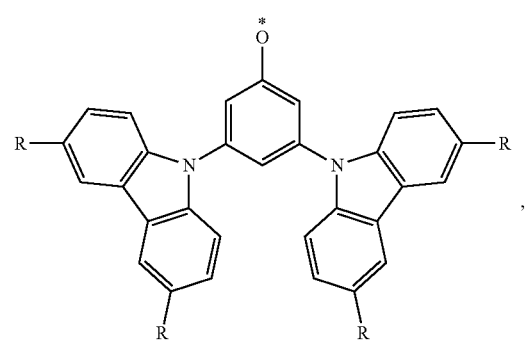
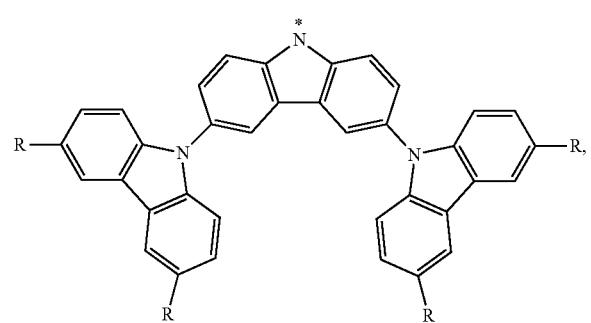
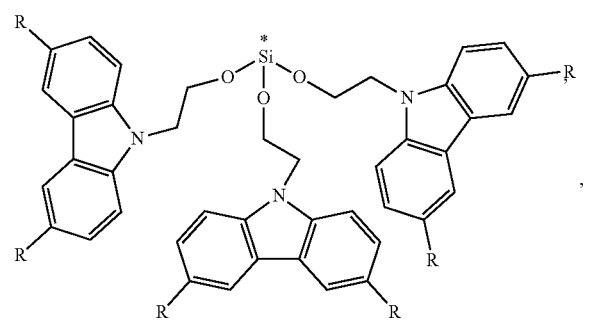
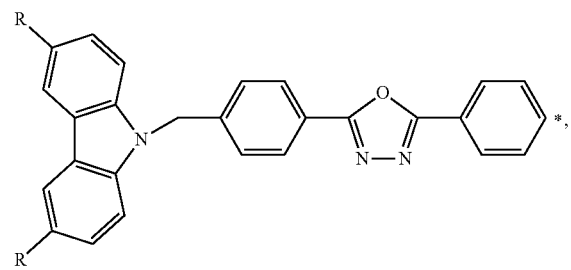
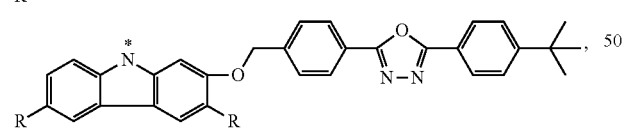
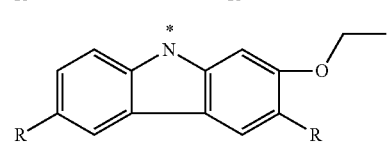
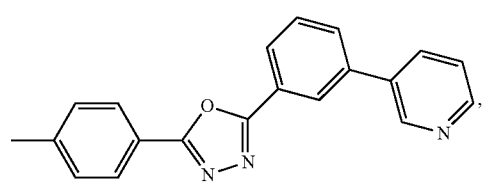
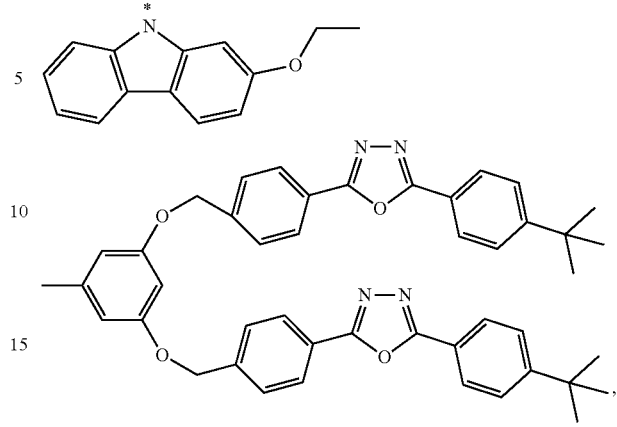
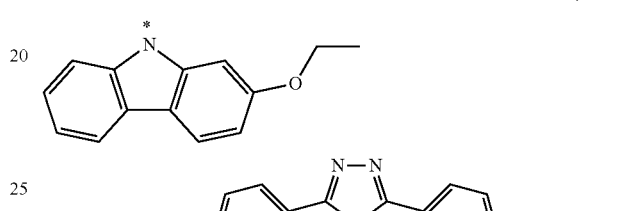
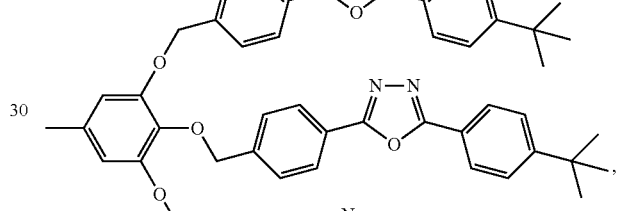
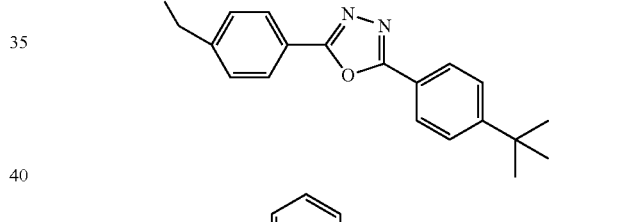
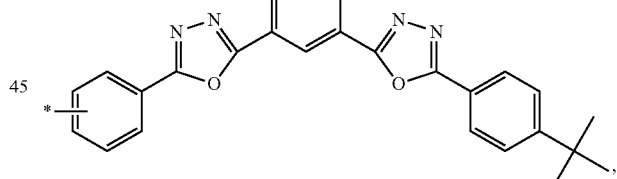
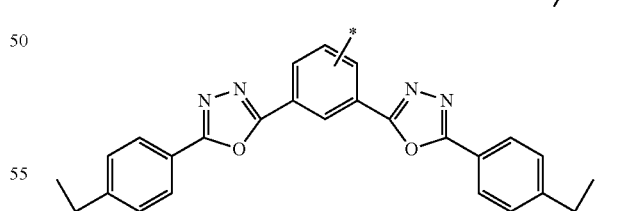

-continued

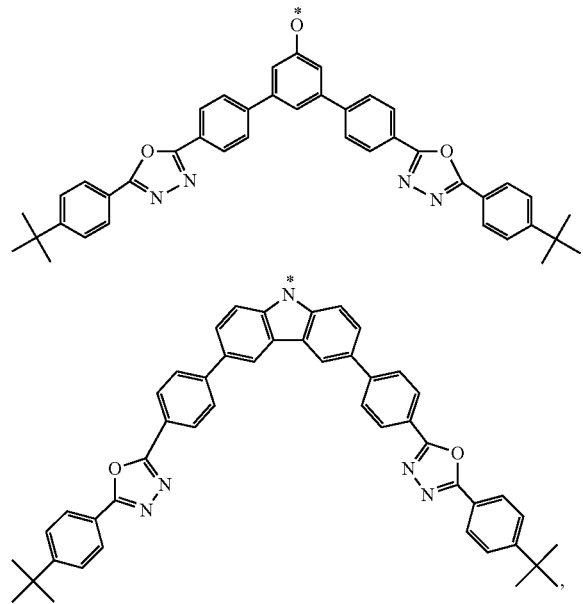

and

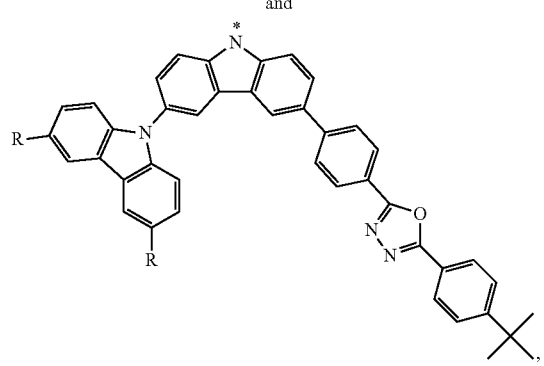

wherein R is independently selected from H or alkyl, and * indicates a point of attachment.

2. The light-emitting composition of claim 1, wherein the core comprises a moiety selected from the group consisting of a silsesquioxane, a cyclophosphazene, a triazine, a cyclodextrin, a calizarene, a phthalocyanine, and a silica particle.

3. The light-emitting composition of claim 2, wherein the silsesquioxane comprises a 1,3,5,7,9,11,13,15-octakis(dimethylsilyloxy)pentacyclo-[9.5.1.13,9.15,15.17,13]-octasiloxane.

4. The light-emitting composition of claim 1, wherein the first optionally substituted bidentate ligand is selected from:

-continued

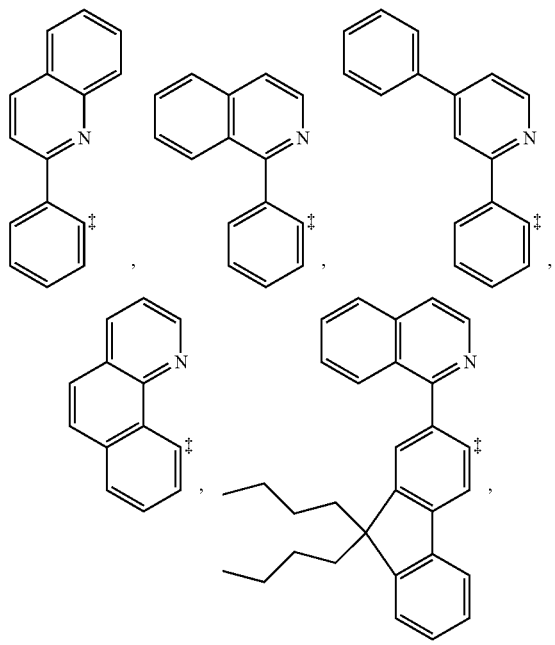

and optionally substituted derivatives thereof, wherein ‡ indicates a point of attachment to the Ir.

5. The light-emitting composition of claim 4, wherein the first optionally substituted bidentate ligand is a substituted derivative selected from:

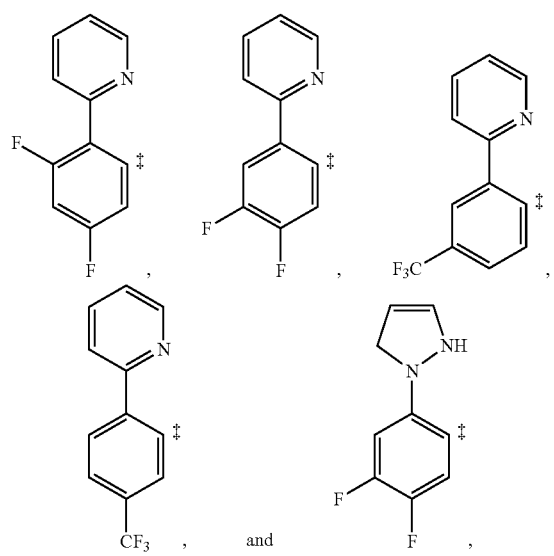

wherein ‡ indicates a point of attachment to the Ir.

6. The light emitting composition of claim 1, wherein the first bidentate ligand is selected from:
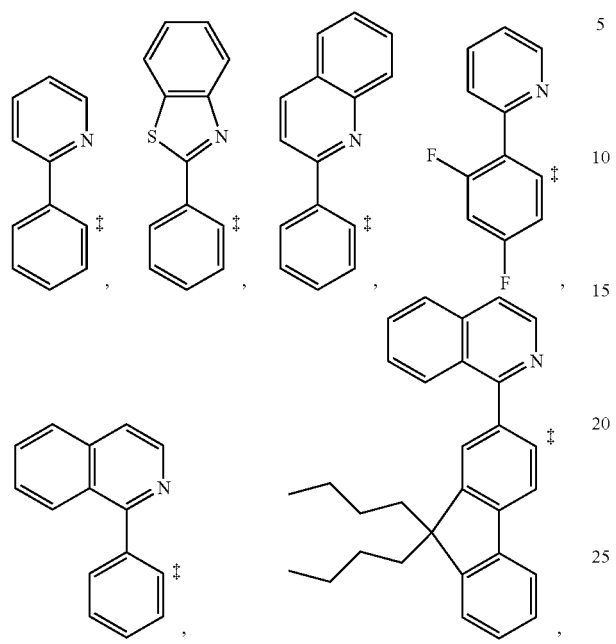
wherein ‡ indicates a point of attachment to the Ir.
7. The light emitting composition of claim 1, wherein the first bidentate ligands are the same.
8. The light emitting composition of claim 1, wherein the compound of formula (I) is selected from:
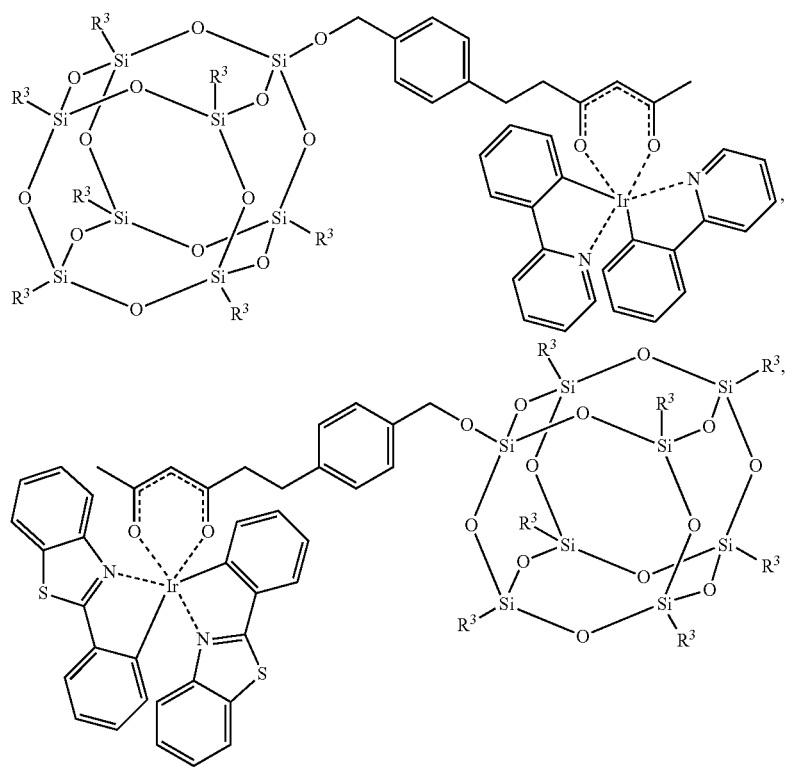

-continued
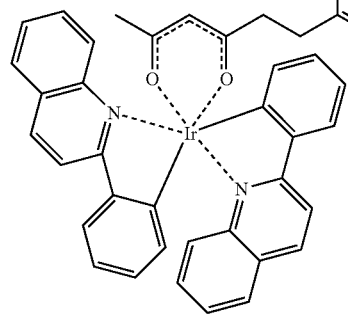
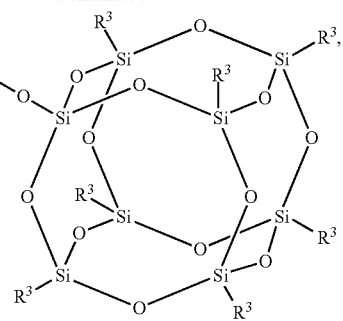
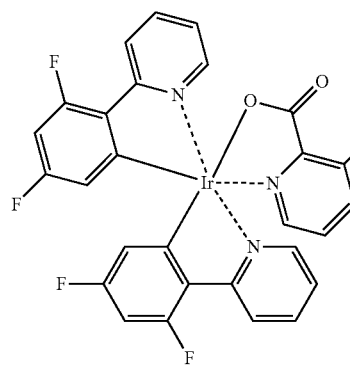
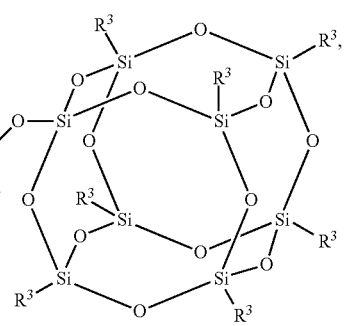
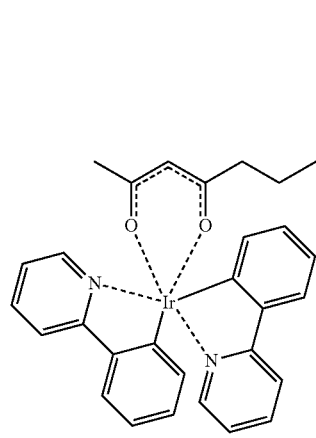
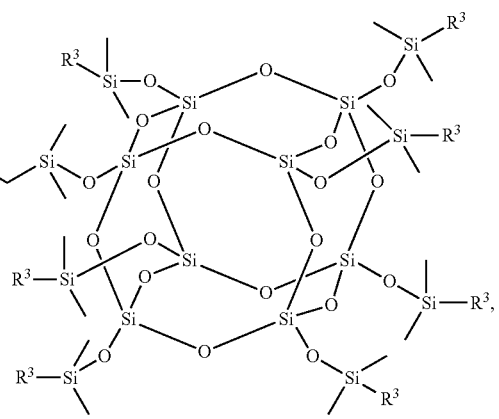
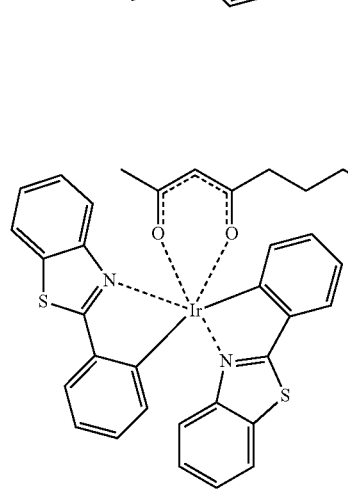
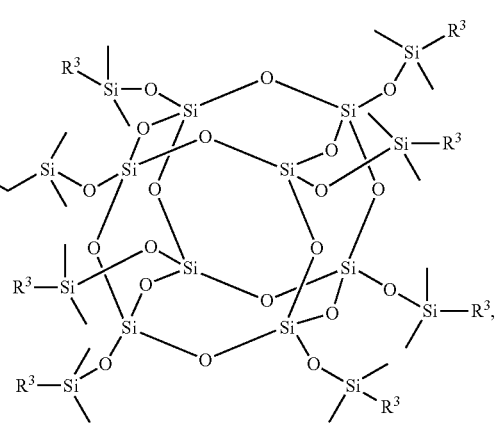

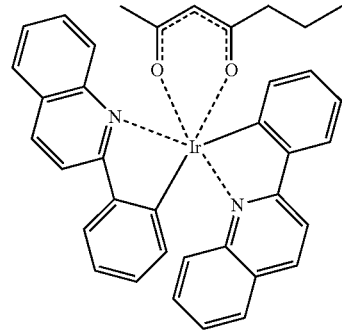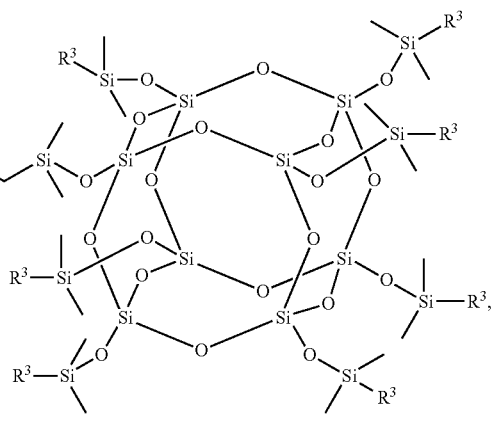
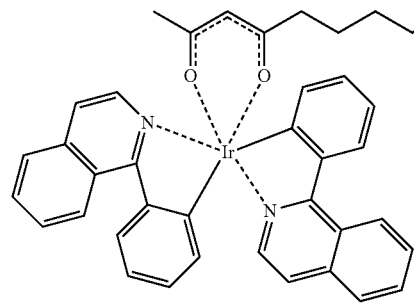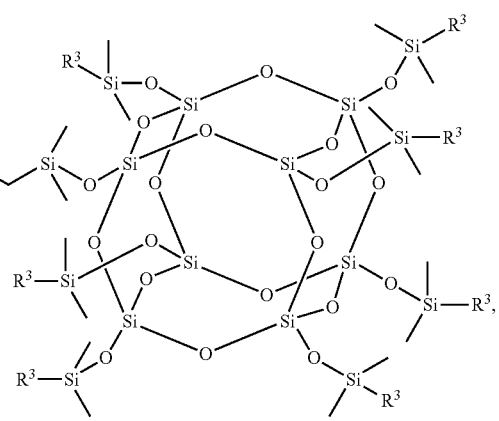
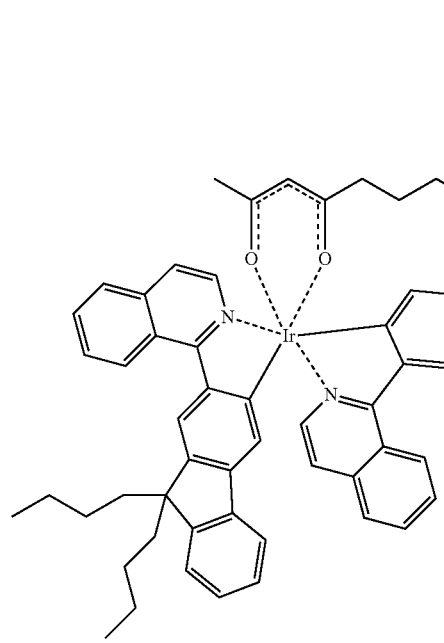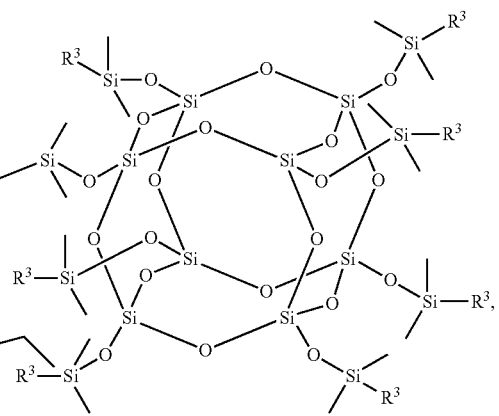

-continued
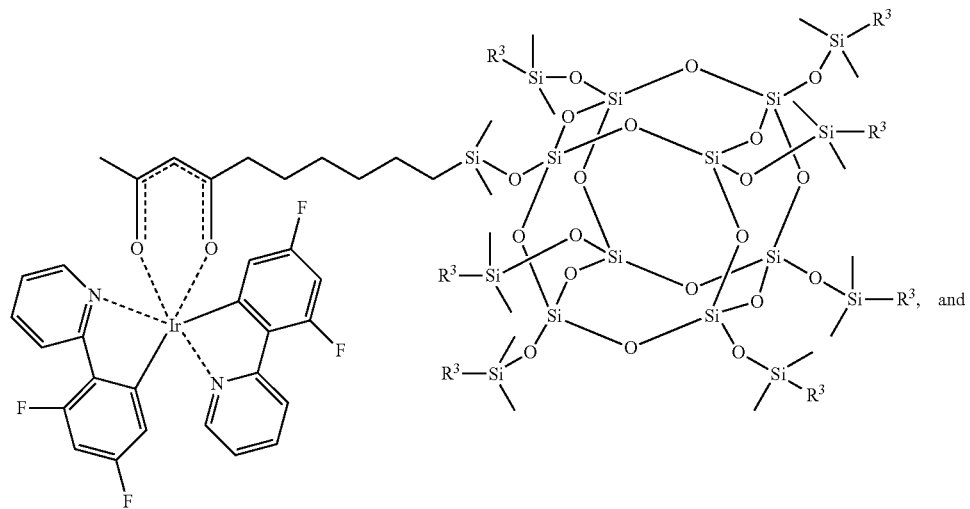
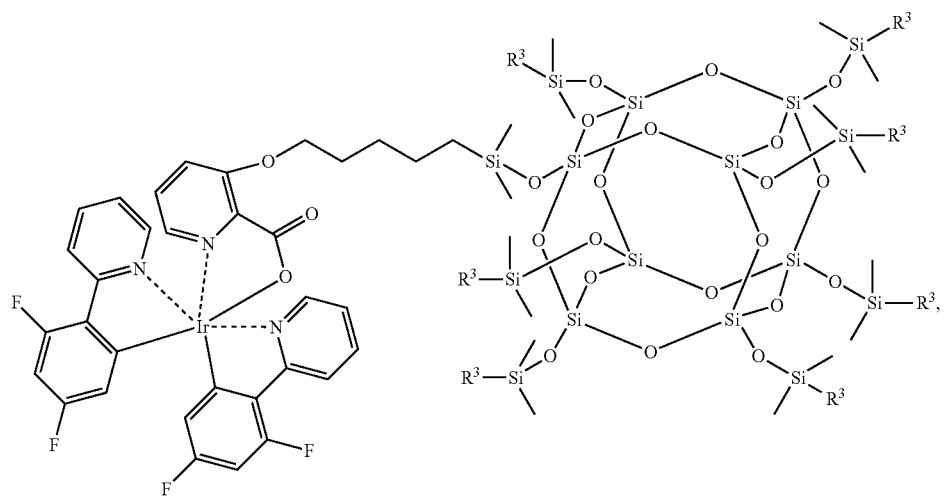
wherein R³ is the host having one of the following formulas
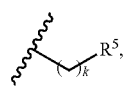
wherein k is 0 or an integer selected from 1 to 20, and R⁵ is selected from the following:
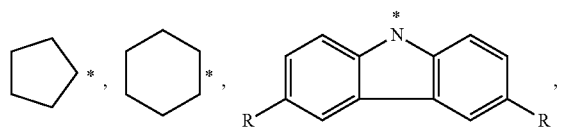
-continued
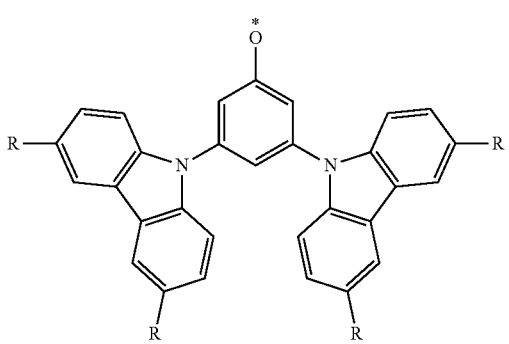

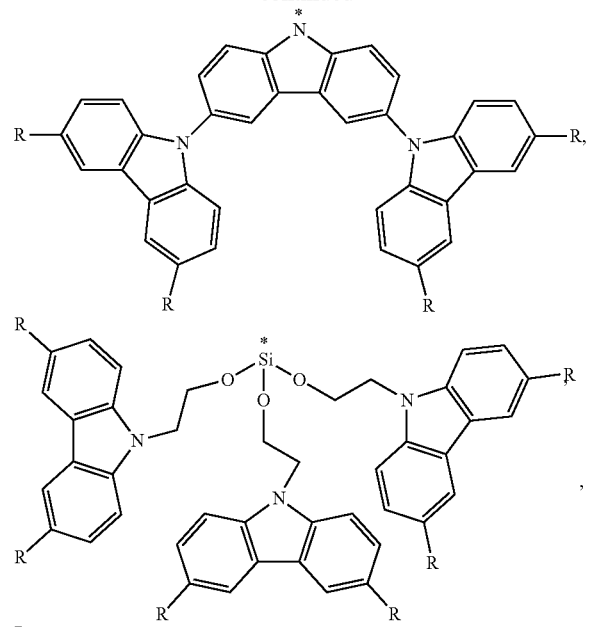
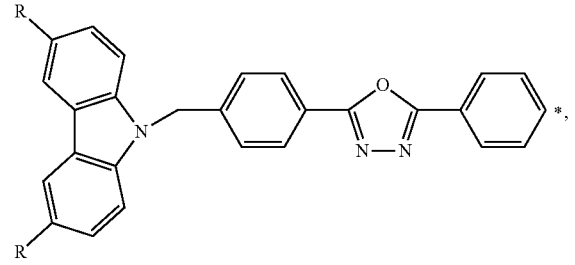
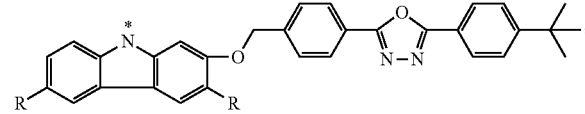
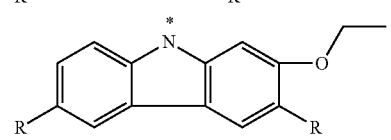
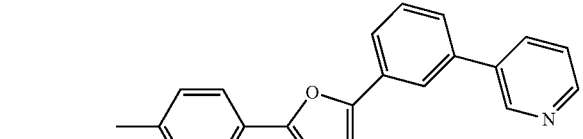
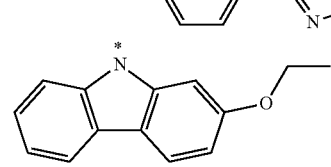
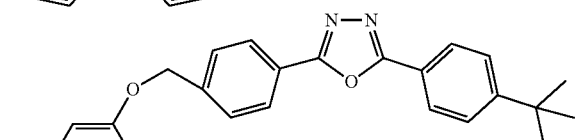
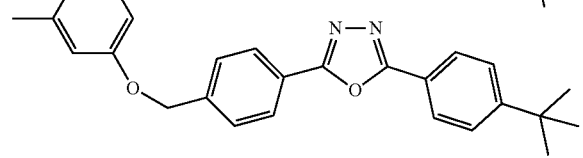
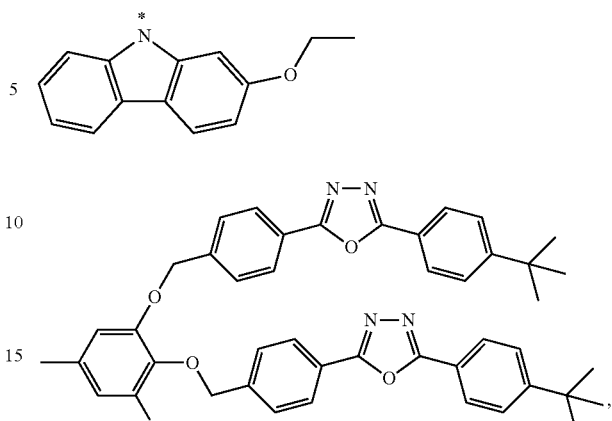
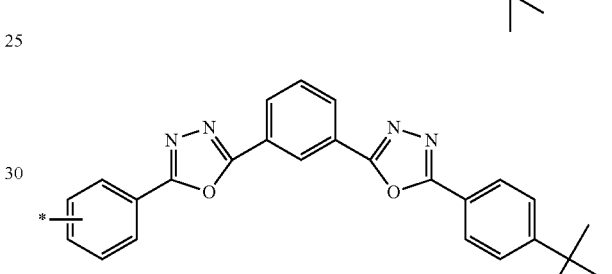
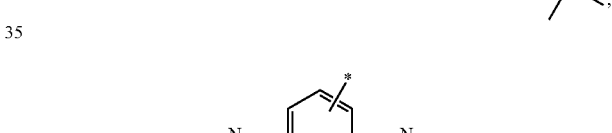
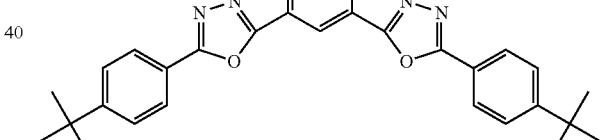
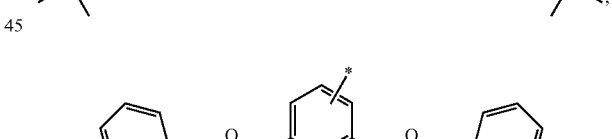
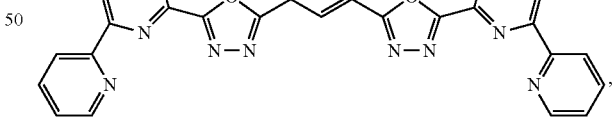
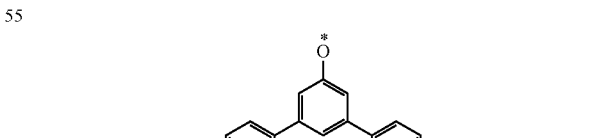
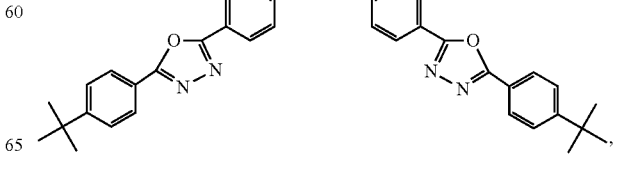

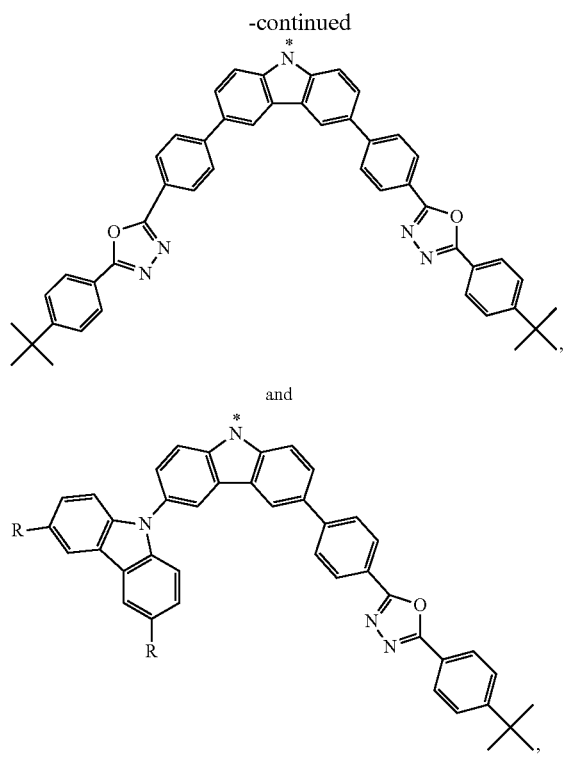

wherein R is independently selected from H or alkyl, and * indicates a point of attachment.

9. A light-emitting device comprising:
an anode layer comprising a high work function metal;
a cathode layer comprising a low work function metal; and
a light-emitting layer comprising the light-emitting composition of claim 1, wherein the light-emitting layer is positioned between, and electrically connected to, the anode layer and the cathode layer.

10. The light-emitting device of claim 9, wherein the light-emitting layer is configured to emit light selected from blue, green, orange, red and white.

11. The light-emitting device of claim 9, wherein the light-emitting layer emits light having a CIE x-coordinate in the range of about 0.27 to about 0.30 and a CIE y-coordinate in the range of about 0.60 to about 0.65.

12. The light-emitting device of claim 9, wherein the amount of the light-emitting composition in the light-emitting layer is in the range of from about 1% to about 99% by weight based on total weight of the light-emitting layer.

13. The light-emitting device of claim 9, wherein the amount of the light-emitting composition in the light-emitting layer is in the range of from about 30% to about 70% by weight based on total weight of the light-emitting layer.

14. The light-emitting device of claim 9, wherein the light-emitting layer further comprises a host material.

15. The light-emitting device of claim 14, wherein the host material comprises an optionally substituted compound selected from: an aromatic-substituted amine, an aromatic-substituted phosphine, a thiophene, an oxadiazole, a triazole, an aromatic phenanthroline, a benzoxazole, a benzothiazole, a quinoline, a pyridine, a dicyanoimidazole, a cyano-substituted aromatic, a carbazole, a polythiophene, a benzidine, a triphenylamine, a phenylenediamine, a polyacetylene, and a phthalocyanine metal complex.

16. The light-emitting device of claim 14, wherein the host material comprises an optionally substituted compound selected from: 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), 3-phenyl-4-(1'-naphthyl)-5-phenyl-1,2,4-triazole (TAZ), 3,4,5-Triphenyl-1,2,3-triazole, 3,5-Bis(4-tert-butyl-phenyl)-4-phenyl[1,2,4]triazole, 2,9-dimethyl-4,7-diphenyl-phenanthroline (bathocuproine or BCP), 2,9-Dimethyl-4,7-diphenyl-1,10-phenanthroline, aluminum tris(8-hydroxyquinolate) (Alq3), 1,3,5-tris(2-N-phenylbenzimidazolyl)benzene (TPBI), 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4'-bis[N,N'-(3-tolyl)amino]-3,3'-dimethylbiphenyl (HMTPD), 1,1-Bis(4-bis(4-methylphenyl)aminophenyl)cyclohexane, 4,4'-N,N'-dicarbazole-biphenyl (CBP), poly(9-vinylcarbazole) (PVK), N,N'N"-1,3,5-tricarbazoloylbenzene (tCP), N,N'-bis(4-butylphenyl)-N,N'-bis(phenyl)benzidine, 4,4',4"-Tris(N-(naphthylen-2-yl)-N-phenylamino)triphenylamine, and 4,4',4"-tris(3-methylphenylphenylamino)triphenylamine (MTDATA).

17. The light-emitting device of claim 9, wherein the high work function metal is selected from the group consisting of Au, Pt, indium-tin-oxide (ITO), and alloys thereof.

18. The light-emitting device of claim 9, wherein the low work function metal is selected from the group consisting of Al, Ag, Mg, Ca, Cu, Mg/Ag, LiF/Al, CsF, CsF/Al, and alloys thereof.

19. The light-emitting device of claim 9, wherein the anode layer has a thickness in the range of about 1 nm to about 1000 nm.

20. The light-emitting device of claim 9, wherein the cathode layer has a thickness in the range of about 1 nm to about 1000 nm.

21. The light-emitting device of claim 9, wherein the light-emitting layer has a thickness in the range of about 20 to about 150 nm.

22. The light-emitting device of claim 9, further comprising an electron injection layer.

23. The light-emitting device of claim 22, wherein the electron injection layer comprises an optionally substituted compound selected from: aluminum quinolate (Alq₃), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline, tris(8-hydroxyquinoliate)aluminum, and a metal thioxinoid and bis(8-quinolinethiolato)zinc.

24. The light-emitting device of claim 9, further comprising an electron transport layer.

25. The light-emitting device of claim 24, wherein the electron transport layer comprises an optionally substituted compound selected from: aluminum tris(8-hydroxyquinolate)(Alq3), 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), 3-phenyl-4-(1'-naphthyl)-5-phenyl-1,2,4-triazole (TAZ), 2,9-dimethyl-4,7-diphenyl-phenanthroline (bathocuproine or BCP), and 1,3,5-tris[2-N-phenylbenzimidazol-z-yl]benzene (TPBI).

26. The light-emitting device of claim 9, further comprising a hole-blocking layer.

27. The light-emitting device of claim 26, wherein the hole-blocking layer comprises an optionally substituted compound selected from: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)cyclohexane.

28. The light-emitting device of claim 9, further comprising an exciton blocking layer.

29. The light-emitting device of claim 28, wherein the exciton blocking layer comprises an optionally substituted compound selected from: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP).

30. The light emitting device of claim 9, further comprising an hole transport layer.

31. The light-emitting device of claim 30, wherein the hole transport layer comprises an optionally substituted compound selected from: a carbazole, a polythiophene, a benzidine, a triphenylamine, a phenylenediamine, an oxadiazole, a polyacetylene and a phthalocyanine metal complex.

32. The light-emitting device of claim 30, wherein the hole transport layer comprises an optionally substituted compound selected from: 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4',4'-tris(3-methylphenylphenylamino)triphenylamine (MTDATA), 4,4'-bis[N,N'-(3-tolyl)amino]-3,3'-dimethylbiphenyl (HMTPD), N,N'N''-1,3,5-tricarbazoloylbenzene (tCP), 4,4'-N,N'-dicarbazole-biphenyl (CBP), poly(9-vinylcarbazole) (PVK), 3,4,5-Triphenyl-1,2,3-triazole, 3,5-Bis(4-tert-butyl-phenyl)-4-phenyl[1,2,4]triazole, 2,9-Dimethyl-4,7-diphenyl-1,10-phenanthroline, 1,1-Bis(4-bis(4-methylphenyl)aminophenyl)cyclohexane, N,N'-bis(4-butylphenyl)-N,N'-bis(phenyl)benzidine, and 4,4',4''-Tris(N-(naphthylen-2-yl)-N-phenylamino)triphenylamine.

33. The light-emitting device of claim 9, further comprising a hole injection layer.

34. The light-emitting device of claim 33, wherein the hole injection layer comprises an optionally substituted compound selected from: a polythiophene. a benzidine, Na triphenylamine, a phenylenediamine. an oxadiazole, a polyacetylene, and a phthalocyanine metal complex.

35. The light-emitting device of claim 33, wherein the hole injection layer comprises an optionally substituted compound selected from: Poly(3,4-ethylenedioxythiophene (PEDOT)/polystyrene sulphonic acid (PSS), N,N,N',N'-tetraphenylbenzidine, poly(N,N'-bis(4-butylphenyl)-N,N'-bis(phenyl)benzidine), N'-bis(4-methylphenyl)-N,N'-bis(phenyl)-1,4-phenylenediamine, 4,4',4''-tris(N-(naphthylen-2-yl)-N-phenylamino)triphenylamine, 3-bis(5-(4-diphenylamino)phenyl-1,3,4-oxadiazol-2-yl)benzene, and poly(1,2-bis-benzylthio-acetylene).

36. A process of making the light-emitting device of claim 9 comprising forming the light-emitting layer by a wet process.

37. The process of claim 36, wherein the wet process is selected from the group consisting of spraying, spin coating, drop casting, inkjet printing, and screen printing.

38. An iridium-functionalized nanoparticle represented by one of the following formulas:

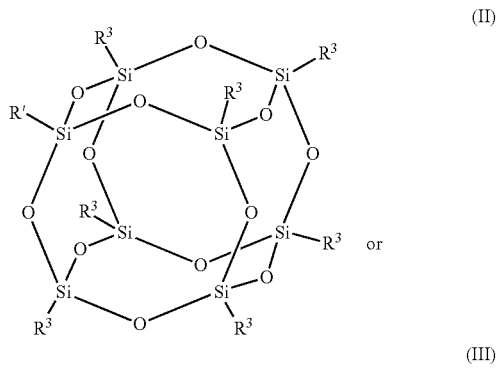

(II)

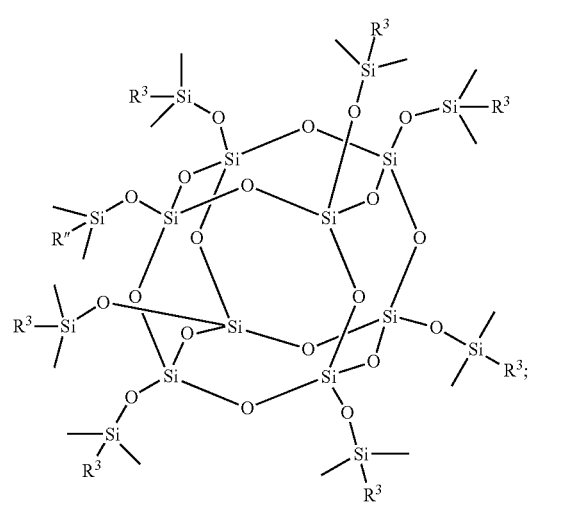

(III)

wherein R' is represented by

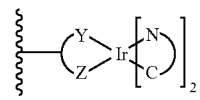

or

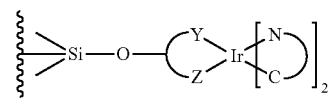

and R" is represented by

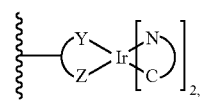

wherein each
is independently a first optionally substituted bidentate ligand, and
is a second optionally substituted bidentate ligand;
R³ is
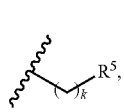
wherein k is 0 or an integer selected from 1 to 20, and R⁵ is independently selected from the following:
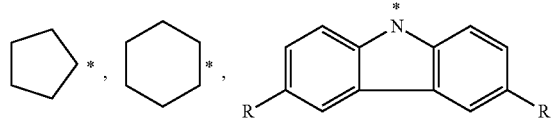
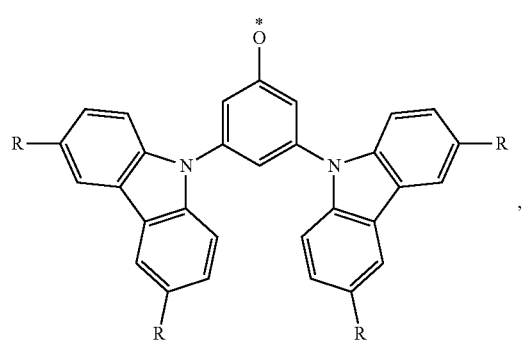
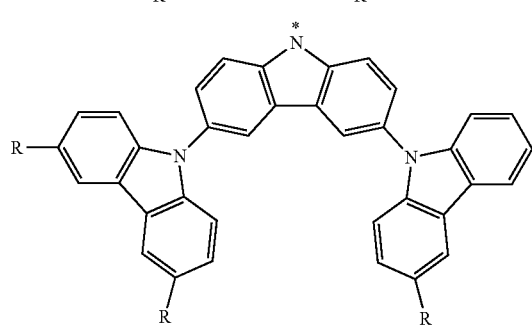
-continued
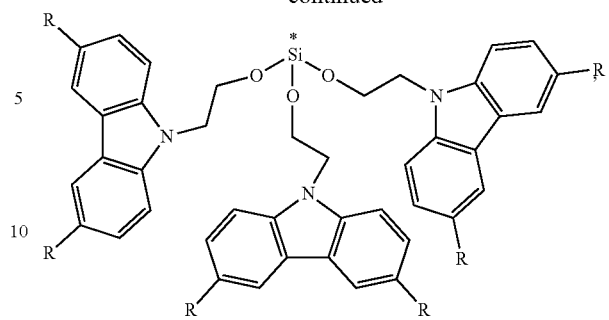
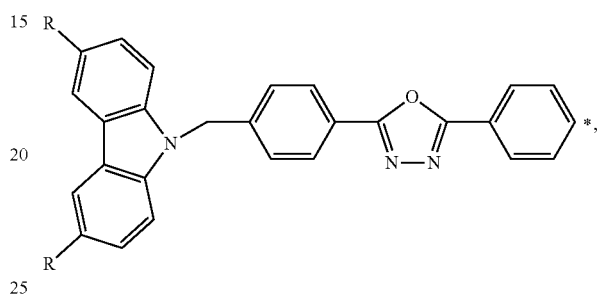
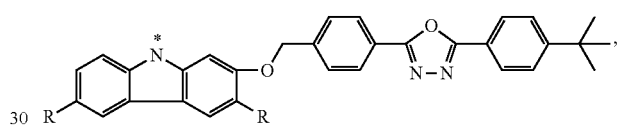
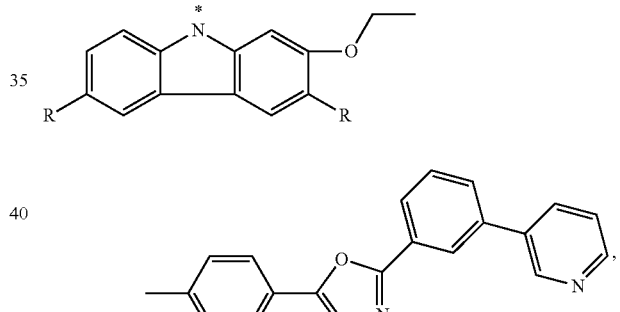
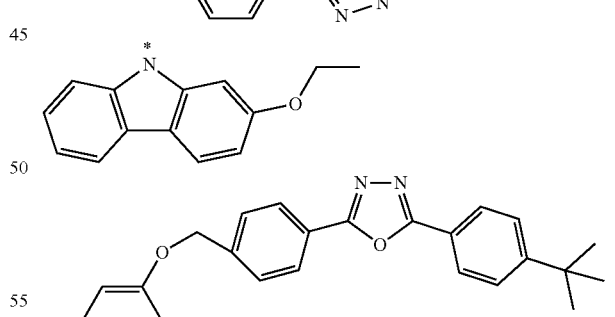
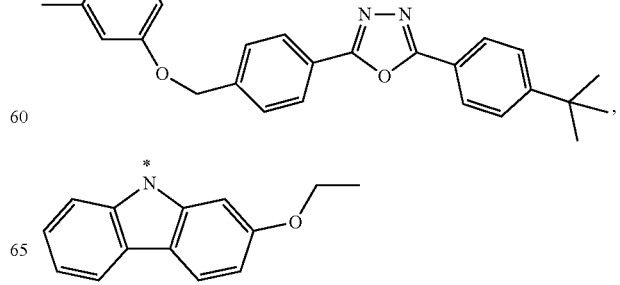

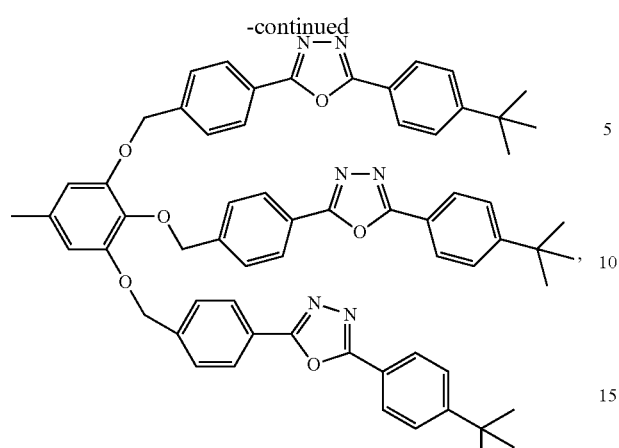

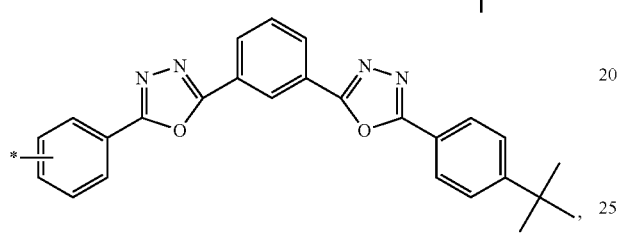

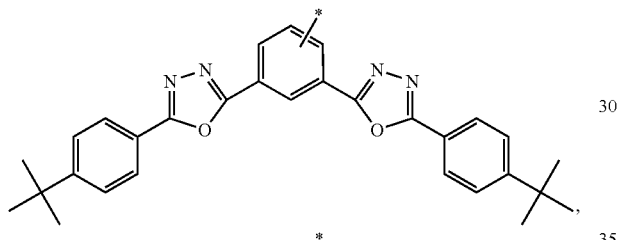

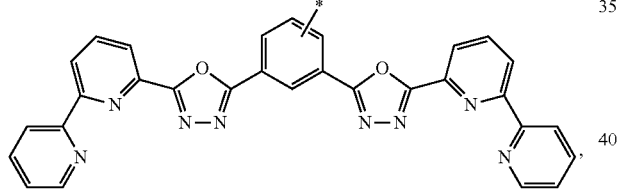

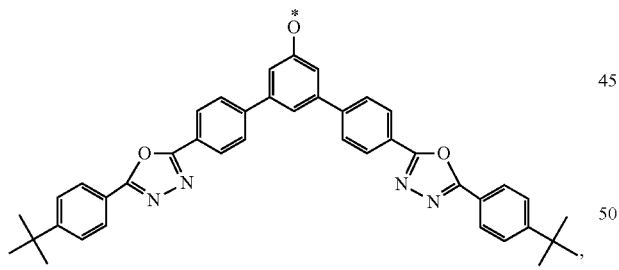

and

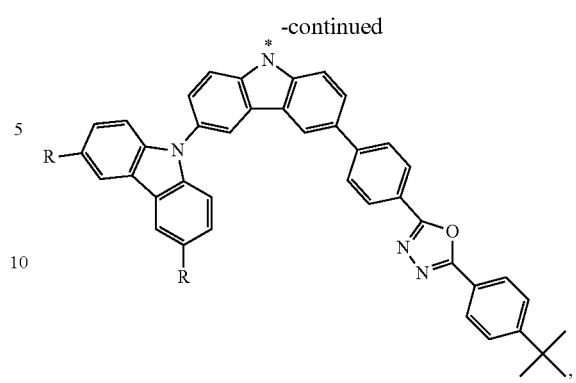

wherein R is independently selected from H or alkyl, and * indicates a point of attachment.

39. The iridium-functionalized nanoparticle of claim 38, wherein

is selected from:

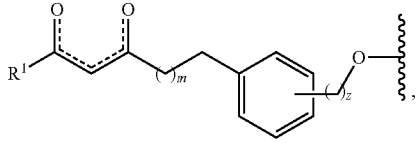

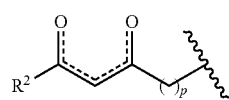

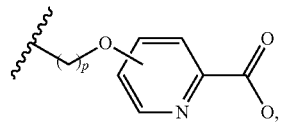

and optionally substituted derivatives thereof, wherein m is an integer in the range of 1 to 9, p is an integer in the range or 1 to 20, z is 0, 1 or 2, $R^1$ is selected from alkyl, substituted alkyl, aryl and substituted aryl, and $R^2$ is selected from alkyl, substituted alkyl, aryl and substituted aryl.

40. The iridium-functionalized nanoparticle of claim 38, wherein

is selected from:
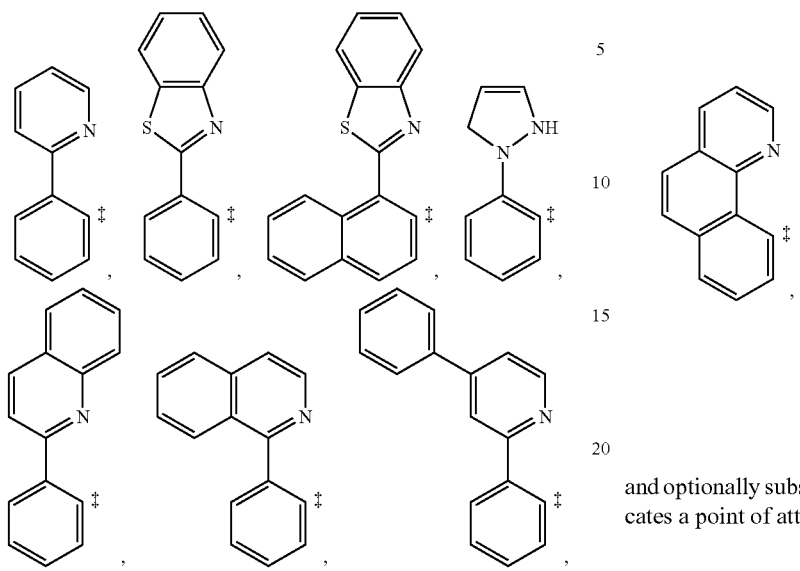
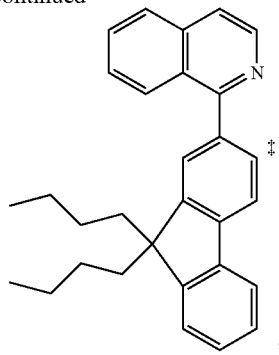
and optionally substituted derivatives thereof, wherein ‡ indicates a point of attachment to the Ir.
* * * * *